US011918677B2

(12) United States Patent
Labib et al.

(10) Patent No.: US 11,918,677 B2
(45) Date of Patent: Mar. 5, 2024

(54) ORAL CAVITY CLEANING COMPOSITION METHOD AND APPARATUS

(71) Applicant: Novaflux Inc., Princeton, NJ (US)

(72) Inventors: Mohamed Emam Labib, West Palm Beach, FL (US); Antonio Perazzo, Princeton, NJ (US)

(73) Assignee: Protegera, Inc., Princeton, NJ (US)

( * ) Notice: Subject to any disclaimer, the term of this patent is extended or adjusted under 35 U.S.C. 154(b) by 0 days.

(21) Appl. No.: 17/062,424

(22) Filed: Oct. 2, 2020

(65) Prior Publication Data

US 2021/0121386 A1    Apr. 29, 2021

Related U.S. Application Data

(60) Provisional application No. 62/913,565, filed on Oct. 10, 2019, provisional application No. 62/910,049, filed on Oct. 3, 2019.

(51) Int. Cl.
| | | |
|---|---|---|
| *A61Q 11/00* | (2006.01) | |
| *A61K 8/21* | (2006.01) | |
| *A61K 8/25* | (2006.01) | |
| *A61K 8/73* | (2006.01) | |

(52) U.S. Cl.
CPC .............. *A61K 8/731* (2013.01); *A61K 8/21* (2013.01); *A61Q 11/00* (2013.01); *A61K 2800/28* (2013.01); *A61K 2800/48* (2013.01)

(58) Field of Classification Search
CPC ... C08L 1/02; C08L 2205/16; A61K 2300/00; A61K 8/731; A61K 31/717; A61K 9/2054; A61K 47/38; A61K 8/027; A61K 2800/28; A61K 2800/412; A61K 8/21; A61K 8/25; A61K 6/898; A61K 8/73; A61K 6/52; A61K 2800/48; A61Q 11/00
See application file for complete search history.

(56) References Cited

U.S. PATENT DOCUMENTS

| | | | |
|---|---|---|---|
| 3,209,771 A | 10/1965 | Gogarty et al. | |
| 3,225,787 A | 12/1965 | Gogarty et al. | |
| 3,852,200 A | 12/1974 | Meyer | |
| 4,003,393 A | 1/1977 | Jaggard et al. | |
| 4,075,316 A * | 2/1978 | Cordon ............... | A61K 8/0254 424/49 |
| 4,216,026 A | 8/1980 | Scott | |
| 4,254,559 A | 3/1981 | Purinton, Jr. | |
| 4,270,914 A | 6/1981 | Dahl | |
| 4,304,050 A | 12/1981 | Morud et al. | |
| 4,341,807 A | 7/1982 | Turbak et al. | |
| 4,362,713 A | 12/1982 | Buck | |
| 4,374,702 A | 2/1983 | Turbak et al. | |
| 4,378,381 A | 3/1983 | Turbak et al. | |
| 4,406,030 A | 9/1983 | Platts | |
| 4,416,703 A | 11/1983 | Scott | |
| 4,473,408 A | 9/1984 | Purinton, Jr. | |
| 4,481,077 A | 11/1984 | Herrick | |
| 4,500,546 A | 2/1985 | Turbak et al. | |
| 4,525,220 A | 6/1985 | Sasa et al. | |
| 4,543,131 A | 9/1985 | Purinton, Jr. | |
| 4,629,575 A | 12/1986 | Weibel | |
| 4,693,840 A | 9/1987 | Trinh et al. | |
| 4,775,525 A | 10/1988 | Pera | |
| 4,805,598 A | 2/1989 | Ueda | |
| 4,855,128 A | 8/1989 | Lynch et al. | |
| 4,860,821 A | 8/1989 | Hagewood | |
| 4,914,170 A | 4/1990 | Chang et al. | |
| 5,075,104 A | 12/1991 | Gressel et al. | |
| 5,202,112 A * | 4/1993 | Prencipe ............... | A61Q 11/00 424/52 |
| 5,260,021 A | 11/1993 | Zeleznick | |
| 5,346,339 A | 9/1994 | Himes et al. | |
| 5,362,480 A | 11/1994 | Au et al. | |
| 5,443,801 A | 8/1995 | Langford | |
| 5,512,199 A | 4/1996 | Khan et al. | |
| 5,527,204 A | 6/1996 | Rhoades | |
| 5,681,399 A | 10/1997 | Okano | |
| 5,703,026 A | 12/1997 | Setser et al. | |

(Continued)

FOREIGN PATENT DOCUMENTS

| | | |
|---|---|---|
| CA | 2 013 120 A1 | 10/1990 |
| CA | 2 921 174 A1 | 2/2015 |

(Continued)

OTHER PUBLICATIONS

International Search Report and Written Opinion for Application No. PCT/US2020/054149 dated Jan. 19, 2021.

(Continued)

*Primary Examiner* — Tracy Liu

(74) *Attorney, Agent, or Firm* — Merchant & Gould P.C.

(57) ABSTRACT

A composition for improved oral care includes fibrillated material and friction elements for removal of plaque biofilm, and additional ingredients useful in oral care compositions. The composition also may include particulate SuperAbsorbent Polymer, which may be surface cross-linked. Certain ingredients may be minimized or avoided to reduce the lubricity of the composition. The composition may be a viscoelastic fluid having a desired viscosity, yield stress and elastic modulus. The efficacy can be characterized by its removal of biofilm due to flow inside tubes. Also useful are standard rheological and tribological measurements. Also disclosed are apparatus for administering the composition, and methods.

37 Claims, 20 Drawing Sheets

(56) References Cited

U.S. PATENT DOCUMENTS

| | | |
|---|---|---|
| 5,731,080 A | 3/1998 | Cousin et al. |
| 5,763,335 A | 6/1998 | Hermann |
| 5,885,133 A | 3/1999 | Williams, Jr. |
| 5,998,349 A | 12/1999 | Guillou |
| 6,027,572 A | 2/2000 | Labib et al. |
| 6,037,380 A | 3/2000 | Venables et al. |
| 6,045,623 A | 4/2000 | Cannon |
| 6,272,713 B1 | 8/2001 | Lotwin |
| 6,288,154 B1 | 9/2001 | Rhoades |
| 6,447,990 B1 | 9/2002 | Alfa |
| 6,506,435 B1 | 1/2003 | Lundberg et al. |
| 6,541,627 B1 | 4/2003 | Ono et al. |
| 6,602,994 B1 | 8/2003 | Cash et al. |
| 6,683,036 B2 | 1/2004 | Foley et al. |
| 6,699,331 B1 | 3/2004 | Kritzler |
| 6,797,245 B2 | 9/2004 | Nakanishi et al. |
| 6,803,107 B2 | 10/2004 | Mitchell et al. |
| 6,849,581 B1 | 2/2005 | Thompson et al. |
| 6,889,400 B2 | 5/2005 | Kawazoe et al. |
| 6,903,057 B1 | 6/2005 | Tsaur |
| 6,905,986 B2 | 6/2005 | Ranganathan et al. |
| 6,967,027 B1 | 11/2005 | Heux et al. |
| 7,037,405 B2 | 5/2006 | Nguyen et al. |
| 7,135,163 B2 | 11/2006 | Winston et al. |
| 7,306,846 B2 | 12/2007 | Dezutter et al. |
| 7,341,623 B2 | 3/2008 | Holl et al. |
| 7,343,972 B2 | 3/2008 | Willingham et al. |
| 7,393,820 B2 | 7/2008 | Soldanski et al. |
| 7,459,028 B2 | 12/2008 | Kral et al. |
| 7,776,807 B2 | 8/2010 | Canto et al. |
| 7,820,873 B2 | 10/2010 | Sun et al. |
| 7,824,608 B2 | 11/2010 | Kuroshima et al. |
| 7,879,289 B2 | 2/2011 | Williams |
| 7,883,726 B2 | 2/2011 | Crutchfield, III |
| 7,888,308 B2 | 2/2011 | Swazey |
| 7,994,111 B2 | 8/2011 | Caggioni et al. |
| 8,097,574 B2 | 1/2012 | Heath et al. |
| 8,187,056 B2 | 5/2012 | Hashish et al. |
| 8,206,349 B2 | 6/2012 | Slenker et al. |
| 8,211,411 B2 | 7/2012 | Deckner et al. |
| 8,357,378 B2 | 1/2013 | Wallace et al. |
| 8,445,422 B2 | 5/2013 | Gonzales et al. |
| 8,466,097 B2 | 6/2013 | Allef et al. |
| 8,546,316 B2 | 10/2013 | Perez-Prat Vinuesa et al. |
| 8,546,558 B2 | 10/2013 | Ankerfors et al. |
| 8,642,529 B2 | 2/2014 | Palla-Venkata et al. |
| 8,703,691 B2 | 4/2014 | Caggioni et al. |
| 8,716,213 B2 | 5/2014 | Caggioni et al. |
| 8,741,855 B2 | 6/2014 | Quave et al. |
| 8,772,359 B2 | 7/2014 | Swazey |
| 8,785,621 B2 | 7/2014 | Flury et al. |
| 8,790,301 B2 | 7/2014 | Slenker et al. |
| 8,795,637 B2 | 8/2014 | Deckner et al. |
| 8,852,643 B2 | 10/2014 | Gonzales et al. |
| 8,920,574 B2 | 12/2014 | Bhaumik et al. |
| 8,980,011 B2 | 3/2015 | Sumnicht et al. |
| 9,045,716 B2 | 6/2015 | Swazey et al. |
| 9,149,274 B2 | 10/2015 | Spivey et al. |
| 9,162,007 B2 | 10/2015 | Bitis et al. |
| 9,163,201 B2 | 10/2015 | Gonzales et al. |
| 9,193,982 B2 | 11/2015 | Sjoede et al. |
| 9,289,449 B2 | 3/2016 | Sershen et al. |
| 9,339,172 B2 | 5/2016 | Slenker et al. |
| 9,370,478 B2 | 6/2016 | Bonner et al. |
| 9,453,156 B2 | 9/2016 | Wu |
| 9,457,453 B2 | 10/2016 | Seth et al. |
| 9,492,373 B2 | 11/2016 | Canova et al. |
| 9,534,191 B2 | 1/2017 | Fernandez-Prieto et al. |
| 9,549,890 B2 | 1/2017 | Bonner et al. |
| 9,616,002 B2 | 4/2017 | Gonzales et al. |
| 9,616,008 B2 | 4/2017 | Bhushan et al. |
| 9,617,459 B2 | 4/2017 | Van Engelen et al. |
| 9,550,597 B2 | 5/2017 | Konya et al. |
| 9,677,030 B2 | 6/2017 | Napolitano |
| 9,693,675 B2 | 7/2017 | Matta et al. |
| 9,796,914 B2 | 10/2017 | Shen et al. |
| 9,826,877 B2 | 11/2017 | DeMarco et al. |
| 9,840,660 B2 | 12/2017 | Chopade et al. |
| 9,862,916 B2 | 1/2018 | Van Engelen et al. |
| 9,884,137 B2 | 2/2018 | Kettlewell et al. |
| 10,100,269 B2 | 10/2018 | Fernandez-Prieto et al. |
| 10,199,269 B2 | 2/2019 | Chen et al. |
| 10,253,457 B2 | 4/2019 | Husband et al. |
| 10,266,792 B2 | 4/2019 | Sivik et al. |
| 10,266,793 B2 | 4/2019 | Labib et al. |
| 10,337,146 B2 | 7/2019 | Holtan et al. |
| 10,337,147 B2 | 7/2019 | Rouse et al. |
| 10,617,791 B2 | 4/2020 | Nunes et al. |
| 10,925,773 B2 | 2/2021 | Riesinger |
| 11,326,128 B2 | 5/2022 | Labib et al. |
| 11,345,878 B2 | 5/2022 | Labib et al. |
| 11,680,226 B2 | 6/2023 | Labib et al. |
| 2001/0011516 A1 | 8/2001 | Cantiani et al. |
| 2003/0121532 A1 | 7/2003 | Coughlin et al. |
| 2003/0191204 A1 | 10/2003 | Hermann et al. |
| 2003/0213501 A1 | 11/2003 | Thomson et al. |
| 2004/0000012 A1 | 1/2004 | Scarpello et al. |
| 2005/0137274 A1 | 6/2005 | Ko et al. |
| 2005/0201965 A1 | 9/2005 | Kuhlman et al. |
| 2005/0220727 A1 | 10/2005 | Lupia et al. |
| 2006/0020126 A1 | 1/2006 | Kopesky et al. |
| 2006/0032633 A1 | 2/2006 | Nguyen |
| 2006/0034782 A1 | 2/2006 | Brown et al. |
| 2006/0171913 A1 | 8/2006 | Schroder |
| 2006/0249265 A1 | 11/2006 | Scarpello et al. |
| 2007/0106013 A1 | 5/2007 | Adachhi et al. |
| 2007/0141095 A1 | 6/2007 | Simonnet |
| 2007/0151680 A1 | 7/2007 | Scarpello et al. |
| 2007/0199668 A1 | 8/2007 | Scarpello et al. |
| 2008/0082065 A1 | 4/2008 | Weerawarna et al. |
| 2008/0082067 A1 | 4/2008 | Weerawarna et al. |
| 2008/0108534 A1 | 5/2008 | Bernard et al. |
| 2008/0147026 A1 | 6/2008 | Qin et al. |
| 2009/0095324 A1 | 4/2009 | Crowther et al. |
| 2009/0269376 A1 | 10/2009 | Lundberg et al. |
| 2009/0306223 A1* | 12/2009 | Cai .................. A23L 29/262 514/769 |
| 2009/0324514 A1 | 12/2009 | Awad |
| 2010/0009891 A1 | 1/2010 | Canto et al. |
| 2010/0210501 A1 | 8/2010 | Caggioni et al. |
| 2010/0221294 A1 | 9/2010 | Kurek et al. |
| 2010/0247615 A1* | 9/2010 | Toreki .................. A61L 15/46 424/447 |
| 2010/0264364 A1 | 10/2010 | Wagner et al. |
| 2011/0262504 A1 | 10/2011 | Deleersnyder et al. |
| 2012/0090192 A1 | 4/2012 | Oevreboe et al. |
| 2012/0100193 A1 | 4/2012 | Nowak et al. |
| 2012/0100367 A1 | 4/2012 | Holtan et al. |
| 2012/0237576 A1 | 9/2012 | Gordon et al. |
| 2012/0267570 A1 | 10/2012 | Shi et al. |
| 2013/0029895 A1 | 1/2013 | Bettiol et al. |
| 2013/0072417 A1 | 3/2013 | Perez-Prat Vinuesa et al. |
| 2013/0098407 A1 | 4/2013 | Perlman et al. |
| 2013/0180679 A1 | 7/2013 | Laine et al. |
| 2013/0230609 A1 | 9/2013 | Modak et al. |
| 2013/0261208 A1 | 10/2013 | Borges De Couraca et al. |
| 2014/0000891 A1 | 1/2014 | Mahoney et al. |
| 2014/0128480 A1 | 5/2014 | Swazey et al. |
| 2014/0221948 A1* | 8/2014 | Riesinger .............. A61L 15/60 604/319 |
| 2014/0238444 A1 | 8/2014 | Arai |
| 2015/0031592 A1 | 1/2015 | Barreleiro et al. |
| 2015/0191681 A1 | 7/2015 | Gonzales et al. |
| 2015/0210957 A1 | 7/2015 | Napolitano |
| 2015/0210967 A1 | 7/2015 | Van Engelen et al. |
| 2015/0305819 A1 | 10/2015 | Krause |
| 2016/0222275 A1 | 8/2016 | Galindo et al. |
| 2016/0312298 A1 | 10/2016 | Ting et al. |
| 2016/0325318 A1 | 11/2016 | Tyrrell et al. |
| 2016/0331703 A1 | 11/2016 | Myntti |
| 2016/0332141 A1 | 11/2016 | Machida et al. |
| 2016/0346427 A1 | 12/2016 | Nunes et al. |
| 2016/0367102 A1 | 12/2016 | DeMarco et al. |
| 2017/0044468 A1 | 2/2017 | Gori et al. |

(56) References Cited

U.S. PATENT DOCUMENTS

| | | | |
|---|---|---|---|
| 2017/0121908 A1 | 5/2017 | Holtan et al. | |
| 2017/0183555 A1 | 6/2017 | Lillandt et al. | |
| 2017/0191003 A1 | 7/2017 | Fernandez-Prieto et al. | |
| 2017/0197071 A1* | 7/2017 | Gottenbos | A61K 8/0283 |
| 2018/0078484 A1 | 3/2018 | Blell et al. | |
| 2018/0094214 A1 | 4/2018 | Labib et al. | |
| 2019/0249115 A1 | 8/2019 | Labib et al. | |
| 2020/0270551 A1 | 8/2020 | Labib et al. | |
| 2021/0330557 A1 | 10/2021 | Labib et al. | |
| 2022/0396752 A1 | 12/2022 | Labib et al. | |

FOREIGN PATENT DOCUMENTS

| | | |
|---|---|---|
| CN | 1163748 A | 11/1997 |
| CN | 1994268 A | 7/2007 |
| CN | 103599000 B | 1/2016 |
| CN | 106691886 B | 4/2020 |
| EP | 0 198 094 A1 | 10/1986 |
| EP | 0 392 248 A1 | 10/1990 |
| EP | 0 845 495 A2 | 6/1998 |
| EP | 2 100 590 A1 | 9/2009 |
| EP | 3 081 209 A1 | 10/2016 |
| EP | 3 033 116 B1 | 4/2021 |
| JP | 2010-509462 A | 3/2010 |
| JP | 2011-505340 A | 2/2011 |
| JP | 2011-513507 A | 4/2011 |
| JP | 2014-521769 A | 8/2014 |
| JP | 2014-181247 A | 9/2014 |
| JP | 2015-508300 A | 3/2015 |
| JP | WO2013092633 | 3/2015 |
| JP | 2015-522014 A | 8/2015 |
| JP | 2016-527065 A | 9/2016 |
| KR | 10-0555300 B1 | 3/2006 |
| KR | 10-2009-0071717 A | 7/2009 |
| KR | 10-1035140 | 5/2011 |
| TW | I419708 B | 12/2013 |
| WO | WO 92/18151 A1 | 10/1992 |
| WO | WO 95/34275 A1 | 12/1995 |
| WO | WO 00/47628 A1 | 8/2000 |
| WO | WO 03/040284 A1 | 5/2003 |
| WO | WO 2006/008645 A2 | 1/2006 |
| WO | WO 2007/091942 A1 | 8/2007 |
| WO | WO 2008/109270 A1 | 9/2008 |
| WO | WO 2009/068841 A2 | 6/2009 |
| WO | WO 2009/101545 A1 | 8/2009 |
| WO | WO 2010/070354 A1 | 6/2010 |
| WO | WO 2012/040314 A1 | 3/2012 |
| WO | WO 2012/052306 A1 | 4/2012 |
| WO | WO 2012/065924 A1 | 5/2012 |
| WO | WO 2012/107648 A1 | 8/2012 |
| WO | WO 2013/009225 A1 | 1/2013 |
| WO | WO 2014/003776 A1 | 1/2014 |
| WO | WO 2014/075845 A1 | 5/2014 |
| WO | WO 2014/082951 A2 | 6/2014 |
| WO | WO 2014/088072 A1 | 6/2014 |
| WO | WO 2014/154348 A1 | 10/2014 |
| WO | WO 2015/022340 A1 | 2/2015 |
| WO | WO 2015/180844 A1 | 12/2015 |
| WO | WO 2016/086951 A1 | 6/2016 |
| WO | WO 2016/100822 A1 | 6/2016 |
| WO | WO 2016/166179 A1 | 10/2016 |
| WO | WO 2018/064284 A1 | 4/2018 |
| WO | WO 2019/195403 A1 | 10/2019 |

OTHER PUBLICATIONS

Adamcik et al., "Proteins Fibrils from a Polymer Physics Perspective," Macromolecules, vol. 45, pp. 1137-1150 (2012).
Alfa et al., "A novel polytetrafluoroethylene-channel model, which simulates low level of culturable bacteria in buildup biofilm after repeated endoscope reprocessing," Gastrointestinal Endoscopy, vol. 86, No. 3, pp. 442-451 (2017).
Au et al., "Behaviour of LAPONITE® gels: rheology, ageing, pH effect and phase state in the presence of dispersant," Chemical Engineering Research and Desing, vol. 101, pp. 65-73 (Sep. 2015).
Bolden et al., "The Clinical Effect of a Dentifrice Containing Triclosan and a Copolymer in a Sodium Fluoride/Silica Base on Plaque Formation And Gingivitis: A Six-Month Clinical Study," *J Clin Dent*, vol. 3, No. 4, pp. 125-131 (1992).
Bonfil et al., "The influence of gingival stimulation on recovery from human experimental gingivitis," Journal of Clinical Periodontology, vol. 12, pp. 828-836 (1985).
Bowen et al., Biology of *Streptococcus mutans*-Derived Gucosyltransferases: Role in Extracellular Matrix Formation of Cariogenic Biofilms, Caries Res, vol. 45, pp. 69-86 (2011).
de Oliveira et al., "Toothbrushing, inflammation and risk of cardiovascular disease: results from Scottish Health Survey," BMJ, doi: 10.1136/bmj.c2451, 340:c2451 (2010).
Chen et al., "Role of electrostatic interactions in cohesion of bacterial biofilms," Applied Microbiology and Biotechnology, vol. 59, pp. 718-720 (2002).
Chu et al., "Smart wormlike micelles," Chemical Society Reviews, vol. 42, pp. 7174-7203 (2013).
Cipriano et al., "Superabsorbent Hydrogels That Are Robust and Highly Stretchable," Macromolecules, vol. 47, pp. 4445-4452 (2014).
Cubells et al., "The Effect of a Triclosan/Copolymer/Fluoride Dentifrice on Plaque Formation and Gingivitis: A Six-Month Clinical Study," *J Clin Dent*, vol. 2, No. 3, pp. 63-69 (1991).
Dreiss, "Wormlike micelles: where do we stand? Recent developments, linear rheology and scattering techniques," Soft Matter, vol. 3, pp. 956-970 (2007).
Gallob et al., "Comparative Efficacy of a Soft Toothbrush with Tapered-tip Bristles and an ADA Reference Toothbrush on Established Gingivitis and Supragingival Plaque over a 12-Week Period," the Journal of Clinical Dentistry, vol. 27, No. 2, pp. 39-47 (2016).
Gaudino et al., "Adding salt to a surfactant solution: Linear rheological response of the resulting morphologies," Journal of Rheology, vol. 59, No. 6, pp. 1363-1375 (Nov./Dec. 2015).
George et al., Cellulose Nanocrystals: synthesis, functional properties, and applications. Nanotechnology, Science and Applications, vol. 8, pp. 47-54 (2015).
Gloag et al., "Viscoelastic properties of *Pseudomonas aeruginosa* variant biofilms," Scientific Reports, 8:9691 DOI:10.1038/s41598-018-28009-5 (2018).
Grabenstetter et al., "The measurement of the abrasion of human teeth by dentifrice abrasives: a test utilizing radioactive teeth," J Dent Res, vol. 37, No. 6, pp. 1060-1068 (Nov.-Dec. 1958).
Gusnaniar et al., "Transmission of Monospecies and Dual-Species Biofilms from Smooth to Nanopillared Surfaces," Appl. Environ. Microbiol., vol. 84, Issue 15, e01035-18, 11 pages (Aug. 2018).
Hammer et al., "Cross-Linked Conjugated Polymer Fibrils: Robust Nanowires from Functional Polythiophene Diblock Copolymers,"Chemistry of Materials, vol. 23, pp. 4250-4256 (2011).
Heydorn et al., "Quantification of biofilm structures by the novel computer program COMSTAT," Microbiology, vol. 146, pp. 2395-2407 (2000).
Jayakumar et al, "Role of Dentifrice in plaque removal: a clinical trial," Indian Journal of Dental Research, vol. 21, Issue 2, pp. 213-217 (Apr.-Jun. 2010)
Kerr et al., "Chemical Composition and In-vitro Digestibility of Thermochemically Treated Peanut Hulls," J. Sci. Food Agric., vol. 37, pp. 632-636 (1986).
Khosravi et al., "Use of an oxygen planar optode to assess the effect of high velocity microsprays on oxygen penetration in a human dental biofilms in-vitro," BMC Oral Health 20:230 https://doi.org/10.1186/s12903-020-01217-0 (2020).
Kolenbrander et al., "Adhere Today, Here Tomorrow: Oral Bacterial Adherence," Journal of Bacteriology, vol. 175, No. 11, pp. 3247-3252 (Jun. 1993).
Koo et al., "Exopolysaccharides Produced by *Streptococcus mutans* Glucosyltransferases Modulate the Establishment of Microcolonies within Multispecies Biofilms," Journal of Bacteriology, vol. 192, No. 12, pp. 3024-3032 (Jun. 2010).
Lewis et al., "Interaction between toothbrushes and toothpaste abrasive particles in simulated tooth cleaning," Wear, vol. 257, No. 3-4, pp. 368-376 (2004).

(56) References Cited

OTHER PUBLICATIONS

Mateu et al., "A Clinical Investigation of the Efficacy of Two Dentifrices for Controlling Established Supragingival Plaque and Gingivitis," *J Clin Dent*, vol. 19, No. 3, pp. 85-94 (2008).
Mignon et al, "Superabsorbent polymers: a review on the characteristics and applications of synthetic, polysaccharide-based semi-synthetic and 'smart' derivatives," European Polymer Journal, vol. 117, pp. 165-178 (2019).
Morozova, "Methylcellulose fibrils: a mini review," Polymer International, vol. 69, No. 2, pp. 125-130 (2020).
Palmer et al., "*Streptococcus mutans* yidC1 and yidC2 Impact Cell Envelope Biogenesis, the Biofilm Matrix, and Biofilm Biophysical Properties," Journal of Bacteriology, vol. 201, Issue 1, e00396-18, https://doi.org/10.1128/JB.00396-18, (Jan. 2019)
Paraskevas et al., Additional Effect of Dentifrices on the Instant Efficacy of Toothbrushing, J Periodontology, vol. 77, No. 9, pp. 1522-1527 (2006).
Perazzo et al, "Emulsions in porous media: From single droplet behavior to applications for oil recovery," Advances in Colloid and Interface Sciences, vol. 256, pp. 305-325 (2018).
Perazzo et al., "Flow-induced gelation of microfiber suspensions," Proceedings of the National Academy of Sciences, 114(41):201710927, DOI:10.1073/pnas.1710927114, E8557-E8564 (2017).
Pointner et al., "Composition of corncobs as a substrate for fermentations of biofuels," Agronomy Research, vol. 12, No. 2, pp. 391-396 (2014).
Rizvi et al., "Dispersed polypropylene fibrils improve the foaming ability of a polyethylene matrix," Polymer, vol. 55, No. 16, pp. 4199-4205 (2014).
Rmaile et al., "Microbial tribology and disruption of dental plaque bacterial biofilms," Wear, vol. 306, Issues 1-2, pp. 276-284 (Aug. 30, 2013).
Schemehorn et al., "Abrasion, Polishing, and Stain Removal Characteristics of Various Commercial Dentifrices In Vitro," J Clin Dent, vol. 22, No. 11, pp. 11-18 (2011).
Sharma et al., "The Clinical Effects on Plaque and Gingivitis Over Three-Months Use of Four Complex-Design Manual Toothbrushes," *J Clin Dent*, vol. 5, No. 4, pp. 114-118 (1994).
Stoodley et al., "Structural Deformation of Bacterial Biofilms Caused by Short-Term Fluctuations in Fluid Shear: An in Situ Investigation of Biofilm Rheology," Biotechnololgy and Bioengineering, vol. 65, No. 1, pp. 83-92 (Oct. 5, 1999).

Tavakolian, et al., "A Review on Surface-Functionalized Antibacterial Materials," Nano-Micro Lett. 12, 73 (2020). https://doi.org/10.1007/s40820-020-0408-4.
Valkenburg et al., "Does Dentifrice Use Help to Remove Plaque? a Systematic Review," Journal of Clinical Periodontology, vol. 43, pp. 1050-1058, doi: 10.1111/jcpe.12615 (2016).
Van der Rijt et al., "Micromechanical Testing of Individual Collagen Fibrils," Macromolecular Bioscience, vol. 6, pp. 697-702 (2006).
Verkaik et al., "Oral biofilm models for mechanical plaque removal," Clin. Oral. Invest., vol. 14, pp. 403-409 (2010).
Vinogradov et al., "Rheology of biofilms formed from the dental plaque pathogen *Streptococcus mutans*," Biofilms, vol. 1, pp. 49-56 (2004).
Volpatti et al., "Polymer Physics Inspired Approaches for the Study of the Mechanical Properties of Amyloid Fibrils," Journal of Polymer Science, Part B: Polymer Physics, vol. 52, pp. 281-292 (2014).
Walsh et al., "Fluoride toothpastes of Different Concentrations for Preventing Dental Caries (Review),"Cochrane Database of Systematic Reviews, Issue 3. Art. No. CD007868 DOI: 10.1002/14651858. CD007868.pub3 (2019).
Yang et al., "Structural and Ecofriendly Holocellulose Materials from Wood: Microscale Fibers and Nanoscale Fibrils," Advanced Materials, 2001118 (2020).
Yu et al., "Scalable manufacturing of biomimetic moldable hydrogels for industrial applications," PNAS, vol. 113, No. 50, pp. 14255-14260 (Dec. 13, 2016).
Yumoto et al., "The Pathogenic Factors from Oral Streptococci for Systemic Diseases," Int. J. Mol. Sci., 2019, 20, 4571; doi:10.3390/ijms20184571, pp. 1-18.
Zanatta et al., "Supragingival Plaque Removal with and without Dentifrice: a Randomized Controlled Clinical Trial," Braz. Dent J., vol. 23, No. 3, pp. 235-240 (2012).
Exhibit A—allowed claims U.S. Appl. No. 16/279,443.
Exhibit B—allowed claims U.S. Appl. No. 16/461,536.
Exhibit C—pending claims U.S. Appl. No. 17/225,049.
Cheng et al., "Water Retention Value Measurements of Cellulosic Materials Using a Centrifuge Technique," BioResources, vol. 5, No. 3, pp. 1945-1954 (2010).
Homma et al., "Effects of carboxyl-group counter-ions on biodegradation behaviors of TEMPO-oxidized cellulose fibers and nanofibril films," Cellulose, vol. 20, pp. 2505-2515 (2013).
Turbak, "Birth of Nanocellulose," www.naylornetwork.com/ppi-otw/articles/?aid=150993&issuel 0=22333, TAPPI, 4 pages (2011).
Exhibit A—the pending claims U.S. Appl. No. 17/737,654.
Exhibit B—the pending claims U.S. Appl. No. 17/751,186.

* cited by examiner

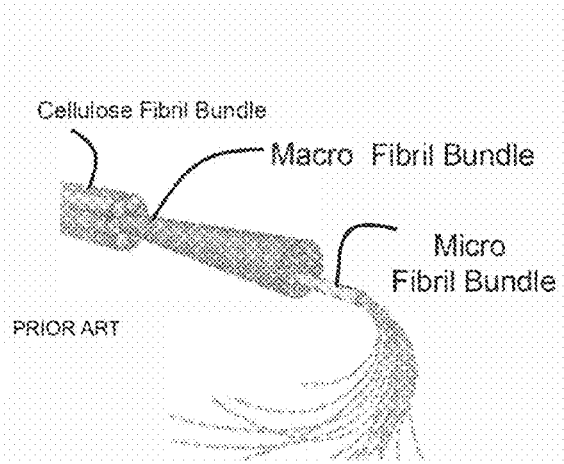
Figure 1A
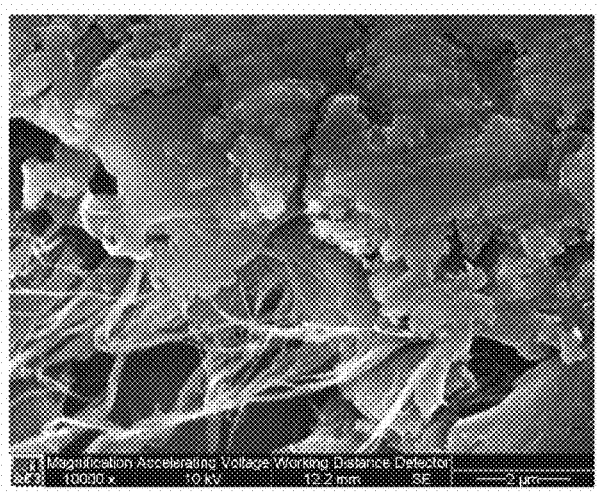
Figure 1B: Fibrils of MFC (lower left) entangled with biofilm (upper right)
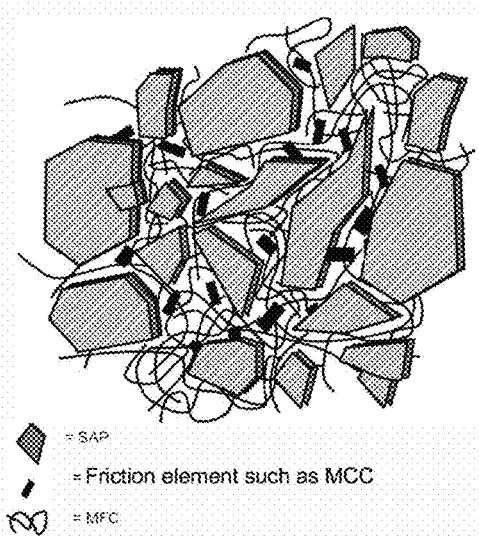
Figure 1C
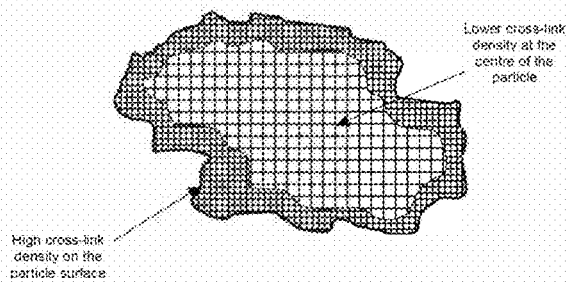
Figure 1D

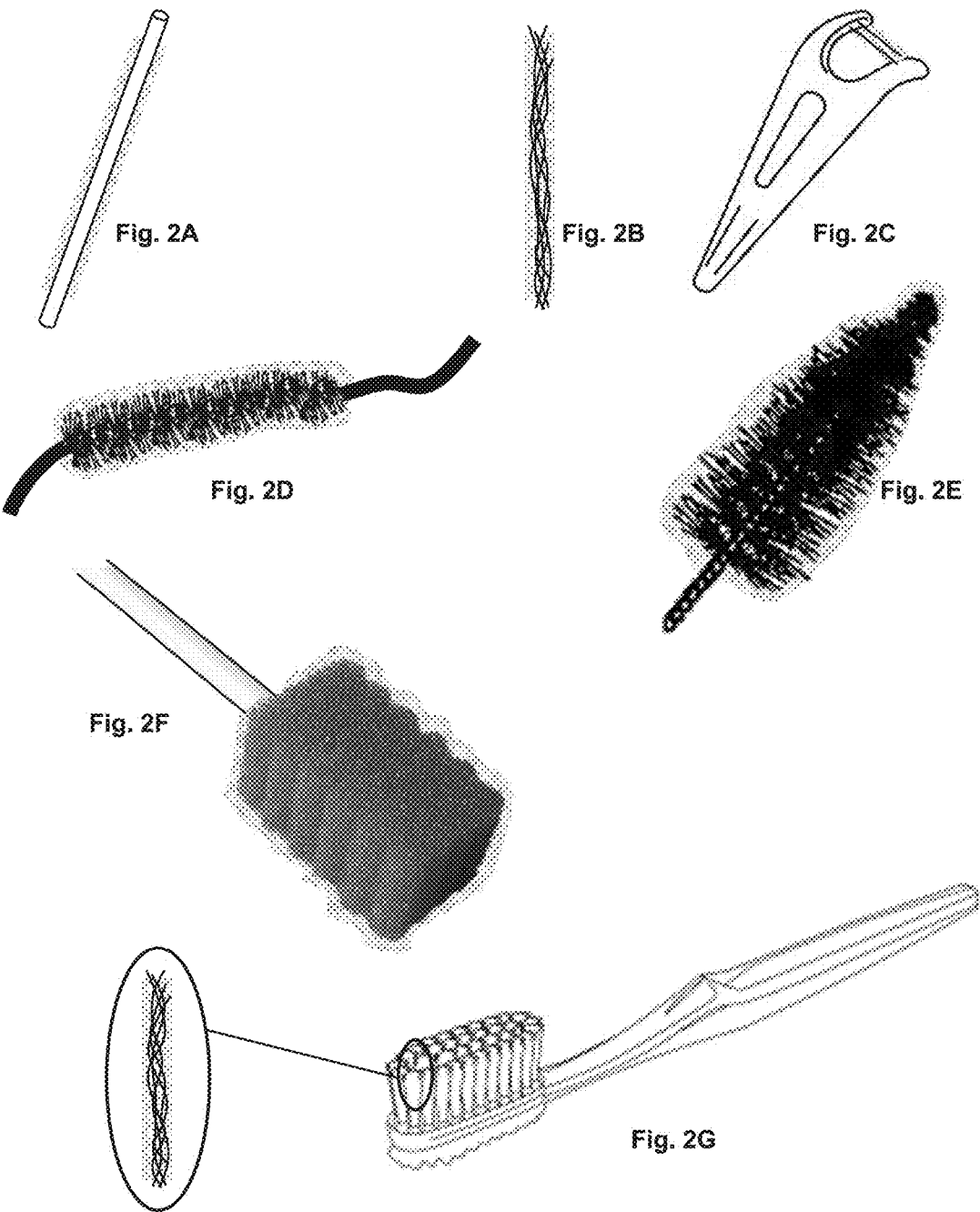

A. Schematic depicting flow of commercial toothpaste in IP Space

3 Min. Cleaning
Q = 45 ml/m  0.01 CMC NCK
Q = 43 ml/m  NCK (3mm)
Q =  0.1% CMC NCK
Q = 77 ml/in  NCl dd Cleaned 2 min
Q = 146/3   113 LV18
   NCl
Q = 77 ml/m
Figure 7

Hydroxyapatite surface cleaned with Colgate (left); cleaned with NanoClean (right)

Hydroxyapatite surface cleaned with Colgate (left); cleaned with NanoClean (right)

Shear stress and viscosity for 50% concentration

Tribology with glass ball on Teflon pins

Tribology with glass ball on PDMS pins

ORAL CAVITY CLEANING COMPOSITION METHOD AND APPARATUS

CROSS-REFERENCE TO RELATED APPLICATIONS

This patent disclosure claims the benefit, to the extent appropriate, of U.S. Provisional patent application Ser. No. 62/910,049, filed Oct. 3, 2019, and U.S. Provisional patent application Ser. No. 62/913,565, filed Oct. 10, 2019. U.S. Provisional patent application Ser. Nos. 62/910,049 and 62/913,565 are incorporated herein by reference in their entireties.

The following patent application disclosures are incorporated herein by reference: Provisional Patent Application U.S. Ser. No. 62/402,394, filed Sep. 30, 2016, including its appendix; Provisional Patent Application U.S. Ser. No. 62/563,975, filed Sep. 27, 2017 (NOVA003P2), including its appendices; Nonprovisional patent application U.S. Ser. No. 15/718,325, filed Sep. 28, 2017, which published as US20180094214A1; PCT patent application PCT/US17/53925, filed Sep. 28, 2017, which published as WO2018064284A1; Provisional Patent Application U.S. Ser. No. 62/652,079, filed Apr. 3, 2018; Provisional Patent Application U.S. Ser. No. 62/692,082 filed Jun. 29, 2018; Provisional Patent Application U.S. Ser. No. 62/692,082 filed Jun. 29, 2018; Provisional Patent Application U.S. Ser. No. 62/822,432 filed Mar. 22 2019; Provisional Patent Application U.S. Serial No. U.S. Ser. No. 62/828,134 filed Apr. 2 2019; PCT/US2019/025558, filed Apr. 3, 2019 (which in turn claims the benefit of some of the above-listed provisionals) and patent application U.S. Ser. No. 16/461,536 filed May 16, 2019.

FIELD OF THE INVENTION

Embodiments of the invention include compositions, methods, and apparatuses suitable for use in cleaning teeth and removing food particles, plaque biofilms, tartar, calcium deposits, and stains from teeth, and for promoting oral health and hygiene.

BACKGROUND OF THE INVENTION

Biofilm is a structure scaffolded with extracellular polysaccharide substances (EPS), created by microorganisms, in which the microorganisms are embedded. Biofilm can be difficult to clean or remove, and dental plaque is a form of biofilm. Dental plaque biofilm is a slightly viscous liquid film, which forms on teeth between brushings. The presence of plaque on teeth is undesirable, because the bacteria, which grow in plaque biofilm, are responsible for oral diseases, such as caries and gingivitis. Oral plaque also is believed to be associated with other diseases such as Alzheimer's Disease and cardiovascular disease.

While many dentifrices claim reductions in plaque and gingivitis, most dentifrices do not promote or assist the physical removal of plaque from teeth. Indeed, for such dentifrices, physical removal of plaque is believed to be mostly achieved by the toothbrush bristles themselves interacting with the tooth surface during the physical act of brushing. One reason for this ineffectiveness is that most toothpastes include lubricating ingredients, such as humectants, surfactants, rheology modifiers that are lubricious and reduce the friction coefficient at the tooth surface. As of the inventors' current knowledge, the only commercially available toothpaste that is proven effective in physically enhancing plaque removal during brushing is one toothpaste containing a large concentration of particles of sodium bicarbonate (baking soda); however such toothpaste is salty and difficult to use among other limitation.

After a conventional toothpaste or dentifrice is dispensed and is being used, the toothpaste or dentifrice generally is exposed in the mouth to liquids such as saliva and water, and becomes diluted. A composition that may have started out being quite viscous becomes less viscous after dilution. Also, the concentration of whatever is in the toothpaste is reduced. Many toothpastes, even in their as-manufactured full-strength composition, are actually not very effective at removing biofilm. After dilution, the composition becomes even less effective than it was at full strength. In regard to the toothpaste that is heavily loaded with particles of sodium bicarbonate [baking soda], the performance of that toothpaste decreases rapidly with dilution.

Development has been performed in commonly-assigned U.S. Pat. No. 10,266,793 of a composition that comprises a network of fibrillated material in a liquid vehicle, and that can create high shear stress and has less lubricity than many other cleaning compositions. The composition described in that patent has been suitable for cleaning endoscope channels and other surfaces and geometries. However, because of the presence of ingredients that would be undesirable in toothpaste, and because of the absence of ingredients that would be desirable in toothpaste, such composition was not optimized for dental uses. Importantly, the composition intended for use in endoscopes never had to experience dilution and so it was not optimized for performance after experiencing dilution as experienced in the mouth during tooth brushing. The composition of U.S. Pat. No. 10,266,793 also is not specifically designed for use in the oral cavity because it is not likely to remove stains from teeth.

Yet another trend in toothpastes concerns the use of antimicrobial substances to combat plaque. The antimicrobial substance triclosan has recently been banned from toothpastes due to its potential to cause antimicrobial-resistant strains of bacteria, and the use of stannous fluoride, which happens to also have antimicrobial properties, has turned out to be less than popular in the market. Removal of plaque from teeth by physical means would address these issues concerning chemical antimicrobial substances.

Accordingly, the development of a toothpaste which promotes improved physical removal of plaque biofilm from teeth would be highly desirable.

SUMMARY OF THE INVENTION

An embodiment of the invention may comprise a cleaning composition for cleaning teeth, the composition includes: (a) a friction component comprising a mixture of: (i) fibrillated polymer comprising thicker fibrils and thinner fibrils branched from the thicker fibrils, wherein the thicker fibrils have a diameter of about 250 nm to about 20,000 nm, and (ii) friction elements having at least one dimension that is larger than 25 microns and an aspect ratio of larger than 2, the aspect ratio being a ratio of maximum dimension to minimum dimension, wherein the friction elements are entangled in the thicker fibrils and the thinner fibrils of the fibrillated polymer; (b) a dentifrice additive including at least one component from the following list of optional or alternative components: a source of fluoride ions; abrasive particles having a hardness of less than 3 on a Mohs Hardness Scale and a size less than 200 microns; a stain remover; a whitener; a surfactant for assisting in loosening contaminants from a tooth surface; an antiplaque agent; a tartar control agent; a tooth sensitivity agent; and a water activity modifier; a flavorant; a sweetener; or a colorant; and (c) a sufficient amount of water as a carrier so that the composition has viscoelastic fluid properties. The composition can be provided as a composition that satisfies a plaque removal test wherein said plaque removal test comprises providing said composition at a first concentration and removing biofilm from a tube and providing said composition at a second concentration that is half the first concentration by dilution with water and removing said biofilm from said tube, wherein said tube is coated internally with said biofilm and said cleaning is measured by flowing the respective compositions through said tubes at a pressure drop per unit length of 1.9 psi/foot for a period of 3 minutes. Alternatively or in addition, said composition can be provided that satisfies an alternative plaque removal test where said composition provided a the first concentration is able to clean at least 50% of plaque from a tooth in less than 2 minutes, and wherein said composition provided at a second concentration, when diluted by water to half of the first concentration, is also able to clean at least 50% of said plaque from said tooth, in less than 2 minutes.

In an embodiment of the invention, an orally acceptable composition based on polymeric thickeners or a mixture of polymer thickeners and crosslinking particles or agents can be made to satisfy the rheological and tribological requirements of the present invention such as to withstand dilution by water or saliva to 50% or 25% of undiluted preparation and remove plaque from teeth by creating sufficient shear stresses and friction forces sufficient to overcome the biofilm plaque deposited on teeth or in between teeth, and this can be accomplished without the use of fibrillated material.

BRIEF DESCRIPTION OF THE DRAWINGS

Embodiments of the invention are further illustrated, but are in no way limited, by the following illustrations.

FIG. 1A illustrates shows a schematic of the structure of cellulose fibril bundles.

FIG. 1B is a SEM (Scanning Electron Microscope) image of a composition of an embodiment of the invention, entangled with a piece of biofilm.

FIG. 1C is a schematic of a mosaic of Particles of SuperAbsorbent Polymer, Minute Fibrils and solid particles.

FIG. 1D is a schematic of a particle of SuperAbsorbent Polymer that is Surface Cross-linked.

FIG. 2A illustrates a monofilament dental floss or dental tape containing a composition of an embodiment of the invention.

FIG. 2B illustrates a multifilament dental floss or dental tape containing a composition of an embodiment of the invention.

FIG. 2C illustrates a floss holder used with an embodiment of the invention.

FIG. 2D illustrates a flexible interproximal brush of an embodiment of the invention.

FIG. 2E illustrates a stiff interproximal brush of an embodiment of the invention.

FIG. 2F illustrates a toothbrush of an embodiment of the invention.

FIG. 2G illustrates a toothbrush of an embodiment of the invention, having a particular structure of individual bristles.

FIG. 7 shows results of cleaning internal surfaces of transparent tubes, using a composition of an embodiment of the invention which either did or did not contain carboxymethylcellulose.

DETAILED DESCRIPTION OF THE INVENTION

Figure 3A:
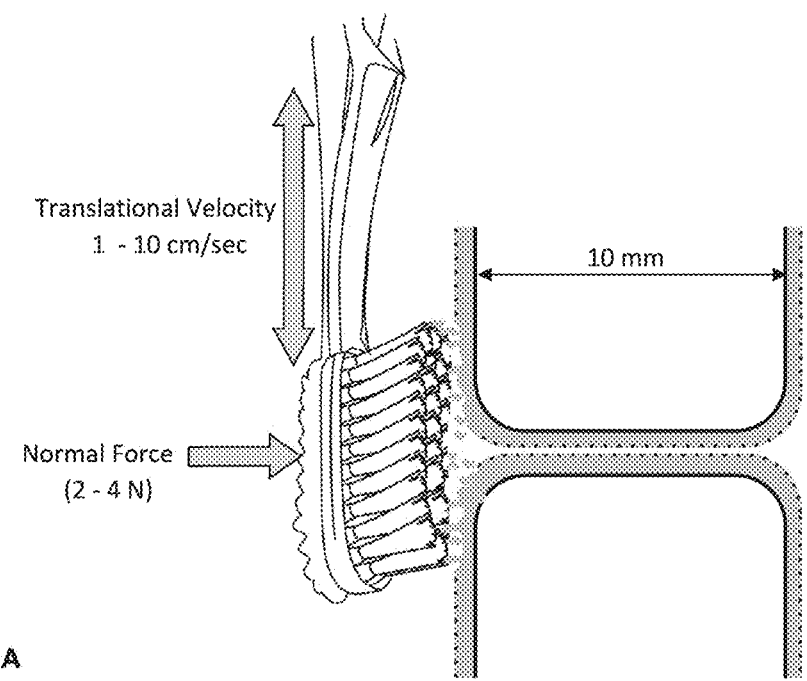
FIG. 3A is an illustration of a conventional toothbrush applying a conventional toothpaste to a tooth and pushing conventional toothpaste into the interproximal space.

Compositions of embodiments of the invention are designed to provide a viscoelastic toothpaste formulation with increased non-damaging, i.e. "soft" abrasion. Compositions of embodiments of the invention comprise a particular design of fibers and particles, and are effective on fluid flow across the tooth surface. As an example, an aqueous-based viscoelastic composition of NanoClean tooth cleaner (NCTP) containing microfibrillated cellulose in water is effective at removing biofilm from tooth surfaces. It has been demonstrated in vitro that plaque removal can be achieved, by physical processes, using a specially designed nano-fibrous cellulose ingredient to physically detach the biofilm from tooth surfaces. The following describes generalized categories of ingredients typically found in typical toothpastes and in embodiments of the invention, along with approximate ranges.

Embodiments of the compositions comprise fibers or fibrils based on natural or synthetic microfibrillated or fibrillated cellulose or other forms of polysaccharides or other non-cellulosic or non-cellulosic polymers which form a 3-D entangled network structure. In embodiments of the invention, fibrils may branch from other structures. Embodiments of the compositions are that they are viscoelastic and have a yield stress and have an elastic modulus or storage modulus greater than values described herein. It has been found that when these compositions are made to flow over a surface, they effectively remove even highly challenging biofilms, in contrast to commercial toothpastes, which were found to be ineffective when used under similar flow conditions. Embodiments of the compositions, when optimized, are expected to significantly improve oral hygiene and reduce gingivitis, tooth decay and tooth loss. It is believed that the operating mechanism of a network of fibrillated material is not present in conventional toothpastes.

It can be understood that many commercial toothpastes contain at least one substance that has a property of being lubricious or decrease the friction coefficient when applied to surface under some normal forces. In fact, sometimes the lubricious substance is included for the express purpose of its lubricity, in order to improve the dispensing action of the toothpaste or the "feel" of the toothpaste in the mouth. Sometimes such a substance is included for some other property such as water retention or as a binder/thickener or rheology modifier, but the substance has an inherently lubricious nature. In regard to surfactants, surfactants have a useful purpose in toothpaste such as to help loosen contaminants in general, of which specific examples are biofilm and plaque. However, in some toothpastes the surfactant concentration is quite large, and many surfactants are lubricious to at least some extent. Some surfactants are more lubricious than other surfactants. For example, in many existing toothpastes glycerol is present, and it is a substance that acts in a highly lubricious manner. CMC (carboxymethyl cellulose), or sodium salt of CMC, which is present as the main binder/thickener in many toothpastes at ~2%, or carrageenan or xanthan gum or carbopol, also creates lubricity. Specific surfactants are discussed elsewhere herein.

In embodiments of the invention, it is believed that the mode of operation includes a scraping or friction action of solid components against the biofilm or plaque, and it further is believed that for this goal, friction is desirable and lubrication is particularly detrimental in removing plaques from teeth. Embodiments of the invention may be characterized by an avoidance of certain ingredients such as lubricious substances or by limiting their concentration to less than certain values. This detriment is because a user of a tooth cleaning device typically has only so much patience, so that the compositions of the invention can be favorably adjusted to be effective given a limited amount number of passes over the teeth. Friction is desirable in regard to the motion of fibers and other solids past each other within the composition as the composition flows or moves, and more particularly motion of solids against or past the biofilm and plaque that is being cleaned. In embodiments of the invention, it is not required that every lubricious substance be totally excluded, but it is desirable, in embodiments of the invention, that the identity and concentration of such substances be controlled. The combination of high shear stress and frictional forces is the key parameters responsible for removing plaques from teeth by the inventive composition.

In embodiments of the invention, the Minute Fibrils themselves have a substantial water holding capability. In embodiments of the invention, it is possible to achieve water retention in the Minute Fibrils without contributing significantly to lubricious conditions. In other embodiments of the invention, it is also possible to achieve water retention in the particles of SuperAbsorbent Polymer without contributing significantly to lubricious conditions, especially if the particles of SuperAbsorbent Polymer have surface cross-linking. It is further possible to a small extent that friction elements contribute to water holding capability. In embodiments of the invention, it is possible to include a surfactant to achieve the cleaning assistance of surfactants, but the surfactant can be of an appropriate nature and at an appropriately small concentration so as not to create undesirably lubricious conditions. It is found that some surfactants, in some concentrations, promote an undesirable lubricious situation, while other surfactants, in certain concentrations, do not have that effect or do not have as much of that effect.

In embodiments of the invention, there can also be avoidance of ingredients for reasons other than lubricity. For a dentifrice there can also be biocompatibility and regulatory considerations, given that a dentifrice is exposed to mucous oral tissues and can be swallowed. For example, certain chelating agents that might be useful in a general-purpose cleaning composition are excluded. An example of such a substance is EDTA or organic solvents. Also, among the large number of known surfactants, some surfactants have known cytotoxic effects and are therefore to be excluded.

Dilution tolerance refers to the ability of a composition to be effective in removing biofilm over a range of dilutions. For example, an embodiment of the invention may have a nominal (undiluted) formulation that is effective at removing dental plaque, and it also may still be effective at removing plaque even when it is diluted during application in the oral cavity. This can be affected by the presence and by the characteristics of the network and by the initial concentrations of various substances.

It is believed (although it is not wished to be limited to this explanation) that part of the mechanism or principle by which embodiments of the invention remove biofilm is that the Minute Fibrils form a network that entraps particles in the composition and drags those particles along with flow of the composition, and causes some of the particles some of the time to scrape against or create localized shear stresses or interact with the surface being cleaned. Some of those particles might form an attachment with the biofilm and pull it away from the surface being cleaned. The particles can be any or some of ingredients such as friction elements, abrasive particles and SAP particles or their combination.

It is believed that the water retention capability of SAP may contribute to the ability of a formulation of embodiments of the invention to be effective over a wide range of dilutions, in the sense that the SAP particles may absorb at least some of the newly introduced water or saliva and prevent the newly introduced water or saliva from deteriorating the concentration or performance of other ingredients of the composition. It also is believed that even if at least some of newly introduced water or saliva remains outside the SAP particles, it may dilute certain concentrations while still leaving the network of Minute Fibrils relatively intact, and leaving various particles still entangled in the network. It is believed that these effects may contribute to the ability of compositions of embodiments of the invention to be effective at biofilm removal even over a wide range of dilutions. However, it is not wished to be limited to these explanations. This is in contrast to the behavior of known commercial toothpastes, whose biofilm removal capability (if any) decreases rapidly when the toothpaste is diluted from its manufactured formulation to form liquid slurries which are not able to remove biofilm as described elsewhere herein.

Embodiments of the invention may comprise any or some or all of the categories of ingredients listed herein, in any combination, while certain compositions of embodiments of the invention also may specifically lack or avoid or minimize the concentration of certain other described ingredients. It is not necessary that all of the ingredients or categories of ingredients listed herein be included in any particular embodiment of the invention.

Fibrillated Material. Embodiments of the invention comprise a microfibrillated material that may form a three-dimensional network. In embodiments, the microfibrillated material may comprise cellulose. Cellulose is a polysaccharide that is created by plants, and also is created by bacteria or other organisms in including fungi. The process to produce MFC from plant cellulose may be primarily a mechanical process, or alternatively it could involve enzymatic and chemical processing. Also MFC can be synthesized by processes using microorganisms. In embodiments, the MFC is made on a commercial scale from Norwegian Spruce or from birch trees or other soft or hand wood tree species without limitation by a purely mechanical process without chemicals. A version of it is approved by the US FDA as a food ingredient. Alternatively, the process of making the MFC can also include enzymes and may include both mechanical and chemical processes. The MFC may also be made from wood pulp of any kind whether bleached or made by mechanical pulp processes. The fibrillated materials can be surface modified by physical means such as adsorption or can be chemically modified to introduce special functional groups to the surface of the fibers and fibrils. The MFC may be functionalized such as by oxidation as by the TEMPO process or by other chemical reactions including amidation, amination, hydrophobization or the like. Due to its interconnected entangled microstructure, MFC does not shed fibers, fibrils or particles when diluted in water as can occur during brushing, rinsing or cleaning. There are versions of MFC which are approved as GRAS (Generally Regarded As Safe) by FDA and can be used as food ingredients. Due to its interconnected entangled microstructure, MFC does not shed fibers or particles when diluted in water. The 3D network of the inventive composition made by mixing MFC with water under shear forms strong physical entanglements that are difficult to unravel with dilution and this may be a reason for their dilution tolerance. This is contrast with commercial toothpastes made with polymeric thickener which readily fall apart and disassemble into slurries with the slightest dilution.

The MFC can be of bacterial or microorganisms origin, specifically bacterial cellulose may provide biocompatibility fibrillated material that may be used alone or mixed with other fiber-based materials to form the 3D network of the present invention.

Polysaccharides other than cellulose are also possible materials. As yet another alternative, the fibrillated material can be also non-cellulosic such as those made from synthetic or made polymers such as flocked nylon or polyester, acrylic or other polymers. The fibrillated materials may be made by the Lyocell process where fibers are spun from cellulose-based polymers or other synthetic polymer materials such as those produced by the Engineered Fiber Technology Company (Shelton, Conn., USA).

In embodiments, the Minute Fibrils form an entangled network structure, the Minute Fibrils comprising thicker fibrils, from which branch thinner fibrils. The network may be effective to contribute to rheological properties described herein. The network contributing to effectiveness in removing dental plaque. In embodiments, the thicker fibrils may have a diameter from about 250 to about 20,000 nm, the thinner fibrils may contribute to the entangled network structure. These dimensions may be tailored depending on the degree of fibrillation as dictated by the mechanical energy used to fibrillate the source fibers, for example the number of passes through the microfluidizer machine as is known in the art of making micro- and nano fibrillated cellulose.

This class of MFC can be made from any of various types of wood or plants. MFC can be of plant origin such as that made by Borregaard (Sarpsborg, Norway) or Weidmann Fiber Technology (Rapperswil-Jona, Switzerland). The Borregaard material, which is sold under Tradename "Exilva," is made from Norwegian Spruce. The Weidmann material is made from Swiss Birch. It may be preferable to process the wood to form MFC using mechanical forces only, without the use of chemicals. Some other acceptable processes for making MFC may include enzymes or chemical compounds that can be washed out after processing. The desirable MFC may have a high degree of fibrillation and high water holding capacity from 50 to 150 g/g and average mean particle size from 20 to 70 um. The size distribution may have particles up to 100 um or 200 um or even close to 1 mm. The surface area, as measured according to BET (Brunauer-Emmett-Teller) theory, may be from 50 m2/g to 300 m2/g or even 500 m2/g. The viscosity of a 2% by weight concentration in water may be from 10,000 to 50,000 mPa-s when measured with a Brookfield viscometer with a V73 spindle at 10 rpm after 5 minutes. The material is not limited by species of tree.

Friction elements. In an embodiment of the invention, the composition may include friction elements. Friction can be created by the fibers and fibrils of the fibrillated material or from intentionally added friction elements or particles such as microcrystalline cellulose (MCC), silica, calcium carbonate, or other organic or inorganic particles. MCC or other friction elements may contribute to plaque removal by the MFC-based network composition. MCC can be present in the form of silicified MicroCrystalline Cellulose (SMCC). Still other friction elements than can be used include both organic particles and inorganic particles irrespective of their shape and sizes. In an embodiment of the invention, the friction elements can be entangled in the network created by the Minute Fibrils. The friction elements are believed to contribute to plaque removal by interacting with plaque, such as by scraping plaque.

Friction elements may be elongated or irregular shape. Friction elements may have at least one dimension that is larger than 25 microns or larger than 50 microns (average). The size could be up to 200 microns. Friction elements may have an aspect ratio (ratio of maximum dimension to minimum dimension) that is larger than 2 or larger than 3. In embodiments of the invention, the concentration (w/w) of friction elements may be at least as large as the concentration (w/w) of Minute Fibrils, or may be at least half the concentration (w/w) of Minute Fibrils, or may be 0.2% (w/w) or more, or 0.5% or more, or 0.6% or more. In some embodiments, they are 1.2% (w/w) or less. In some cases, friction elements may included at 5% or 10% to further modify the elastic modulus of stiffness of the fibrillated network.

MCC is known to be included in some conventional commercial toothpastes, but it is believed that in those conventional commercial toothpastes the MCC is in the form of very small particles such as smaller than 25 microns or smaller than 50 microns or even can in the form of what is referred to as colloidal MCC such as 3 or 4 microns or even less, and it is at small concentration, and is believed to be used as a rheology modifier or as a filler. It is believed that in the commercial toothpastes, which are based on polymeric thickeners such as CMC, the MCC is unlikely to provide a scraping or biofilm removal effect, because of small particle size, the effect of dilution by water and saliva and because of the lubricating effect of CMC.

Additional Examples of Both Fibrillated Material and Particles, Fibers and Fibrils The composition may comprise one or more natural or synthetic, non-scratching, insoluble, particles, fibers and fibrils, which may be polysaccharide. A useful particulate material is a non-fibrillated insoluble micro-crystalline cellulose (MCC), which has been shown to synergize with MFC in displacing plaque biofilm during brushing.

Additional insoluble cellulosic materials which can be used are ground peanut shells, consisting primarily of cellulose and hemicellulose polysaccharides with some lignin (reference: Kerr J I, Windham W R, Woodward J H and Benner R: Chemical Composition and In-vitro Digestibility of Thermochemically Treated Peanut Hulls. *J. Sci. Food Agric.* 1986; 37: 632-636) are also useful in the enhancement of plaque-biofilm removal. Pulverized corn cobs, which comprise mixtures of cellulose, hemicellulose and lignin can also be used (reference: Pointner M, Kuttner P, Obrlik T et al: Composition of corncobs as a substrate for fermentations of biofuels. *Agronomy Research* 2014; 12(2): 391-396). Ramie is another example of a natural material which provides useful particulate fibers, which can be extracted from the inner bark phloem of ramie plant stems and degummed. Useful fibrous materials can also be obtained from Jute, the Java tree, flax and abaca fiber and other sources.

Without being limited by possible specific modes of action, it is proposed that alone or in combination with others, these polysaccharide particles form 3-D entangled network structures when added to aqueous carriers. The resulting compositions are viscoelastic and have a yield stress more than 10 Pa and have an elastic modulus or storage modulus greater than 1000 Pa and preferably higher. Hence, one of the functions of these materials is to modify the tribology and better direct the brushing forces through the dentifrice to achieve appropriate values of these parameters. As a result, It has been found that when compositions of embodiments of the invention are driven by the toothbrush or applicator over the surface of the teeth, the "friction elements" physically remove highly challenging biofilms from the surfaces being cleaned. This contrasts with most commercial toothpastes, which are generally found to be ineffective in physically increasing removal of plaque biofilm. Another aspect of modifying the dentifrice tribology is to access tight spaces on and between the teeth where a normal toothbrush or conventional toothpaste cannot reach. We also believe that one of the advantages of using natural particulate polysaccharides is that they provide a surface to which plaque biofilm can attach and as a result help their removal when the dentifrice is expectorated after brushing.

These characteristics of the compositions, whether their geometry is fibrous or particulate or something else, significantly improve the physical displacement of oral biofilm, food residues and other undesirable materials from teeth and result in reduced gingivitis, less tooth decay and less tooth loss and hence better oral health.

Abrasive particles. In embodiments of the invention, the composition can include abrasive particles. The term abrasive particles, as used herein, may or may not overlap with the friction elements (such as MCC) that are described elsewhere herein. "Abrasive particles" as used herein is a term for particles that are intended to remove stains from the surfaces of teeth. Such particles typically have hardness less than 3 on the Mohs Hardness Scale, because such hardness is sufficient to remove stain while not being so hard as to damage tooth enamel or dentin. Their hardness may be greater than 2 on the Mohs Hardness Scale. Such particles typically have dimensions in the range of about 15-about 30 microns average diameter, or more generally 5 microns to 50 microns. Such particles may be spherical or not greatly elongated in shape, or may be irregular. Examples of the composition of such particles include: amorphous silica such as that made by W. R. Grace Company others (e.g. Zeodent 113, DeWolf Chemical, Warwick, R. I.); calcium carbonate ($CaCO_3$); and zeolites (which are microporous aluminosilicate minerals). Colloidal silica, which is silica particles of much smaller dimensions, may also be included to modify the rheology of the 3D network or improve the removal of plaque from teeth. The concentration of such particles can be in the ranges defined herein for the prototype formulation (irrespective of other ingredient concentrations in the prototype formulation). A composition of embodiments of the invention can contain silica, typically amorphous hydrated silica having a hardness less than 3 on the Mohs hardness scale. This would be mostly for stain removal, while being soft enough so as not to erode enamel. Such material is available from W R Grace Co. as SYLODENT®. Among the many known forms of silica, silica used herein may be dental grade silica, which provides appropriate hardness and particle size range.

Abrasives may be included in toothpastes of the invention. Abrasives in dentifrices are moderately hard particulate substances, which are primarily added to dentifrice compositions in amounts of between 7% and 90% (w/w). For a tooth powder the concentration of abrasive might be from about 20% to about 90%. For a toothpaste, the concentration of abrasive might be from about 5% to about 70%. For a tooth gels or liquid toothpastes, the concentration might be from about 5 to about 40%. For a tooth liquid the concentration of abrasive might be from 5% to about 30% w/w. Hydrated silica and calcium carbonate are the most common abrasives.

The standard method of determining dentifrice abrasiveness is using the Relative Dentin Abrasion (RDA) procedure, which is based on the Radioactive Dentin Abrasion Method of Grabenstetter et al. (Grabenstetter R J et al., J Dent Res 1957; 37:1060-1068. Also, Bruce R Schemehorn et al., Abrasion, polishing, and stain removal characteristics of various commercial dentifrices. J Clin Dent 2011; 22(1) 11-18). The standard method compares the abrasivity of the dentifrices being evaluated with that of a standard ADA slurry (RDA=100). In Grabenstetter, the measurement of the abrasion of human teeth by dentifrice abrasives: a test utilizing radioactive teeth. To accomplish this, irradiated dentin samples are brushed with a slurry of the toothpaste in a standard brushing machine using fixed standard conditions such as the amount of toothpaste and dilution, number of brushing cycles, etc. The amount of radioactive material abraded from the dentin surface into the dentifrice brushing slurry after a particular number of cycles is then measured and compared with the results obtained using a standard ADA toothpaste slurry.

A toothpaste with an RDA abrasivity below about 70 is generally considered to have a low abrasivity. Such a dentifrice is suitable for users whose teeth have a low or tendency to stain. A toothpaste with an RDA abrasivity in the range of about 70 and to about 150 would be considered to be moderately abrasive A toothpaste with an RDA abrasivity of from about 150 to about 200 would be considered to have a high abrasivity and suitable for users with a tendency to tooth staining, such as smokers and tea drinkers. The FDA recommends an upper limit on RDA abrasivity of 200, while the ADA recommends an upper limit of 250. Toothpastes with an RDA abrasivity above 250 would be considered to be excessively abrasive and potentially damaging to teeth. An overall acceptable abrasivity range for toothpastes of this invention is from about 50 to about 200, more preferably from about 50 to about 140.

There are widely varying types of abrasives that can be used in toothpastes of embodiments of the invention. The following provides a non-exclusive list of abrasives that would be effective in these toothpaste compositions: Alumina, hydrated alumina, silica, hydrated silica, calcium carbonate, dicalcium phosphate dihydrate, anhydrous dicalcium phosphate, tricalcium phosphate, calcium pyrophosphate, calcium hydroxy apatite, heat treated dicalcium phosphate, sodium metaphosphate, calcium polymetaphosphate, magnesium orthophosphate, titanium dioxide, perlite, sodium bicarbonate and aluminum silicate.

In selecting the abrasive, the one chosen must not only perform its desired function of cleaning without scratching or abrading the teeth, but the abrasive must also be compatible with the fluoride source. There are several abrasives that cannot be usually be used with sodium fluoride or stannous fluoride because they cause the precipitation and inactivation of fluoride ions on storage. These include for example, alumina, hydrated alumina, calcium carbonate, dicalcium phosphate dihydrate, anhydrous dicalcium phosphate, tricalcium phosphate, untreated calcium pyrophosphate, calcium polymetaphosphate, magnesium orthophosphate, and aluminum silicate. The following abrasives are compatible with sodium fluoride: silica, hydrated silica, heat treated calcium pyrophosphate phosphate, sodium metaphosphate, titanium dioxide, perlite and sodium bicarbonate. The following abrasives are compatible with stannous fluoride: silica, hydrated silica, heat treated dicalcium phosphate, sodium metaphosphate, titanium dioxide, perlite.

A wide choice and range of amounts of abrasive can be used dentifrices of the invention. Excessive toothpaste abrasivity is of course of concern regarding the potential scratching of tooth surfaces or thinning of the enamel layer. Furthermore, it would be possible to formulate a second "whitening" version of toothpaste of embodiments of the invention for users who tend to have greater stain build up on their teeth. Whitening can be further augmented by including complex phosphates in the toothpaste. There are many types of abrasives which can be used, but a satisfactory choice might be a mildly abrasive dental grade of hydrated silica. It can be noted that the level of abrasivity provided by any amount of NanoClean cellulose, itself, may be low.

SuperAbsorbent Polymer. In embodiments of the invention, a composition can include a superabsorbent polymer (SAP). Information on SAP, and options for SAP, such as particulate SAP, can be found in patent application U.S. Ser. No. 16/461,536, filed May 16, 2019, for example at §§ 0029-53. The SAP can be surface crosslinked or non-surface crosslinked or a mixture of the two forms.

SAP particle size can be from 2 to 63 microns or from 2 to 106 microns or from 2 to 150 microns or larger, and can include particles up to 800 microns. The SAP polymer is envisioned to be in the form of discrete particles that retain their identity as separate particles even after swelling. This is in contrast to substances that are macromolecular in nature (such as Carbopol) which swell and make hydrogels that are difficult to flow under stress. However, the use of some carbopols in the composition may be tolerated as long as it does not introduce lubrication or as long as it does not diminish friction as determined by friction factor and by friction coefficient or as determined by the micro-friction method based on flow in narrow tubes coated with the test biofilm as described elsewhere herein. It is believed to be preferable to use SAP particles that are surface crosslinked. Such particles avoid forming a sticky or mushy composition. It is also possible to use particles of SAP that are highly bulk crosslinked. A common chemical category of SAP polymers is polyacrylate-acrylic acid polymers, but any dental use safe SAP chemistry can be considered, and embodiments of the invention are not limited to polyacrylate-acrylic acid polymers and may include natural SAPs for example polysaccharide-based SAPs as described elsewhere herein. The SAP particles may be able, even when mixed or incorporated in the described composition, to preserve their integrity as discrete particles rather than joining other SAP particles to form a soft mass or expanded gel domains. In order to satisfy acceptable sensory requirements for toothpaste, the SAP particle size may be small enough so that the composition does not have a grainy feel in the user's mouth; for example, the particles may have dimensions of less than 200 microns in the swollen state. The CRC (Centrifuge Retention Capacity) values may be from 50 to 500 g/g in pure water or from 15 to 50 g/g in saline solution. The CRC value for a cross-linked SAP is expected to be smaller than the CRC value for a non-cross-linked version of the same substance.

It is believed (although it is not wished to be limited to this explanation) that particles of SAP that are Surface Crosslinked are more likely to retain their shape and would not be likely to simply roll around during flow or toothbrushing. It is believed, although it is not wished to be limited to this explanation, that desirably the SAP particles should not be ground or milled after Surface Cross-Linking, so that not more than 10% of the bulk polymerized SAP is exposed, or 10% of the total surface of the SAP, or 10% of the particles. The majority of the SAP particles may be provided having outer surfaces that are intact after the surface cross-linking. The surface crosslinked SAP also increases the gel strength and the elastic properties of the composition (G' compared to non-surface-crosslinked SAP) and may retard the effect of dilution due to water or saliva according to our rheology measurements as provided elsewhere herein. It is possible that such particles of SAP may have edges or corners that are sharp. Other SAP particle shapes may be used including spherical or irregular without limitation. The nature of surface cross-linking can be selected from safe compounds for use in the oral cavity. The density of bulk and surface cross-linking density can be tailored as desired without limitation. Surface-crosslinked SAP is schematically illustrated in FIG. 1D.

A desirable criterion regarding Surface Cross-Linking (SCL) or otherwise particulate SAP can be that if the particles are contacted against each other under load, the particles do not join or merge with each other. Particles of SAP that are surface cross-linked may have CRC values that are smaller than the corresponding values for the same SAP material that is not surface cross-linked. Thus, the CRC value may be a representation of how much cross-linking has occurred. The outer surface of the SCL particles may desirably be thick enough to result in a CRC value in saline (0.9% concentration of NaCl) less than 32 g/g, preferably less than 28 g/g. The particles of SAP may be at least partially entangled in the network or it may be described that the particles of SAP are occluded or incorporated in the network formed by the Minute Fibrils. The Minute Fibrils can surround and capture or entangle with the particles of SAP, i.e., the SAP particles are preferably not loose.

In embodiments of the invention, it is possible to use particles of SuperAbsorbent Polymer that are surface cross-linked, or bulk cross-linked, or any combination thereof or a mixture of these kinds of particles. The range of sizes of those particles can be from 2 microns to 200 microns, or larger.

An example of a natural superabsorbent absorbent polymer is soluble fibrous ingredient comprises psyllium polysaccharide. This polysaccharide is present in natural plantago ovarta, as well as in psyllium husks, seeds and leaves. This polysaccharide source, which is mostly composed of inulin, is a fructan with a beta-(2-1) glucoside linkage. This mucilaginous material expands in water and increases its viscosity. It helps to provide more structure and enhances plaque biofilm removal. Another natural source of soluble super absorbent mucilage are beta-glucans from oats, oat bran, flaxseed, pectin and gums found in berries, seeds, citrus peel and other fruit sources. etc. Water-absorbing polysaccharides can be used as long as they are not lubricating as specified elsewhere herein.

Surfactant or foaming agent. In embodiments of the invention, the composition can include a surfactant or a mixture of surfactants. With conventional toothpastes, one function of such toothpaste is to create foam when the composition is agitated. This foaminess is a sensory attribute that many users have come to expect. Accordingly, in embodiments, the composition can include a surfactant that can produce foam upon being agitated. Sodium laureth sulfate and cocamidopropyl betaine are the most the popular surfactants that can be used in toothpastes or other oral rinses. Sodium lauryl sulfate is also possible.

Other possible surfactants include for example sodium lauryl sulfate (SLS) or sodium dodecyl sulfate (SDS) which is commonly used in commercial toothpastes. In general, surfactant can be any type of surfactant, including for example, anionic, cationic, or amphoteric surfactants. It is useful to specify the level of foaminess and the type of foam so that the composition can remain effective in removing plaque biofilms and calcium deposits during application.

The concentration of surfactant can be adjusted to a concentration that does not degrade the frictional properties of the composition and does not decrease the elastic or viscous or rheological properties of the Nanoclean tooth cleaner as described elsewhere herein.

Preferred ingredients in compositions of the invention are one or more surfactants which are present in an amount not to exceed about 2.5% and preferably in an amount between 0.2% and 1.5%. Higher levels can be irritating while lower amounts will not create sufficient foam. The primary purpose of surfactants is to promote cleaning and create some foam. Surfactants may also have benefits as emulsifiers, which can be used to disperse water insoluble ingredients such as flavor oils into the dentifrice. During storage, such insoluble oils might otherwise undesirably separate from the bulk aqueous phase. With conventional toothpastes, one function of such toothpaste is to create foam when the composition is agitated. Accordingly, in embodiments, the composition can include a surfactant that can produce some foam upon being agitated as long as the type and concentration of the surface does not negatively impact the desirable rheological or friction properties as detailed elsewhere herein.

Suitable surfactants include almost any non-toxic, non-irritating surfactant. Most preferred surfactants are either anionic or amphoteric surfactants and mixtures thereof. Nonionic surfactants are acceptable particularly as emulsifiers but they tend not to deliver as high a foam as is achieved with anionic surfactants and amphoteric surfactants. Nonionic surfactants may be utilized in combination with anionic or amphoteric surfactants to stabilize the foam. Alternatively, nonionic surfactants are useful as emulsifiers, for example to disperse flavor oils and other insoluble ingredients into the dentifrice. Cationic surfactants can also be used in low levels though they are less desirable than other surfactant types because they tend to be irritating and stain teeth. Where cationic surfactants can sometimes be used is to provide anti-microbial activity to the dentifrice. However, cationic surfactants are often incompatible with other ingredients in some formulation. Higher levels of cationic surfactants tend to be more significantly more cytotoxic to oral mucosa than other surfactants.

Examples of suitable anionic surfactants are water-soluble salts of alkyl sulfates with between 8 and 18 carbons in the alkyl chain. A most preferred alkyl sulfate is sodium lauryl sulfates. Another group of useful anionic surfactants include water salts of lauroyl, cocyl, myristoyl and palmityl and stearoyl sarcosinates. Particularly preferred is sodium lauroyl sarcosinate.

In general, surfactant can be any type of surfactant, including for example, anionic, cationic, or amphoteric surfactants. Preferable anionic surfactants for use in toothpaste of this invention include sodium lauryl sulfate (SLS), which is also known as sodium dodecyl sulfate (SDS). Another suitable anionic surfactant is sodium lauryl sarcosinate. Another group of high foaming anionic surfactants are sodium salts of hydroxyalkyl sulfates, for example sodium 2-hydroxytetradecyl sulfate and sodium 2-hydroxydodecyl sulfates. These surfactants are known to avoid the "orange juice effect" experienced with many other anionic surfactants. The orange juice effect results in a seriously adverse flavor when orange juice is imbibed after toothbrushing with surfactant-containing toothpaste. Among other useful anionic surfactants are sodium N-methyl taurate, and sodium salts of sulfonated monoglycerides.

A preferred amphoteric surfactant is cocamidopropyl betaine. A suitable group of nonionic surfactants includes those known as the poloxamers (block co-polymers of ethylene and propylene oxide.

Suitable antimicrobial cationic surfactants include benzalkonium chloride, benzethonium chloride, methyl benzethonium chloride, cetyl pyridinium and tetradecylpyridinium chloride.

Cationic surfactants may be less preferred for cleaning teeth.

Another ingredient that can be used is LAE (Lauryl Alginate Esters) hydrochloride or other salts. LAE is a natural cationic surfactant and is a natural preservative, and it has good attributes for retarding biofilm formation. For example, we have found that a concentration of 0.1% to 1% of LAE, or 0.5% to 1%, in combination with other ingredients of NanoClean tooth cleaner, can also produce foam and promote cleaning. LAE is a cationic surfactant and it breaks down to arginine (which is an amino acid) and lauryl acid (which is a fatty acid) both of which are common in food and are safe. LAE seems to lower surface tension of its composition and may also have a propensity to absorb on the surface of teeth giving after-brushing more persistent effect that may delay or retard biofilm formation. LAE has good ability to form foam (which is desirable in toothpaste), and also is a preservative and has some antimicrobial effect. It is considered a cationic surfactant and can replace other surfactant options for the formulation. The inclusion of LAE may protect against tooth sensitivity due to its arginine moieties.

Foaming Agent. Foaming agents are a subset of surfactants, and constitute an important ingredient in toothpastes. Consumers perceive toothpastes as less effective at cleaning if the foam is insufficient. However, the amount of foaming agent added to the toothpaste formulation should not be excessive. Excessive foaming agent adversely affects flavor and mouth feel. Furthermore, some consumers are sensitive to surfactants and suffer from mouth sores when too much foaming agent is present. A widely used foaming agent is sodium lauryl sulfate. It is possible that sodium lauryl sulfate is acceptable and less risky than choosing other possible surfactants. On the other hand, it might be possible to identify a more natural or naturally-derived surfactant, though this could take considerable effort. For example, it is possible that a concentration of from 0.5% to 0.8% of sodium lauryl sulfate would prove satisfactory.

Thickener or rheology modifier. Although polymeric thickeners may be less desirable in the compositions of the invention, they may be incorporated at some low concentrations as ling as they would negatively impact the rheological, frictional and plaque removal effectives on the compositions as provide elsewhere herein. As examples of inorganic thickeners, embodiments of the invention may comprise from about 2% to about 10% concentration of silicas, such as Zeodent 163 absorb water and form chemical hydrates with silica. These materials form links and thicken aqueous compositions. It is also possible to use inorganic thickeners such as laponite and other clays. It is also possible to use worm-like micelles formed by surfactant and salt, with examples of the surfactants or mixture of surfactants can include Cetyltrimethylammonium bromide, cetylpyridinium chloride, amine oxide surfactants.

Humectant or hydrating agent or water retention agent. For a toothpaste application, it is desirable that the toothpaste should not dry out. In many current commercial toothpastes, water holding is accomplished by hydration of binders of hydrating or water-swelling polymers.

Many commercial toothpastes contain a humectant such as PEG-12 (polyethylene glycol) or glycerin (glycerol) or sorbitol 70% or mannitol or carrageenan or xanthan gum. Carboxymethyl cellulose also acts as a humectant. For example, sorbitol has lubricating properties. PEG-12 is a polyethylene glycol with 12 ethylene glycol repeating units within the polymer and is a humectant and solvent. Compositions of the invention may include limited amounts of one or more humectants selected from the following glycerin, propylene glycol, propanediol, xylitol, neotame, acesulfame, thaumatin, glycyrrhizin. These substances are hydropolyomers. Many substances that are humectants also have lubricating properties.

In general, humectants are added to some toothpaste formulations to prevent loss of moisture. Moisture can be lost, for example, when the toothpaste cap is left off. An additional reason to include humectant in a toothpaste is reduce the water activity. Water activity is a measure of the moisture vapor pressure above a toothpaste. As described in U.S. Pat. No. 7,135,163, water activity is considered to be the equilibrium vapor pressure of water above the toothpaste, when kept in a sealed container, divided by the saturated vapor pressure of the water measured at the same temperature. Water activity indicates not only the tendency of the toothpaste to dry out when exposed to the air, but also the chemical activity of the water in the toothpaste. Because bacteria and fungi need moisture to survive, a low water activity will prevent bacterial and fungal growth in the toothpaste. Ideally the water activity should be less than about 60% although 70% can be another useful target.

It is believed possible that humectants may lubricate the toothpaste on teeth and thereby reduce the effectiveness of the toothpaste in removing plaque biofilm. This can be tested. Primary alternatives as humectants are glycerin and sorbitol. However, xylitol may have some additional benefits perhaps by preventing plaque or by favoring less cariogenic bacteria in the mouth. One option is to increase in NanoClean cellulose concentration to offset the lubricity that may result from adding humectants.

If humectants cannot be used in formulations of embodiments of the invention, due to their lubricating effects, alternative ingredients may be used, even if for no other reason than to reduce the amount of water added to the toothpaste and hence help reduce water activity. Inert fillers such as microcrystalline celluloses might be employed to reduce water content and to help control the water activity. Salts that can be added include mono, di and trisodium orthophosphate, monoammonium, diammonium and triammonium phosphate and monopotassium, dipotassium and tripotassium phosphate salts. The pH range can be 5.0-8.5.

In embodiments the formulation has a degree of hydration so as to obtain water activity of about 0.7.

Fluoride. In an embodiment of the invention, the composition may include a fluoride compound that is suitable to deliver active fluoride ions to the teeth. Such fluoride compound may be or may include sodium fluoride (NaF) or stannous fluoride (SnF2) system or sodium monofluorophosphate (Na2PO3F) or other acceptable sources of fluoride without limitation. Such compounds are widely used in toothpastes and other dentifrices to strengthen tooth enamel.

It is believed that such compounds convert the calcium mineral apatite into some form of fluorapatite. It is further believed that the resulting tooth enamel is more resistant to bacteria-generated acid attacks. The effective bioavailable concentration of fluoride should be equivalent to that of current commercial toothpastes. Such fluoride compound may be or may include sodium fluoride (NaF) or stannous fluoride (SnF2) or sodium monofluorophosphate (Na2PO3F). Such compounds are widely used in toothpastes and other dentifrices to strengthen tooth enamel. It is believed that such compounds convert the calcium mineral apatite into fluorapatite. It is further believed that the resulting tooth enamel is more resistant to bacteria-generated acid attacks. The effective bioavailable concentration of fluoride may be chosen to be equivalent to current commercial toothpastes.

In one of the commercially available toothpastes, the concentration of sodium fluoride is 0.24% by weight. In Crest toothpaste, the concentration of stannous fluoride is 0.454% (which corresponds to a 0.15% w/v concentration of active fluoride ion). In embodiments of the invention, a fluoride concentration similar to or possibly higher than these concentrations can be used.

It can be noted that the presence of active fluoride ions was not a consideration for applications such as the cleaning of endoscope channels (described in U.S. Ser. No. 10/266, 793). Although a toothpaste could be made without fluoride, most current toothpastes include fluoride as recommended by the American Dental Association. It is preferred to include water-soluble compounds, which deliver free fluoride ions to the teeth. Dentifrices that deliver appropriate amounts free fluoride ions have been proven to significantly reduce the incidence of caries in users.

When included in dentifrices, preferred fluoride compounds are sodium fluoride (NaF), stannous fluoride (SnF2), or sodium mono-fluorophosphate (Na2PO3F). Such compounds are widely used in toothpastes and other dentifrices to prevent caries and strengthen tooth enamel. All three of these fluoride ingredients are approved by the FDA as proven Safe and Effective for use as an anti-caries agent in dentifrices. Less preferred but acceptable fluoride compounds for use in dentifrices of the invention are amine fluorides. While amine fluorides are reported to deliver more fluoride to tooth mineral than other fluoride compounds, amine fluorides are not are not approved for inclusion in dentifrices by the FDA in the USA.

There are several mechanisms by which fluoride prevents caries (1) Fluoride ions promote remineralization of tooth enamel using calcium and phosphate ions from saliva; (2) Fluoride ions react with calcium hydroxyapatite in tooth enamel producing a less water-soluble calcium fluoro-apatite and thereby reduce enamel demineralization due to acids from cariogenic bacteria; (3) Fluoride has an inhibitory effect on the growth of oral bacteria, thereby decreasing acid release by cariogenic bacteria.

Each fluoride-releasing compound has different characteristics, which affect the choice of fluoride depending on the composition of the dentifrice. Sodium fluoride completely releases essentially all of its fluoride ions to the saliva during brushing for maximum effectiveness. However, fluoride can be precipitated and deactivated in the presence of divalent and some other ions or by some types of abrasives. Hence sodium fluoride cannot be used in compositions containing such materials.

The fluoride in sodium mono-fluorophosphate is not present in the form of free soluble fluoride ions. Hence, the fluoride in sodium mono-fluorophosphate is "protected" from reaction with divalent and other incompatible ingredients. Therefore, sodium mono fluorophosphate is the fluoride source of choice for dentifrices containing fluoride-incompatible ingredients. Studies generally indicate that sodium mono-fluorophosphate is slightly less effective than sodium fluoride in preventing caries because it takes time for free fluoride ions to be released from sodium mono-fluorophosphate during brushing.

Stannous fluoride has some performance advantages over other fluoride sources. Firstly, stannous ions react with tooth enamel and strengthens it, making it more resistant to acid attack. Stannous fluoride is also an effective antimicrobial agent, which decreases plaque biofilm build-up on teeth and reduces gingivitis. Furthermore, stannous fluoride is effective in reducing supragingival gingivitis. Another benefit of stannous fluoride is its ability to block dentinal tubules, which lead to the nerves in teeth. As a result, stannous fluoride is effective in preventing tooth sensitivity. On the negative side, stannous fluoride is somewhat less stable than sodium fluoride in dentifrices. Hence stannous fluoride-containing dentifrices gradually lose some of their effectiveness on storage. Additionally, stannous ions cause stain build-up on teeth. Furthermore, stannous fluoride imparts an adverse flavor, which is difficult to cover.

Amine fluorides tend to deliver greater amounts of fluoride to the surface of teeth and hence should be more effective in preventing dental caries. However as noted above, amine fluorides are not approved by the FDA in the USA but are used in some countries Dentifrices of the invention general contain between about 0.05% to about 1% by weight of soluble fluorine. Dentifrices for regular twice daily home use should contain between about 0.08% to about 0.25% soluble fluorine compound. Prophylaxis pastes, used in the dental office, should contain from about 0.2% to about 0.5% fluorine. It can be noted that fibers and other components might skew what amount of fluoride is biologically available. For the USA, the permitted contents for fluoride toothpaste are identified in Table 1.

TABLE 1

| Type of fluoride | Average % F ion | F ion Range | % as compound |
| --- | --- | --- | --- |
| Sodium fluoride | 1100 pm | 850-1150 ppm | 0.188-0.254% $SnF_2$ |
| Stannous fluoride | 1100 ppm | 850-1140 ppm | 0.351-0.474% $SnF_2$ |
| Sodium MFP | 1100, 1500 | 850-1150 or 1500 ppm | 0.654-0.884 or 1.153% NaMFP |

Additional ingredients, Adjuvants. In embodiments of the invention, the composition can include any one or more additional ingredients or adjuvants such as: a sweetener such as sucralose or sodium saccharin; flavoring; a preservative. a humectant such as PEG-12 (polyethylene glycol) or glycerin or sorbitol 70%. It is also possible to include a pH adjuster, as known in the art. Embodiments of the invention may include one or more sweeteners such sucralose or saccharin, sodium saccharin, sodium cyclamate, sucralose, steviolglycodes, aspartame, acesulfame, xylitol, neotame. A possible starting point could be to use a concentration of about 0.3% to 0.5% saccharin, optionally combined with up to 0.1% sucralose. Sodium saccharin is a sweetener, benzoic sulfimide (C7H5NO3S, having a Molecular weight of 183.18 g/mol). Compositions of embodiments of invention may include from about 0.1 to about 2.0% concentration of flavoring agents including but not limited to as oil of peppermint, oil of spearmint, oil of wintergreen, methyl salicylate, eucalyptus, eugenol, clove, lemon, grapefruit, orange, vanilla, vanillin, thymol, carvone, licorice etc.

Embodiments of the invention may comprise anti-plaque agents including Maleic acid copolymer, beta-D-galactose, beta-D-N-acetyl glycosamine, lactose, L-rhamose, beta-D-fucose (U.S. Pat. Nos. 4,362,713, 5,362,480; 4,775,525). Embodiments of the invention may comprise 1-20% Sodium alginate (Average Molecular Weight 222) which helps to remove plaque by chelating calcium. Embodiments of the invention may comprise anti-plaque polysaccharide (U.S. Pat. No. 4,855,128) in a concentration of from 0.0025% to 1%. Such polysaccharides may be selected from the group consisting of lactobionic acid, xanthan gum, guar gum, gum tragacanth, guar gum, polygalacturonic acid, as long as they do not degrade the frictional properties of the composition as described elsewhere herein.

A significant portion of the population suffers from tartar (also known as calculus) build up on their teeth. This is dependent on the calcium content of their saliva, and often increases due to misalignment of teeth, which causes calcium phosphate deposition on and between teeth. Compositions of embodiments of the invention can include a tartar control agent such as pyrophosphate, tripolyphosphate and hexametaphosphate salts, and zinc chloride. These complex phosphates are also useful in preventing stain build up in the tooth surface and for supporting claims of tooth whitening.

Tooth sensitivity often develops in the teeth of people in their thirties or forties. It is caused by receding gums which exposes dentin which is normally below the gum line. Dentin contains tiny tubules, which allows changes in pressure to the nerves within the pulp. Nerve sensitivity can be controlled using potassium salts such as potassium nitrate. Newer technology provides for ingredients which are deposited on the exposed dentin thereby blocking tubules. Because this toothpaste described herein contains only small quantities of hard abrasives which might remove protective mineral layers on exposed dentin, or may be no such abrasives, the use of a NanoClean toothpaste formulation might be especially desirable for people who suffer from tooth sensitivity.

Embodiments of the invention may include a preservative. It is possible that a preservative will not be needed in this formulation. Sodium fluoride has some anti-bacterial and fungal growth inhibitory properties. Also, if the water activity of the toothpaste is reduced to 60% or less, bacterial and fungal growth would probably be prevented. If desired, there are a broad range of preservatives which could be used usually coupled with a buffer to adjust the pH into a mildly acidic region of about 5 to 5.5.

Categories of ingredients that can be excluded or minimized. Many commercial toothpastes contain a lubricious substance or a substance that has properties of being lubricious.

In embodiments of the invention, the compositions may be essentially free of or may contain limited concentration of low molecular weight lubricants/humectants and are essentially free of or may contain limited concentration of polymeric thickeners/binders that may also function as internal and external lubricants. For example, glycerol and CMC (carboxymethyl cellulose), which are present in many toothpastes, creates lubricity. Sometimes the lubricious substance is included for the express purpose of its lubricity, such as in order to improve the dispensing action of the toothpaste. Sometimes the substance is included for some other property such as water retention or rheology modification, but the substance also happens to have properties that are lubricious. In embodiments of the invention, it may be preferred that the composition not contain excessive amounts of lubricants or lubricious substances and not contain specific substances that are less desirable because of their lubricious nature. In regard to the presence of CMC (carboxymethylcellulose), even a slight amount of CMC can serve as lubricant and can diminish the function of NanoClean tooth cleaner to remove biofilm. Glycerol even at 1% concentration can be deleterious. Some surfactants are lubricating or more lubricating, and other surfactants are not lubricating or are less lubricating. Sodium Lauryl Sulfate can have a deleterious effect. Experimentation can determine in the context of a given formulation what concentration of CMC or other lubricious substance may be detrimental. The composition may be chosen to be essentially free of or contain limited concentrations of low molecular weight humectants and polymeric thickeners or binders, In embodiments, the cumulative amount of such lubricious components (other than a low lubricity surfactant selected as described herein, which itself is at a concentration of preferably 0.5% (w/w) or less, or 0.3% (w/w) or less, or 0.2% (w/w) or less, or 0.1% (w/w) or less.

In embodiments, quantification of the deleterious effect of lubricity is measured by growing a build-up biofilm (BBF) in a tube as described herein, staining it blue, and pumping various compositions through the tube. The performance of a composition without the additive can be compared to the performance of a composition containing the additive. In such comparisons, a concentration of a particular substance(s) that causes a 10% increase in the time to remove BBF indicates a concentration to avoid. Quantification of the deleterious effect of lubricity can also be characterized by rheological or tribological testing as described elsewhere herein.

As discussed elsewhere herein, there may be an avoidance of the ingredient EDTA, for biocompatibility reasons. It is also possible to avoid certain surfactants that have cytotoxic effects on cells. There may be a preference for substances that are approved by the FDA for ingestion.

Table 2 is a table of typical (prototype) composition or range of compositions. It should be understand that a percent concentration, when expressed herein, refers to a weight percent unless otherwise apparent.

TABLE 2

|  | range | preferred range | starting value | purpose |
| --- | --- | --- | --- | --- |
| Deionized water | to 100% | to 100% | to 100% | carrier |
| Zeodent 113 | 1-20% | 3-10% | 3.00% | abrasive, removes stain |
| Zeodent 163 | 0-20% | 3-10% | 0.00% | thickener/Wa adjuster |

TABLE 2-continued

| | | | | |
|---|---|---|---|---|
| fibrillated cellulose (% basis) | 0.7-4% | 1-2% | 0.70% | removes plaque biofilm |
| micro-crystalline cellulose | 1-6% | 1-2% | 1.00% | removes plaque biofilm |
| Sorbitol | 0-20% | 0-5% | 0.00% | humectant |
| Glycerin | 0-5% | 0-1% | 0.00% | humectant |
| Sodium lauryl sulfate and/or other surfactants | 0.05-3% | 0.1-0.5% | 0.05% | foaming agent |
| Sodium Fluoride | 0.24-0.24% | 0.24-0.24% | 0.24% | prevents caries |
| Xanthan gum, carbomer | 0-1% | 0-0.1% | 0.00% | organic thickener |
| Carboxymethyl cellulose 7MF | 0-1% | 0-0.1% | 0.00% | organic thickener |
| PEG-12 | 0-5% | 0-2% | 0.00% | humectant |
| Sodium saccharin | 0.1-0.7% | 0.1-0.4% | 0.10% | sweetener |
| Sucralose | 0-0.1% | 0-0.1% | 0.00% | sweetener |
| Flavor | 0.2-0.8% | 0.1-0.5% | 0.10% | pleasant taste |
| Titanium dioxide | 0-0.05% | 0.1-0.2% | 0.10% | opacifer |
| xylitol | 0-20% | 0.1-2% | 0.00% | humectant |
| erythritol | 0-20% | 0.1-2% | 0.00% | humectant |

| | Inventive Composition | Prior NanoClean |
|---|---|---|
| Sodium saccharin | 0.3 | |
| Sucralose | 0.05 | |
| Sodium fluoride | 0.243 | |
| Sodium lauryl sulfate (SLS) | 0.15 | |
| Cocamidopropyl betaine (35%) | 0.15 | |
| Peppermint flavor | 0.5 | |
| Microfibrilated cellulose (WC) | 1.75 | 0.9 |
| Microcrystalline cellulose (MCC) | 1 | 1 |
| Surface cross linked Sodium polyacrylate (SAP) | 0.5 | 0.8 |
| Titanium dioxide | 0.22 | |
| Hydrated silica abrasive | 10 | |
| Hydrated silica thickener | 3 | |
| 1,2 Propanediol | | 0.5 |
| Dehypound Advanced | | 0.25 |
| Ethox 4485 | | 0.025 |
| Texapon 842UP | | 0.15 |
| EDTA (solid) | | 0.25 |
| Accusol 455 | | 0.2 |
| PNB (glycol ether) | | 0.1 |
| distilled water | 82.137 | 94.925 |

It can be understood that the composition can be made by combining certain solid ingredients listed herein with a liquid that contains a large fraction of water and also some additives dissolved in the water. It can be understood that after such combining and mixing, the liquid does not primarily exist as a separate phase by itself, but rather the liquid, or at least most of it, is absorbed into some of the other ingredients, such that the resulting in a final composition has the consistency of a paste.

Traditional toothpastes are compositions that have high viscosity, non-Newtonian properties, yield stress, and specific formulations. However, they do not possess optimal viscoelastic properties to effectively remove dental biofilms under actual application conditions in the mouth, specifically, when diluted they suffer significant deterioration of properties such as viscosity which renders such products ineffective in removing plaque biofilms. None of these toothpastes had G' sufficiently large to remove biofilms. They have storage modulus G' about or less than 1000 Pa compared to that G'>1500 Pa that is preferred to remove biofilms. Although they have high Yield Stress, they lack the desired elastic component (G') and when diluted with water or saliva they become like thin slurries. A slight dilution takes viscosity from probably 70,000 centiPoise (milli-Pa-s) down to 2000-3000 centiPoise (milli-Pa-s). At this dilution level, conventional toothpastes no longer behave like viscoelastic fluids and are not able to create the requisite forces to remove plaque biofilm from teeth surfaces. In order to successfully remove plaque it is desirable to have a fluid with sufficient viscoelastic and friction properties. These criterial are not satisfied in current commercial products and in this context the industry has not paid attention to satisfying the requirements that are preferable for removing plaque biofilm. The industry focus has been focused on formulating toothpaste to satisfy sensory attributes such as standing on the brush and having suitable squeezing force from the tube, and foam production. Embodiments of the present invention are directed to compositions and methods to effectively remove plaque biofilms from teeth under actual use conditions.

In embodiments of the invention, toothpaste formulations may be made to possess the 3-D network using MFC and having mechanical properties that are sufficiently large (G'>1500 Pa) and yield stress (>30 Pa). The ingredients in the preceding Table can be varied and their effect on rheology and mechanical stresses so as to remove biofilm can be determined. We can use classical rheometry to assess the mechanical properties of formulations. The effective shear stresses for removing biofilm may be assessed from experiments performed with biofilm grown with $S.\ mutans$ bacteria. It is desirable that the compositions of the invention have the properties appropriate for removing dental biofilms even when diluted by induced saliva during brushing or during application by employing other applicator designs.

Resisting degradation in performance due to dilution. It is typical that during the time that a toothpaste is used in toothbrushing, the toothpaste will encounter saliva or water and will become diluted. This may be referred to as "saliva induced dilution." As a benchmark, it is useful to consider that the toothpaste becomes diluted to half of its initial concentration, or one-quarter of its initial concentration. Typically, it is found that for conventional toothpastes, the viscosity decreases drastically with dilution and the toothpaste loses it viscoelastic properties, which quickly renders the composition less and less effective for removing plaque or biofilm. In contrast, with NanoClean tooth cleaner, even if the composition is diluted by half, there remains a network of fibers or fibrils, and the composition remains effective for removing plaque or biofilm.

In an embodiment, the inventive composition can retain its effectiveness in removing biofilms during and after dilution by saliva. In order for NanoClean tooth cleaner to work well, it is useful that NanoClean tooth cleaner resists dilution such that when diluted by half it still is effective in removing dental plaque. For fluoride testing, FDA recommends doing testing at 25% concentration. May be this means that what the mouth sees during brushing is approximately that dilution. The NanoClean tooth cleaner composition can be formulated to be effective in removing dental biofilm even when it is diluted to 25% of its original concentration.

Not wishing to be bound by theory, the stiffness (G' or elastic modulus) and strength of the gel network (yield shear stress) is usefully larger than that of the biofilm in order to achieve more complete removal of biofilm. Literature data indicate that G' of biofilms can range from less than 100 Pa to more than 2000 Pa (Stoodley et al., Structural deformation of bacterial biofilms caused by short-term fluctuations in fluid shear: an in-situ investigation of biofilm rheology," Biotechnol Bioeng. 1999 Oct. 5; 65(1): 83-92). In embodiments, the network may be strong enough, having high yield shear stress, so that it can maintain sufficient elastic properties during flow in order achieve effective removal of biofilm as exemplified by removal of BBF ("Build up Biofilm" described elsewhere herein). Gel network compositions can be made to satisfy such requirements according to embodiments of the invention.

Dilution Considerations

For selecting the formulation of compositions of embodiments of the invention, a consideration is the amount of moisture (water, saliva) present in the mouth during brushing. This may dilute the concentration of any toothpaste or dentifrice, potentially reducing plaque removal performance.

In short, while exact estimates of toothpaste dilution in the mouth can vary significantly between subjects, it is reasonable to suppose that dilution occurs in the mouth in the proportion of approximately one-part toothpaste with about three parts saliva. In the final FDA Monograph on Fluoride toothpastes there are several test methods recommended for qualifying fluoride performance by fluoride-containing dentifrices which, in most cases, use a dilution of one-part toothpaste to 3 parts diluent. Accordingly, as a starting point, it is reasonable to assume that the dilution of toothpaste in the mouth during brushing is to about 25% of its original concentration. The original composition or concentrate used as the toothpaste can have a concentration of water sufficient to provide the desired paste properties. As an example, the concentration of water in the toothpaste can be at least 55% water, at least 60% water, and can be less than 85% water and less than 80% water, although alternatives are available.

Apparatus and Applicator and Methods of Use

In embodiments of the invention, compositions can be combined with various types of applicators.

Referring now to FIG. 2A, in an embodiment, a described composition can be coated onto or loaded into a dental floss or dental tape. The dental floss or dental tape can have a cross-section that is generally round (dental floss) or somewhat elongated (dental tape). The dental floss or dental tape can be monofilament, in which case the described composition can be applied as a coating on the dental floss or dental tape.

Alternatively, in embodiments, referring now to FIG. 2B, the dental floss or dental tape can be multifilament or porous, in which case the described composition can be located in interstices of the dental floss or dental tape. In embodiments, the dental floss or dental tape can have a surface that is fuzzy, in which case the described composition could be located between the fibers that make up the fuzzy surface.

FIG. 2C shows an embodiment in which a dental floss of any disclosed microstructure, and possibly including a composition of an embodiment of the invention, may be mounted in a floss holder. The floss holder may be such as to improve the ease of manipulating floss into and within the interproximal space.

Referring now to FIG. 2D, in an embodiment, there can be provided a flexible interproximal brush. The flexibility of the flexible interproximal brush can allow it to pass through narrow spaces and can allow it to be pulled through those spaces and can allow it to be bent around surfaces of the tooth or teeth being cleaned, With respect to its overall length, a central region of the flexible interproximal brush can have bristles extending transverse to the longitudinal direction of the flexible interproximal brush, to a greater transverse dimension than the transverse dimension of the device in places where those bristles are absent. The ends of the flexible interproximal brush do not, in embodiments, have such bristles, and their absence might make it easier to initially thread the device between teeth. A composition described herein can be coated onto the flexible interproximal brush or loaded in between the bristles of the flexible interproximal brush.

Referring now to FIG. 2E, in an embodiment, there can be provided a stiff interproximal brush. The use of the term stiff interproximal brush is intended to describe that the stiff interproximal brush can, if desired, be urged into the interproximal space by gripping a hand-grippable portion of the stiff interproximal brush and pushing. Of course, the same stiff interproximal brush can also be pulled using the hand-grippable portion, if desired. A described composition can be coated onto the stiff interproximal brush or loaded in between the bristles of the stiff interproximal brush.

Referring now to FIG. 2F, in an embodiment, there can be provided a toothbrush, which can deliver a composition to the brushing region. The toothbrush can comprise a polymeric foam, which may be either a closed-cell foam or an open-cell foam. If the foam is a closed-cell foam, the foam may be cut open at the exposed surface, resulting in open cells immediately at the surface, and the composition of an embodiment of the invention can be contained inside cells that have been cut open and are exposed. In the case of an open-celled foam, the composition of an embodiment of the invention can be contained inside various cells and can pass from one cell to another as needed. With an open cell foam, it would even be possible to refresh toothpaste during use by squeezing additional toothpaste out from another part of the toothbrush. For example, the composition could be stored in the handle of the toothbrush and could be squeezed out as needed to replenish the toothpaste at the location of the teeth. It is possible that the applicator could further comprise a structural element that is made of something other than foam. The structural element could be stiffer than the foam. For example, the foam element can be surrounded by bristles. A typical closed cell foam is for example Polyethylene Foam. It typically has a white color and is used for many purposes in packaging and other applications.

In embodiments of the invention, it is possible that a composition of an embodiment of the invention can be used with any conventional toothbrush, in place of conventional toothpaste. This includes a manual toothbrush; a motor-driven toothbrush such as the Oral-B® brand (Procter & Gamble, Cincinnati, Ohio); and a sonic toothbrush such as Philips Sonicare™ (Philips, Netherlands).

Referring now to FIG. 2G, in an embodiment, a toothbrush may comprise individual bristles, anchored in the base of the toothbrush, wherein the individual bristles are not monofilament fibers, but rather contain small spaces within them. Such individual bristles may be multifilament, having spaces between the filaments, or they may have pores. For example, the bristle may be made of flocked Nylon. In any event, the small spaces within an individual bristle may contain composition of an embodiment of the invention.

Referring now to FIG. 2H, it is possible that a composition of an embodiment of the invention can be directed to impinge (e.g., collide) against a surface of a tooth for purposes of cleaning.

Such impingement may be in the form of a continuous or pulsed jet of liquid or fluid, driven by a pump or pressure source in a manner such as is conventionally obtained from the device known as Waterpik® (Water Pik, Inc., Fort Collins, Colo.).

Alternatively, it is possible that a composition of an embodiment of the invention can be directed to impinge against a tooth by a puff of pressurized air or gas. In air flossing, controlled amounts of a fluid composition are propelled by puffs of gas into locations such as the interproximal spaces or into any other location. This can be done as is conventionally done in the device known as Airfloss (Philips, Netherlands). A typical NanoClean tooth cleaner formulation which contains 0.7% MFC and 0.7% SAP and 1% MCC can be used in AirFloss. An air pump can sufficiently pump the composition (it is shear thinning, allowing easier flow with shear) and can provide sufficient flow between teeth to remove biofilm. The shear-thinning property may be helpful in achieving this.

An embodiment of the invention can include introducing into the interproximal space an inventive composition having physical properties of mouthwash or of toothpaste or anywhere in between mouthwash and toothpaste.

In connection with jetted applications of the composition, an applicator with a slit or orifice geometry could be useful for propelling the composition into the interproximal space, and the locally high shear at the orifice/slit could cause the viscosity to drop enough for fluid to flow from the orifice into interproximal space. Flow and forces generated in interproximal space are sufficient to remove biofilm. Such a composition would in embodiments be thinner than commercial toothpaste and its shear-thinning properties would help it to impinge.

In impingement applications resembling either Waterpik or AirFloss, it is helpful in embodiments if the composition includes friction elements such as MicroCrystalline Cellulose. One could select the particle size of the friction elements to be small enough to flow between teeth. For example, the MCC particles can be 25 microns to maximum of 100 microns overall dimension (average).

In embodiments of the invention, the composition can be formulated so as to prevent or discourage formation of aerosol, i.e., the composition can have viscosity properties such that it is not so thin as to easily form aerosol. It would be undesirable to create droplets of respirable size such as less than 5 microns diameter.

In still other embodiments of the invention, the composition of the invention can be a mouth wash or mouth rinse having lower viscosity than toothpaste, so that the mouthwash can be made to flow in the interproximal space and remove dental plaque from surfaces in-between teeth. The concentration of the fiber and fibrils as well as of the friction elements can be sufficient to remove plaque with the mouth by movement as the driving forces for hydrodynamic flow.

The properties of a mouthwash of embodiments of the invention may be similar to the properties already discussed for toothpaste except that motion may come from swishing the mouthwash in the mouth of the user, rather than from externally supplied motion of a brush. The mouthwash can be formulated so that it still is thick enough to remove biofilm but is not so thick as to prevent flow into and within the interproximal space. The composition of mouthwash can be adjusted based on expected shear rate. Compared to toothpaste, the mouthwash can be less viscous or have a smaller yield stress.

In still other embodiments of the invention, a composition may be provided that has properties intermediate between those of toothpaste and those of a typical mouthwash. In general, the properties of such a composition could be such as to resemble syrup. While this may be a novel texture for the user, its effectiveness can motivate the user to try this new texture.

Embodiments of the invention can be used to clean the tongue. The tongue is a breeding ground for bacteria and has crevasses that hide the bacteria and which the compositions of the invention can effectively sweep. A reduced bacterial load on the tongue can result in a longer recovery time for the bacterial at or near the teeth, and thus improved dental health.

In still other embodiments of the invention, an embodiment of the invention can take the form of chewing gum. Chewing gum can be a substance that has elasticity and large elongation and is not brittle. A chewing gum substance could be for example a waxy substance, or xanthan gum or gum Arabic or the like or synthetic polymers, or other gum bases. Currently, dental chewing gums do not include fibers in them. An embodiment of the invention can contain a chewing gum substance in combination with polymeric fibers during chewing will give friction that erodes biofilm. t could further contain friction elements, which will give similar to NanoClean tooth cleaner. The concentration of MFC or MFC+MCC can be sufficient to induce friction but not so high as to shed in the mouth; the fibers and possible friction elements should remain occluded in the chewing gum mass. For example, the concentration of these additives might be less than 1% (wt/wt) concentration of MFC and less than 1% concentration of MCC, with the remainder being chewing gum base.

In the practice of oral hygiene in most developed areas of the world, a bristle brush is used to scrub the surfaces of the teeth and gums, in an attempt to remove residual food particles and biofilm from these surfaces, usually with a dentifrice applied to the brush, to assist in the removal of the biofilm. The bristle brush used for dental hygiene is most commonly a simple plastic handle with a small flattened face near one end from which a plurality of brush bristles protrude. It is positioned in the mouth, with the bristle tips against the surfaces to be scrubbed, and manually oscillated along the surfaces.

Other variants of the tooth brush include the oscillation of the brush bristles is caused by a powered mechanism, such as designs in which a brush element with a shortened handle is attached to the powered mechanism, and the brush handle is oscillated by the powered mechanism, or designs in which the brush element is a small circular plate, with bristles protruding from one circular face, which when affixed to the powered mechanism, is rotated, or oscillated in a rotary fashion, about an axis parallel to the bristle length.

Because none of the just-described brushes are able to effectively penetrate and clean the interproximal spaces between the teeth, the use of a dental floss or tape, or interproximal brushes. However, due to lack of effectiveness of these items, unremoved biofilm builds up over time and hardens into dental calculus, which then requires periodic professional removal.

A composition of an embodiment of the invention, comprising nanoscale cellulosic fibers suspended in a gel formulation can flow along a surface to which a biofilm is adhered, causing shear stresses between the composition and the biofilm are sufficient to overcome the adhesion of the biofilm to the surface, and the biofilm is removed.

It is known that the shear stress in a flowing fluid like material is parallel to the direction of flow, and, for laminar flow, is proportional to the viscosity of the material and to the velocity gradient in the direction normal to the flow direction. In a closed channel, such as a tube, or pipe, the velocity gradient in the fluid, normal to the flow direction, is greatest at the tube wall, and is proportional to the mass flow rate through the tube, and inversely proportional to the tube diameter. For small bore tubes, a small amount of material, pumped through the tube, can efficiently and cost effectively clean biofilms from the interior of such tubes. The method works because the cleaning formulation is constrained to flow along the interior surface of the enclosed channel, and the velocity gradient at the wall is maintained for the length of the tube.

Figure 4A:
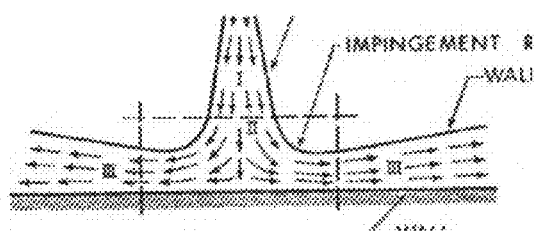
FIG. 4A illustrates a flow pattern in a fluid impingement situation.

When trying to clean open surfaces, such as the surfaces of teeth, it is difficult to produce a flow of the cleaning formulation along the open surface, the flow having a sufficient velocity gradient to produce the required shear stress upon the open surface to facilitate removal of any adhered biofilm. One means to achieve the desired shear stress, would be to impinge a jet of the cleaning formulation against the surface to be cleaned, as illustrated in FIG. 4A.

At the center of the area of impingement, there is a stagnation area where there is rather small fluid velocity parallel to the surface, thus low shear stress. Beyond the stagnation zone, there is an annular zone, wherein the cleaning formulation is flowing radially outward with a sufficient velocity gradient to produce effective cleaning. Beyond this annular zone, the flow thickens and slows, such that there is no longer a sufficient velocity gradient at the surface to produce high enough shear stresses to remove the biofilm.

A jet of cleaning formulation directed through the interproximal spaces between the teeth would produce sufficient velocity gradients for effective cleaning along the surfaces of the teeth within the interproximal spaces, as the interproximal spaces somewhat define a narrow channel which partially constrains the flow of the cleaning formulation, resulting in sufficiently high velocity gradients within the confines of this channel.

Because the impinging jet effectively cleans only a small area proximal the center of the jet, when applied to the open surfaces of the teeth, it would require a relatively long time, and a prohibitively large volume of cleaning formulation to effectively clean all of the tooth surfaces in an individual's mouth.

What is desirable is a means to cause a relatively thin layer of a cleaning formulation to flow along the surfaces of the teeth at a high enough velocity to produce the required shear stress levels that will result in quick and efficient removal of adhered biofilms.

Figure 4B:
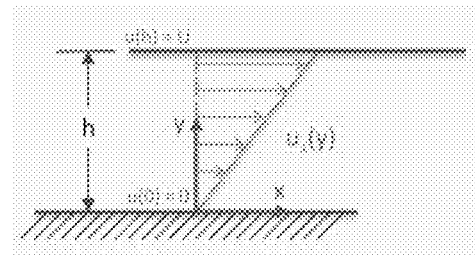
FIG. 4B illustrates a flow pattern between a moving surface and a stationary surface.

A method to produce a flow in a thin layer of fluid on an open surface is taught by observation of the behavior of a layer of fluid interposed between two closely spaced parallel plates, one of which is moving relative to the other. The fluid layer adjacent the stationary plate has zero velocity at the plate surface, relative to the stationary plate. The fluid layer adjacent the moving plate has a zero velocity at the plate surface relative to the moving plate. From the reference of the stationary plate, there is therefore a velocity gradient within the thickness of the fluid between the plates, and thus there are shear stresses at the plate to fluid boundaries. Relative to the stationary plate, there is a net mass flow of material along the fixed plate surface. This shear induced flow is illustrated in FIG. 4B.

In a first embodiment of a tooth cleaning device to effectively utilize a formulation of nanoscale cellulosic fibers suspended in a gel, for removing biofilm from tooth surfaces, an applicator having a relatively flat surface with a plurality of shallow indentations, or pockets is attached to a lateral face of an elongated handle element, proximal an end of the handle element, the surface indentations oriented away from the lateral face of the handle element. The applicator may be manufactured from a resilient flexible material such as a compression molded silicone rubber of fairly low durometer, having at least one shallow indentation in its face. Alternatively, the applicator might be manufactured by slicing segments of a closed cell foam material, extruded in the form of a bar with an ovate cross section. When crosswise sliced, the foam cells at the newly created surface, having been cleaved, will present a surface with a plurality of partial spherical cells forming shallow indentations in the newly exposed surface.

In use, the described tooth cleaning device may first have a quantity of a cleaning formulation applied to the applicator surface. The applicator may then be introduced into the mouth, with the applicator surface pressed lightly against the surfaces of teeth to be cleaned, and the applicator may be manually moved or oscillated along the tooth surfaces. The oscillatory motion of the applicator over the stationary surface of the teeth, may induces Couette flow of the cleaning formulation in the shallow recesses of the applicator, resulting in sufficient shear stress upon the biofilm to defeat the adhesion of the biofilm to the tooth surface.

Figure 3B:
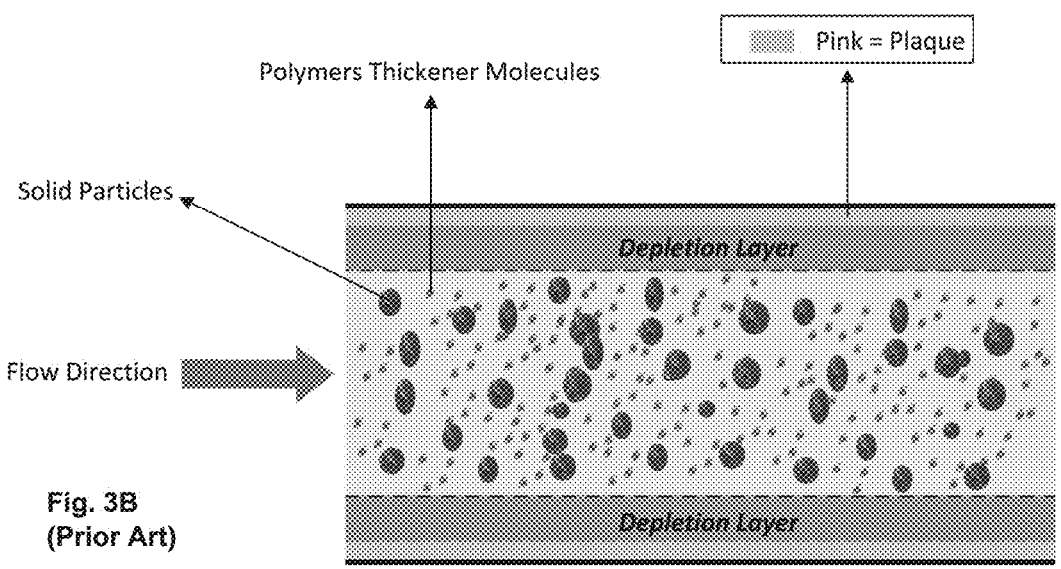
FIG. 3B is a schematic illustration of the situation of a conventional toothpaste being pushed between teeth and passing through the interproximal space.
Figure 3C:
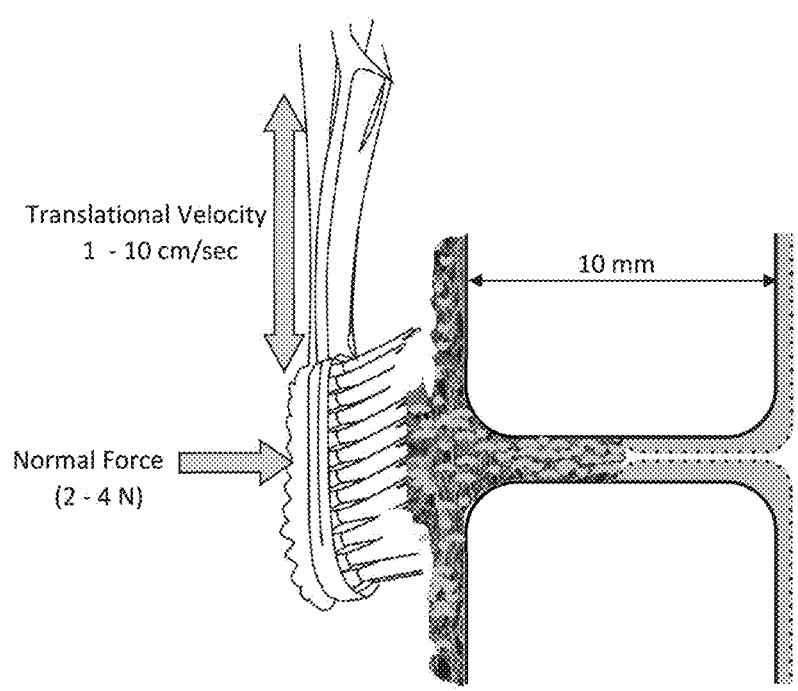
FIG. 3C is a schematic illustration of a composition of an embodiment of the invention being pushed into the interproximal space.
Figure 3D:
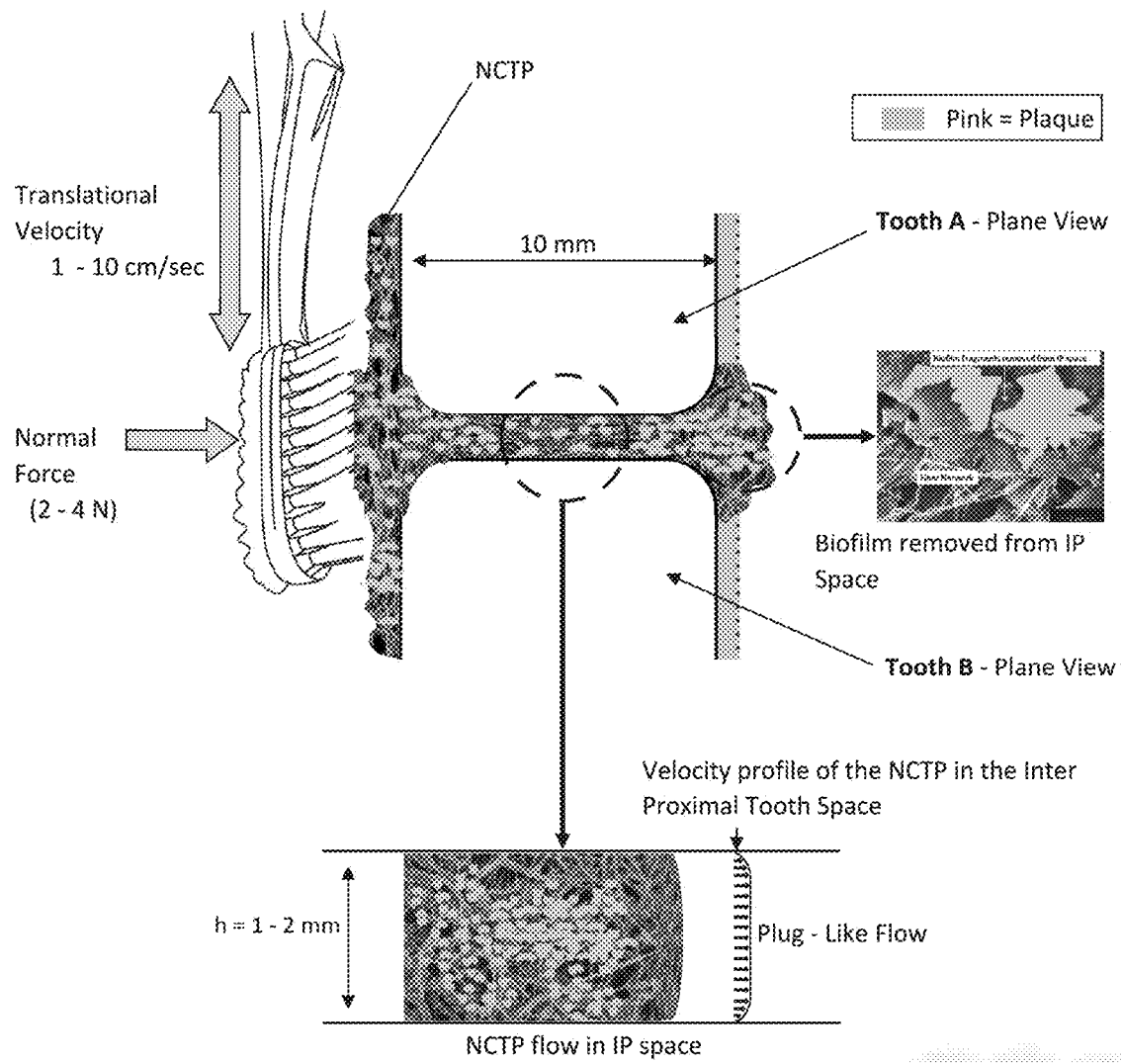
FIG. 3D is a schematic illustration of a composition of an embodiment of the invention

Referring now to FIG. 3A-3D, there are shown several possible modes of action of toothbrushing for reaching interproximal spaces, both for toothbrushing with conventional toothpastes and for toothbrushing with compositions of embodiments of the invention. As shown in FIG. 3A, in toothbrushing with conventional toothpaste, the brush might urge some amount of toothpaste into the interproximal space, but whatever solid particles are contained in conventional toothpaste experience a depletion layer of fluid flow adjacent to the tooth surface during the flow through the interproximal space, and as shown in FIG. 3B, do not make good contact with the interproximal surfaces. In contrast, as shown in FIG. 3C, toothbrushing may force inventive compositions through the interproximal space. Because of the more plug-like velocity profile for flow of the inventive composition, the solids of the inventive composition make good contact with the interproximal surfaces and effectively remove plaque from those surfaces.

Figure 3E:
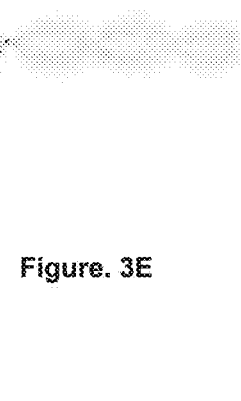
FIG. 3E is an illustration of an impingement device delivering a composition of an embodiment of the invention to impinge against a surface of a tooth.

Referring now to FIG. 3E, there is shown an impingement type device for use with compositions of embodiments of the invention. In connection with jetted applications of the composition, an applicator with a slit or orifice geometry could be useful for propelling the composition into the interproximal space, and the locally high shear at the orifice/slit could cause the viscosity to drop enough for fluid to flow from the orifice into interproximal space. Flow and forces generated in interproximal space are believed to be sufficient to remove biofilm. Such a composition would be thinner than commercial toothpaste and its shear-thinning properties would help it to impinge. The shear thinning properties can be adjusted based on the concentration of ingredients as described elsewhere herein. A composition of an embodiment of the invention has been tested in a commercial AirFloss device and it works nicely. We found that Nano-Clean toothpaste cleaner can be delivered by the Phillips AirFloss and can remove biofilm from hydroxyapatite substrates as described elsewhere herein. It is helpful if the composition includes friction elements such as MicroCrystalline Cellulose, silica, calcium carbonate particles or the like. It is possible to select the particle size of the friction elements to be small enough to flow between teeth. For example, the MCC particles can be 25 microns to maximum of 100 microns overall dimension. For example, substantially all solid particles in the composition may have a maximum dimension that is smaller than a typical spacing between human teeth at a gumline.

Figure 4C:
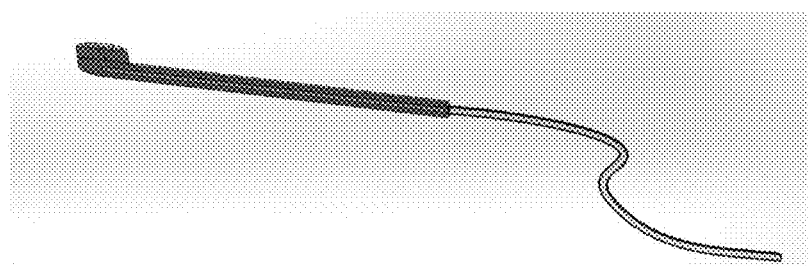
FIG. 4C illustrates a toothbrush having a supply tube for delivery of cleaning composition.
Figure 4D:
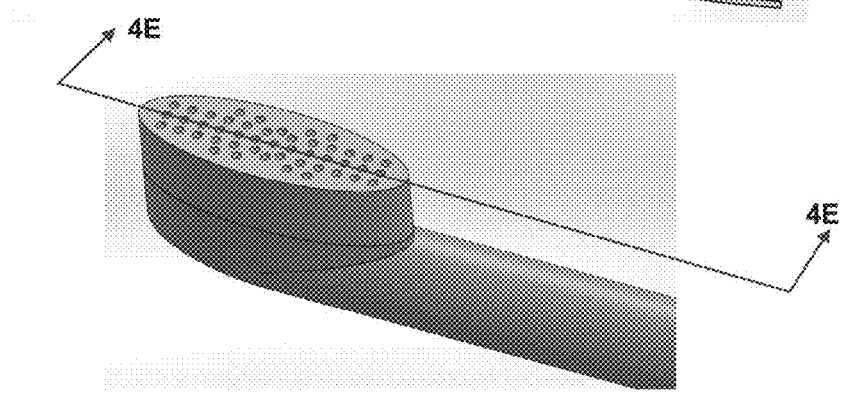
FIG. 4D is a close-up of FIG. 4C.
Figure 4E:
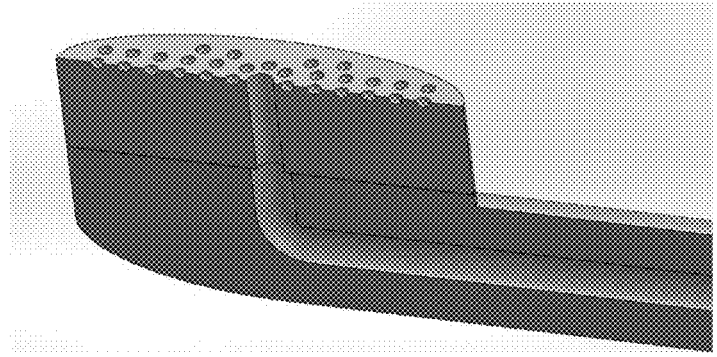
FIG. 4E is a cross-section of FIG. 4D.

Referring now to FIGS. 4C-4E, in another embodiment of a tooth cleaning device, the elongated handle element may be provided with an interior conduit, the conduit receiving at a first end, means to supply and dispense the cleaning formulation through the conduit, to a port central to the lateral face of the handle element where the applicator element is to be attached, the applicator element now manufactured and attached with a central port which aligns with the port of the handle element. In this embodiment, the cleaning formulation may be dispensed through the conduit in the handle element, through the port in the handle, and then through the port in the applicator, to the surface of the applicator, either periodically, or continuously, to replace cleaning composition material that is lost or diluted from the applicator face during the cleaning of the teeth.

In this embodiment, means to supply and dispense a cleaning formulation may comprise a simple flexible tube filled with the cleaning formulation, connected, either directly or be means of a flexible tube, to the conduit of the handle element, and manually squeezed to dispense the cleaning formulation through the conduit, through both ports, to the surface of the applicator element.

Alternatively, the means to supply and dispense a cleaning formulation may comprise a rigid chamber, having a variable volume, which is connected, either directly or be means of a flexible tube, to the conduit of the handle element, and operated to displace cleaning formulation from the chamber, through the conduit, through both ports, to the surface of the applicator element. Operation of such a variable volume dispensing mechanism may be done manually, or by means of a power source, such as an electric motor.

As yet another alternative, the means to supply and dispense a cleaning formulation may comprise a pump, the discharge of which is connected, either directly or be means of a flexible tube, to the conduit of the handle element, and the intake of which is connected to a reservoir containing the cleaning formulation. Operation of such a pump will displace cleaning formulation from the reservoir, through the pump, through the conduit, through both ports, to the surface of the applicator. Operation of such a pump may be continuous or intermittent.

In a third embodiment of a tooth cleaning device, the handle element of embodiment one is affixed to an actuator unit which moves the handle element in an oscillatory motion relative to the actuator unit. A user now grips the actuator unit, using the actuator unit to position and guide the applicator, the actuator unit now providing the oscillatory motion of the applicator element as required for tooth cleaning.

In a yet another embodiment of a tooth cleaning device, the handle element of embodiment two is affixed to an actuator unit which moves the handle element in an oscillatory motion relative to the actuator unit. A user now grips the actuator unit, using the actuator unit to position and guide the applicator, the actuator unit now providing the oscillatory motion of the applicator unit as required for tooth cleaning.

In a yet another embodiment of a tooth cleaning device, an elongated handle element has means to receive near one end of the handle element, a rotary applicator element, the means to receive a rotary applicator element rotatable about an axis approximately normal to the axis of the handle element. Mechanism within the elongated handle element is provided to cause rotation of the means to receive a rotary applicator element, and thus the attached rotary applicator. Operation of the mechanism may be from manual input, or, preferably by a power source such as an electric motor. Rotation of the means to receive a rotary applicator element may be in a single rotary direction, or the direction of rotation may periodically change, during the tooth cleaning process.

The rotary applicator element is preferably manufactured from a resilient flexible material such as a compression molded silicone rubber of fairly low durometer, having at least one shallow indentation in its face. Alternatively, the applicator might be manufactured by slicing segments of a closed cell foam material, extruded in the form of a rod with a cylindrical cross section. When crosswise sliced, the foam cells at the newly created surface, having been cleaved, will now result in a surface with a plurality of partial spherical cells forming shallow indentations in the newly exposed surface.

In use, the tooth cleaning device will first have a quantity of a cleaning formulation applied to the rotary applicator surface. It will then be introduced into the mouth, with the rotary applicator surface pressed lightly against the surfaces of teeth to be cleaned, and the rotary applicator will be rotated while the user moves the rotary applicator along the tooth surfaces.

The rotary motion of the rotary applicator over the stationary surface of the teeth, induces Couette flow of the cleaning formulation in the shallow recesses of the applicator, resulting in sufficient shear stress upon the biofilm to defeat the adhesion of the biofilm to the tooth surface.

In a yet another embodiment of a tooth cleaning device, the device of the previous embodiment may be provided with a channel extending through the elongated handle element, through the means to receive a rotary applicator element, through the rotary applicator, to the surface of the rotary applicator, such that any of the aforementioned means to supply and dispense a cleaning formulation to the surface of an applicator, may be used to supply and dispense a cleaning formulation to the surface of the rotary applicator in this embodiment.

While the just-described embodiments of a tooth cleaning device described above effectively remove biofilm from the facial, lingual, and occlusal surfaces of the teeth, the interproximal surfaces might not be effectively cleaned by these devices. With the some of the embodiments of a tooth cleaning device, any motion of the applicator may be halted, and with the central port of the applicator, or the channel through the rotary applicator positioned adjacent the interproximal space between two teeth, the means to supply and dispense a cleaning formulation may actuated, to produce a flow of the cleaning formulation through the interproximal space. In such a situation, the flow may have a large enough velocity gradient to produce sufficient shear stress upon the biofilm to defeat the adhesion of the biofilm to the tooth surface even in interproximal space.

If positive displacement means to supply and dispense a cleaning formulation, such a rigid chamber, having a variable volume, or a positive displacement pump are used to produce the flow of the cleaning formulation through the interproximal spaces, then the pump can be reversed, resulting in a reversal of the flow through the interproximal space. By rapidly alternating the flow direction, the interproximal space may be efficiently cleaned, with a minimal total amount of cleaning formulation.

To make up for lost cleaning composition that may be washed away, and for dilution by saliva, the pumping means can be operated with asymmetric discharge and intake cycles, resulting in a small net positive flow through the interproximal space. It is further possible to use an electromagnetic coil to cause oscillations in the flow, while the pump provides the desired net flow.

By repositioning the applicator, alternate portions of the tooth surface will form the enclosing surface, and thus will be cleaned. To increase the size of the enclosing surface, the area of the open top of the channel may be increased by making the channel wider, or longer, and/or by employing multiple channels on the face of the applicator. Channel length may be increased by folding the channel back and forth on the applicator surface, in a serpentine pattern, or by creating the channel in a spiral pattern on the applicator surface. An embodiment of the invention can comprise a tooth cleaning device, having an applicator, in which the applicator has a surface with at least one shallow indentation, the at least one shallow indentation filled with a cleaning formulation, the cleaning formulation containing nanoscale cellulosic fibers, with the applicator being placed against and moved along the surface of a tooth. An embodiment of the invention can comprise a tooth cleaning device, having an applicator, in which the applicator has a surface, the surface having at least one shallow channel, wherein the applicator is placed against the surface of a tooth, a portion of said surface of a tooth forming closure of said at least one shallow channel, wherein the cleaning device having means to direct a flow of cleaning formulation through the at least one shallow channel and along the portion of said surface of said tooth, wherein the cleaning formulation contains nanoscale fibers such as cellulosic fibers. If the cleaning composition is delivered continuously during toothbrushing, or is delivered at various times during toothbrushing, that could counteract the problem of dilution because the cleaning composition would be delivered at more than just the start of brushing and its concentration could be maintained during brushing.

Mouthwash

In still other embodiments of the invention, the composition of the invention can be a mouth wash or mouth rinse formulated such that it can be made to flow in the interproximal space and remove dental plaque from surfaces in-between teeth as well as from the surface of teeth. We have discovered by microscopic examination that when the NanoClean toothpaste cleaner composition is diluted to 10% or less of its original concentration, it still retains its 3D network microstructure, and we have discovered that at such concentration it can still remove biofilm from surfaces. The concentration of the fibers and fibrils as well as of the friction elements can be sufficient to remove plaque with the movement of the fluid during mouth rinsing. The hydrodynamic flow generated from swishing the fluid around the mouth can provide the driving forces for hydrodynamic flow. Alternatively, an applicator such as Waterpik® or AirFloss® or other device can be used to cause flow of the composition over tooth surfaces or in the interproximal spaces or along the gum line during application or cleaning.

The properties of a mouthwash of embodiments of the invention may be similar to the properties already discussed for NanoClean toothpaste cleaner, except that the concentrations of various ingredients may be more dilute, and viscosity and related physical properties may be smaller. For example, the water concentration can be greater than 85%, greater than 90%, and can be about 90% to about 95% to provide the desired flow properties.

In the use of a mouthwash, the motion may come from swishing the mouthwash in the user's mouth, rather than from externally supplied motion of a brush. This mechanism does not preclude the use of a brush especially the ultrasonic brushes on the market that can induce flow patterns to force the fluid into the interproximal spaces and into difficult to reach area such as the gum line and the back portion of the mouth or in the interior sides of teeth. The mouthwash can be formulated so that it still is sufficiently concentrated so as to retain some or all of its 3D network structure so that it remains effective to remove biofilm but is not so thick as to prevent flow into and within the interproximal space, or other small-dimensioned spaces or regions. The composition of mouthwash can be adjusted based on expected shear rate encountered during mouth washing which many be in the range of 20 to 1,000 inverse seconds or more.

AirFloss or Jetting or Impingement or Hydrodynamic Flow

An embodiment of the invention can include introducing into the interproximal space an inventive composition having physical properties of mouthwash or of toothpaste or anywhere in between. An embodiment of the invention can include jetting of the composition under pressure at interproximal spaces or any other location including the gum line. An embodiment of the invention can include air flossing, in which controlled amounts of a fluid composition are propelled by puffs of gas into locations such as the interproximal spaces or into any other location including the back of teeth and other difficult to reach spaces or regions of the mouth. It can include liquid jetting or impingement as a continuous or pulsed jet of liquid. The impingement mode can be programmed or actuated on demand as desired so as to achieve optimal plaque removal.

A typical NanoClean tooth cleaner formulation such as a composition containing 0.7% MFC and 0.7% SAP and 1% MCC, or other formulation as described elsewhere herein, can be used in AirFloss. An air pump can sufficiently pump the composition because the composition is a shear thinning fluid and can provide sufficient flow between teeth to remove biofilm. The shear-thinning property of the inventive composition is helpful in achieving this.

In embodiments of the invention, the composition can be formulated so as to prevent or discourage formation of aerosol, i.e., the composition can have rheological properties such that it is not so thin as to easily form aerosol. In order to prevent aspiration into lungs, it would be undesirable to create droplets of respirable size such as less than 5 microns diameter.

Composition Intermediate Between Mouthwash and Toothpaste

In still other embodiments of the invention, a composition may be provided that has properties intermediate between those of toothpaste and those of mouthwash. In general, the properties of such a composition could be such as to resemble syrup. While this may be a novel texture for the user, its effectiveness can motivate the user to try this new texture. This intermediate composition can be used in some situations such as during traveling, hiking or in a hospital setting where some patients cannot brush their teeth such as for stroke patients or the like.

Chewing Gum

Chewing gum can be a substance that has elasticity and large elongation and is not brittle. A chewing gum substance could for example be a wax substance, or xanthan gum or gum Arabic or the like or synthetic polymers. Currently, chewing gums do not include fibers in them. An embodiment of the invention can comprise a chewing gum substance in combination with polymeric fibers during chewing will give friction that erodes biofilm. It could further contain friction elements, which will give similar to NanoClean tooth cleaner. The concentration of MFC or MFC+MCC can be sufficient to induce friction but not so high as to shed in the mouth; the fibers and possible friction elements should remain occluded in the chewing gum mass. For example, the concentration of these additives might be less than 1% (wt/wt) concentration of MFC and less than 1% concentration of MCC, with the remainder being chewing gum base. The chewing gum may include fluoride, xylitol or another agent to remove and retard the formation or regrowth of the dental biofilm during and after the act of chewing, in other words it can provide persistence during and after use.

Interproximal Brush

In addition to the exposed large surfaces of the teeth, another area that desirably is cleaned is the interproximal spaces between teeth. Embodiments of the inventive composition can be used in any form that accesses the interproximal space.

A composition of an embodiment of the invention could be useful for achieving cleaning of interproximal spaces (between teeth) by a brushing action. An interproximal brush may be sort of a miniature brush having bristles, having dimensions that are small enough to fit between teeth. A composition could be loaded onto an interproximal brush as a manufactured product. Such interproximal brush could comprise, pre-loaded onto it, a composition of an embodiment of the invention, or a dehydrated form thereof. Alternatively, it would be possible to use a commercial InterProximal brush by applying to the interproximal brush, at the time of use, a toothpaste of an embodiment of the invention, or a mouth wash or mouth rinse of an embodiment of the invention, or a substance intermediate in properties between toothpaste and mouth wash or mouth rinse.

Alternatively, such an interproximal brush may be an open, or closed cell foam as described herein. Such foam may be cut so as to expose open cells on its surface, with composition being deposited on or in the open, closed, or interconnected cells at the surface or within the bulk of the device.

Application to Interproximal Spaces Via Dental Floss or Dental Tape

A composition of an embodiment of the invention, or a dehydrated form thereof, could be loaded onto dental floss or dental tape. Such a composition can be loaded or coated on the body of the dental floss or dental tape and in interstices of a porous or textured dental floss or dental tape. It is also possible that the dental floss or tape itself can be such that its central tensile-load-bearing member can comprise fibers or fibrils attached to it or integral with it. This dental floss or tape itself could made of fibers that are frayed, textured, porous, absorbing or fibrillated, which may cooperate or entangle with the fibrils and other ingredients of the inventive composition.

When the composition becomes hydrated in the mouth it becomes active in removing dental biofilm from the interproximal space. The composition can comprise similar or the same composition as embodiments of the invention for other applications, i.e., it can have ingredients such as MFC network, friction elements, abrasive particles, fluoride and other ingredients.

Applicator Comprising Closed Cell or Open-Cell Foam

In an embodiment of the invention, there may be provided an applicator together with the inventive composition loaded onto the applicator. The applicator may be made of or may comprise a foam. The foam may be a closed cell foam, in which some open cells are created at the surface of the applicator by cutting through at least some of the originally-closed cells that are located where the cut is made. The composition of an embodiment of the invention may reside in these exposed cut-open cells at the surface. The applicator may be in the form of a conventional toothbrush, an interproximal brush, or any other appropriate shape including dental floss or dental tape or finger sleeve applicator (which is dimensioned to slip over a finger and deliver dentifrice to the oral cavity). It is possible that the applicator could further comprise a structural element that is made of something other than foam such as textured rubber or plastic or an absorbing pad. The structural element could be stiffer than the foam. It is also possible that instead of starting with a closed cell foam, the applicator could be made of or could comprise an open cell foam or a sponge that can retain the composition and deliver it when applying normal or other directional forces.

A typical closed cell foam is commonly known as Polyethylene Foam. It has white color and is widely used in electronic appliances, instrumentation, computers, audio, medical equipment, industrial chassis, lighting, handicrafts, glass products, ceramics, Wine, gifts, hardware, electrical and mechanical, precision instruments, toys, fruits, shoes, daily necessities and other products packaging.

Alternatively, an open cell foam could be used. The open cell foam could be saturated with the composition. It would be possible to squeeze some of the composition out during use by squeezing the foam. The squeezed composition can be made to flow in the InterProximal spaces to clean them during the application. A convenient applicator can be a finger sleeve to permit manipulating the composition in different regions of the mouth including the InterProximal spaces, back of teeth and surface of the tongue.

Method of Cleaning Teeth of an Embodiment of the Invention

Embodiments of the invention also comprise a method of cleaning teeth. The method can comprise applying a composition of an embodiment of the invention onto a toothbrush and brushing teeth, likely followed by rinsing. The toothbrush may be a manual toothbrush, a rotary toothbrush, an ultrasonic toothbrush, any other type of toothbrush or applicator described herein, or generally any type of toothbrush.

Embodiments of the invention also comprise a method of cleaning teeth using any of the applicators described herein other than a toothbrush.

Embodiments of the invention also comprise a method of cleaning teeth using a mouthwash, a composition intermediate in properties between a mouthwash and a toothpaste, or a chewing gum.

Embodiments of the invention also comprise a method of cleaning teeth using an impingement device in combination with compositions of the invention.

Methods and Measurement Techniques Used for Experimental Results Reported Herein For various experimental results reported here, it is appropriate to first describe the protocols, equipment and techniques used. Testing used two types of testing. One type of testing which involved measuring actual removal of biofilm under standardized conditions which involved biofilm but not actual teeth. Another type of test involved making rheological and tribological measurements of a type that is standard in those fields, which describe macroscopic physical properties of various toothpaste compositions, not involving biofilm.

In regard to microscopic and direct testing, one type of test performed, which is believed to be representative of the actual toothpaste function of removing plaque biofilm, is a test about removing biofilm from the internal surface of a tube by flow under controlled conditions. The biofilm is grown under controlled repeatable conditions. The tube is transparent and the biofilm is stained prior to the experiment so that it can easily be seen whether the biofilm is removed or not.

In experiments (in a tube geometry) described herein, experiments show that at their nominal formulation, compositions of embodiments of the invention have an ability to remove biofilm, and corresponding experiments show that some of conventional toothpastes do not have the same ability. Furthermore, these same experiments show that upon dilution to 50% concentration, compositions of embodiments of the invention still have an ability to remove biofilm, while none of the commercial toothpastes retain that ability to remove biofilm at 50% dilution.

In addition, experiments were performed of rheological and tribological properties of toothpaste formulations. These experiments measure bulk properties that are believed to have at least some relation to the cleaning ability of a formulation. Rheological experiments can measure properties such as G' (elastic modulus or storage modulus), G" (loss modulus), viscosity and yield shear stress (in the case of a gel). Tribological measurements can measure the friction factor of one surface of the instrument interacting with another surface of the instrument, in the presence of the composition being tested, at various relative velocities.

It is believed that it is helpful for the composition to have G' in a certain range described herein, so that the composition engages biofilm and performs a peeling action. It is believed, in general, that it is better for the composition to have a larger rather than a smaller friction factor. It is believed that possessing preferred values of such properties increases the likelihood that a composition will clean well. However, it also is believed that possessing preferred values of such properties is not in itself a guarantee that a composition will be effective in cleaning.

Measurements described herein show that in regard to rheological and tribological properties, compositions of embodiments of the invention have G' larger than 1500 Pa, and have yield stress greater than 10 Pa, and have friction factor (measured against Teflon) of greater than 0.15 or greater than 0.2. These are believed to be desirable values of these macroscopic physical parameters. In various ways these macroscopic physical parameters differ from the ranges of conventional toothpastes. It can be noted that in conventional toothpastes, achieving these values is accomplished using macromolecular polymeric thickeners as opposed to the fibrils and other additives of embodiments of the invention. This involves different size scales. Molecules of the macromolecular polymeric thickeners have a size scale of the order of 2 microns at most. The fibrils of embodiments of the invention, which provide a thickening effect, have diametral dimensions that are in the range of 20 nm to 75 nm. Furthermore, upon dilution to 50% concentration, compositions of embodiments of the invention still maintain desirable values of these macroscopic physical parameters, while commercial toothpastes diluted to 50% concentration do not maintain desirable values of these macroscopic physical parameters.

Protocol for Growing Biofilm Inside Tubes

One form of experiment is to grow biofilm inside tubes and then flow compositions through the tubes to see how well biofilm is removed. The tube is made of polytetrafluoroethylene or a similar polymeric material typically used for flexible tubing. It also is possible that the tubes could be made of rigid hydroxyapatite. This geometry is used with flow, through the tube, of candidate toothpaste formulations or of existing commercial toothpastes, either with the formulation as intended for use, or with the formulation diluted with water.

In some instances, the biofilm is grown from $S.$ $mutans$ bacteria. In some instances, the biofilm protocol is such as to produce a particularly tough form of biofilm referred to as "Build up Biofilm" (BBF). This biofilm is encountered in situations of medical device disinfection, when biofilm is growing and is occasionally exposed to the disinfectant glutaraldehyde. The disinfectant has the effect of making the remaining biofilm tougher and such biofilm becomes more difficult to physically remove. This is described in Alfa et al. [Reference: A novel PTFE-channel model, which simulates low levels of culturable bacteria in build-up biofilm after repeated endoscope reprocessing. Alfa et al., Gastrointestinal Endoscopy 85(5), Supplement, pp. AB67-AB68, 2017]. BBF was made according to the protocol set forth in U.S. Pat. No. 10,266,793 (such as Table 16).

Protocol for ATS

ATS soil as developed by Alfa (U.S. Pat. No. 6,447,990) (Artificial Testing Soil (ATS) as published by Alfa et al. (Ref "Alfa et al., 2010. EVOTECH® endoscope cleaner and reprocessor (ECR) simulated-use and clinical-use evaluation of cleaning efficacy, BMC Infectious Diseases. BMC Infectious Diseases 2010, 10:20 www.biomedcentral.com/1471-2334/10/200)") was used as a surrogate to indicate medical device cleaning by measuring remaining protein, carbohydrate and hemoglobin in the tube or channel after cleaning as per the protocol described elsewhere herein.

Protocol for Rheological Testing of Toothpaste Using Parallel Plates

Rheological properties, i.e., viscosity, shear stress, elastic and viscous moduli are measured with a rotational shear rheometer (Anton Paar MCR 302) by imposing a given (shear) stress to the fluid, and from assumed relationships between stress and deformation, the mechanical properties are determined. In the rheometer, the material is loaded between two parallel plates of 50 mm diameter, one of which is fixed and the other of which is rotatable with respect to the first. The gap between the plates can be between 0.3 mm and 1.5 mm, depending on the fluid to be measured. The shear stress (measured in Pascal, Pa) in this geometry is calculated as:

$$\tau_{PP} = \frac{M}{2\pi R^3}\left[3 + \frac{d\ln M}{d\ln \dot{\gamma}}\right],$$

where R is the radius of the plate, M the torque applied to rotate the upper plate and $\dot{\gamma}$ the average shear rate (measured in $s^{-1}$). Among the parameters characterized are the viscosity (through the ratio between shear stress and shear rate, measured in Pa s or mPa*s), elasticity (through the elastic modulus G', measured in Pa), viscous modulus (G", measured in Pa), yield stress (that is defined as the minimum amount of stress needed to put the fluid in motion and is measured through a shear stress ramp, measured in Pa).

Protocol for Tribological Testing of Toothpaste

Tribological properties are properties concerning lubrication, friction and wear. The tribological properties of the toothpaste can be measured with the Anton Paar instrument set up with a ball (made of glass, stainless steel or other materials) rotating on the fixed surface of three flat round pins (made of Teflon, polydimethylsiloxane, metal or other materials). The pins have a diameter that is smaller than the ball diameter. The pins form a 45-degree angle ($\alpha$) with the rotating ball. In the tribometer, the fluid is sandwiched between the rotating ball and the pins and the whole ball plus pins system is immersed in a reservoir filled with the fluid. A normal force load ($F_N$) ranging from 1 N to 100 N Newton is applied to urge the ball against the pins, while the ball is rotated. The friction factor $\mu$ is calculated as $$(F_F = \frac{M}{3r\sin\alpha}),$$

where M is the torque applied to rotate the ball) needed to put the ball in motion at a given sliding velocity (up to a few cm/s) in the presence of the applied normal force on the pins $$\left(F_{N,tribo} = \frac{F_N}{3\cos\alpha}\right),$$

therefore $$\mu = \frac{F_F}{F_{N,tribo}}.$$

It can be noted that the friction factor is descriptive of the fluid but also it is a function of the substance of which the ball and the pins are made.

Procedure for Preparing Inventive Toothpaste Composition

TABLE 3 of Example NCTP composition

| Toothpaste #3 Formulation: | wt. % |
|---|---|
| Sodium saccharin | 0.300 |
| Sucralose | 0.050 |
| Sodium fluoride | 0.243 |
| Sodium lauryl sulfate (SLS) | 0.150 |
| Cocamidopropyl betaine (35%) | 0.150 |
| Peppermint flavor | 0.500 |
| Microfibrilated cellulose (MFC) | 1.750 |
| Microcrystalline cellulose (MCC) | 1.000 |
| Sodium polyacrylate (surface cross-linked) (SAP) | 0.500 |
| Titanium dioxide | 0.220 |
| Hydrated silica abrasive | 10.000 |
| Hydrated silica thickener | 3.000 |
| Distilled water | 82.137 |

| Preblend 1: | wt. % |
|---|---|
| Sodium saccharin | 0.300 |
| Sucralose | 0.050 |
| Sodium fluoride | 0.243 |
| Water | 11.407 |
| Total | 12.000 |

| Preblend 2: | wt. % |
|---|---|
| Sodium lauryl sulfate (SLS) | 0.150 |
| Cocamidopropyl betaine (35%) | 0.150 |
| Peppermint flavor | 0.500 |
| Water | 4.200 |
| Total | 5.000 |

| Preblend 3: | wt. % |
|---|---|
| Microcrystalline cellulose (MCC) | 1.000 |
| Microfibrillated cellulose (MFC) | 1.750 |
| Sodium polyacrylate(surface cross-linked)(SAP) | 0.500 |
| Hydrated silica abrasive | 10.000 |
| Hydrated silica thickener | 3.000 |
| Water $1^{st}$ (comes from MFC; MFC:Water = 1:9) | 9.000 |
| Water $2^{nd}$ | 57.530 |
| Total | 82.780 |

| Master Batch: | wt. % |
|---|---|
| Preblend 1 | 12.000 |
| Preblend 2 | 5.000 |
| Preblend 3 | 82.780 |
| Titanium dioxide | 0.220 |
| Total: | 100.000 |

This provides an example on an inventive composition and method of preparing the formulation. The above Table lists the ingredients and their concentration in the inventive composition. The TP3 composition is used demonstrate some of the rheological and tribological specifications of the invention as well as the effect of the dilution.

Method of preparation: Three (3) Preblends were first made separately and then combined together to make the final composition as provided below.

Preblend 1: 1) Dissolve 0.243 parts of sodium fluoride in 11.407 parts of distilled (or deionized) water with mixing; 2) To the clear fluoride solution add 0.3 parts of sodium saccharin and 0.05 parts of sucralose while stirring; 3) Stir the above mixture until clear.

Preblend 2: 1) While slowly stirring add 0.15 parts of Cocamidopropyl betaine (35%) to 4.2 parts of distilled (or deionized) water; 2) While continue to mix slowly, add 0.15 parts of sodium lauryl sulfate (SLS); 3) Stir the above mixture until uniform; 4) Add 0.5 parts of peppermint flavor and increase rate of stirring to form a uniform emulsion.

Preblend 3: 1) Add 1.0 part of MCC, 10.0 parts of hydrated silica abrasive, and 3.0 parts of hydrated silica thickener to 57.53 parts of distilled (or deionized) water and disperse at high speed (#3.5) for 10 minutes until uniform; 2) Add 1.75 parts of MFC to mixture and increase dispersion speed to #5.5 and disperse it for another 15 minutes; 3) Transfer the above mixture to a KitchenAid mixer and add 0.5 part of SAP and mix it at setting #5 for 20 minutes.

Making the Master Batch of the inventive composition: 1) Add 12.0 parts of Preblend 1 and 5.0 parts of Preblend 2 to the above mixture in the KitchenAid mixer and stir it for 5 minutes; 2) Add 0.220 part of titanium oxide and stir it for another 5 minutes; 3) Place the composition in a vacuum chamber to remove any entrapped bubbles or air; 4) Transfer the toothpaste formulation to a glass jar.

Following, in Table 4, are Additional Examples of compositions. Toothpaste 3 contains surface cross-linked Super-Absorbent Polymer, while toothpaste 2 does not contain that ingredient.

Figure 5A:
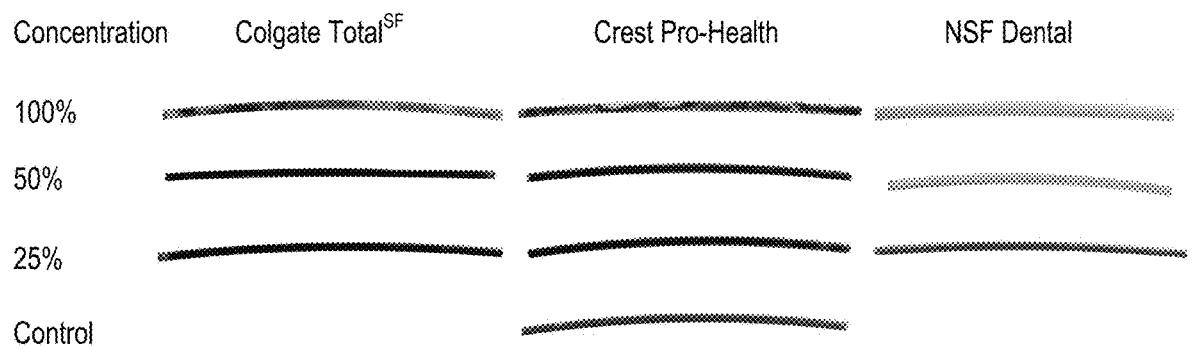
FIG. 5A is a set of tube results for removal of Build Up Biofilm by flow of toothpaste or inventive cleaning composition (NSF), either at full concentration or at various dilutions.
Figure 5B:
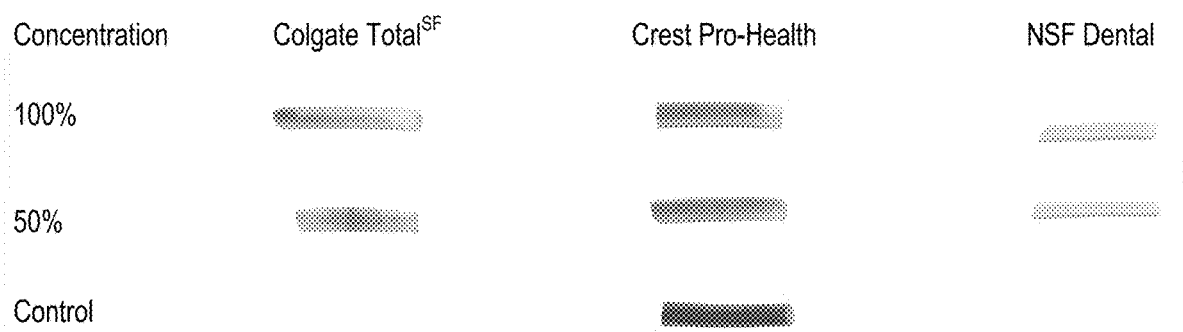
FIG. 5B is a set of tube results for removal of biofilm by flow of toothpaste or inventive cleaning composition (NSF), either at full concentration or at various dilutions.

(NSF) of embodiments of the invention; the control is BBF before cleaning, with Methylene Blue stain. FIG. 5B shows a Comparison of *S. mutans* biofilm removal with Colgate® and Crest® toothpastes vs. composition (NSF) of embodiments of the invention; the control is *S. mutans* biofilm before cleaning, with Rose Bengal stain. The results of this example show that none of prior art toothpastes can remove biofilm even when applied at 100%. In contrast the inventive composition is effective in removing the two types of biofilm even used at 50% concentration. This example highlights the main differences between polymeric thickener-based toothpastes of prior art and the inventive composition which possess a special entangled network that resists dilution and can still provide effective removal of biofilm from surface irrespective of the bacterial species used to make the biofilm.

Figure 6:
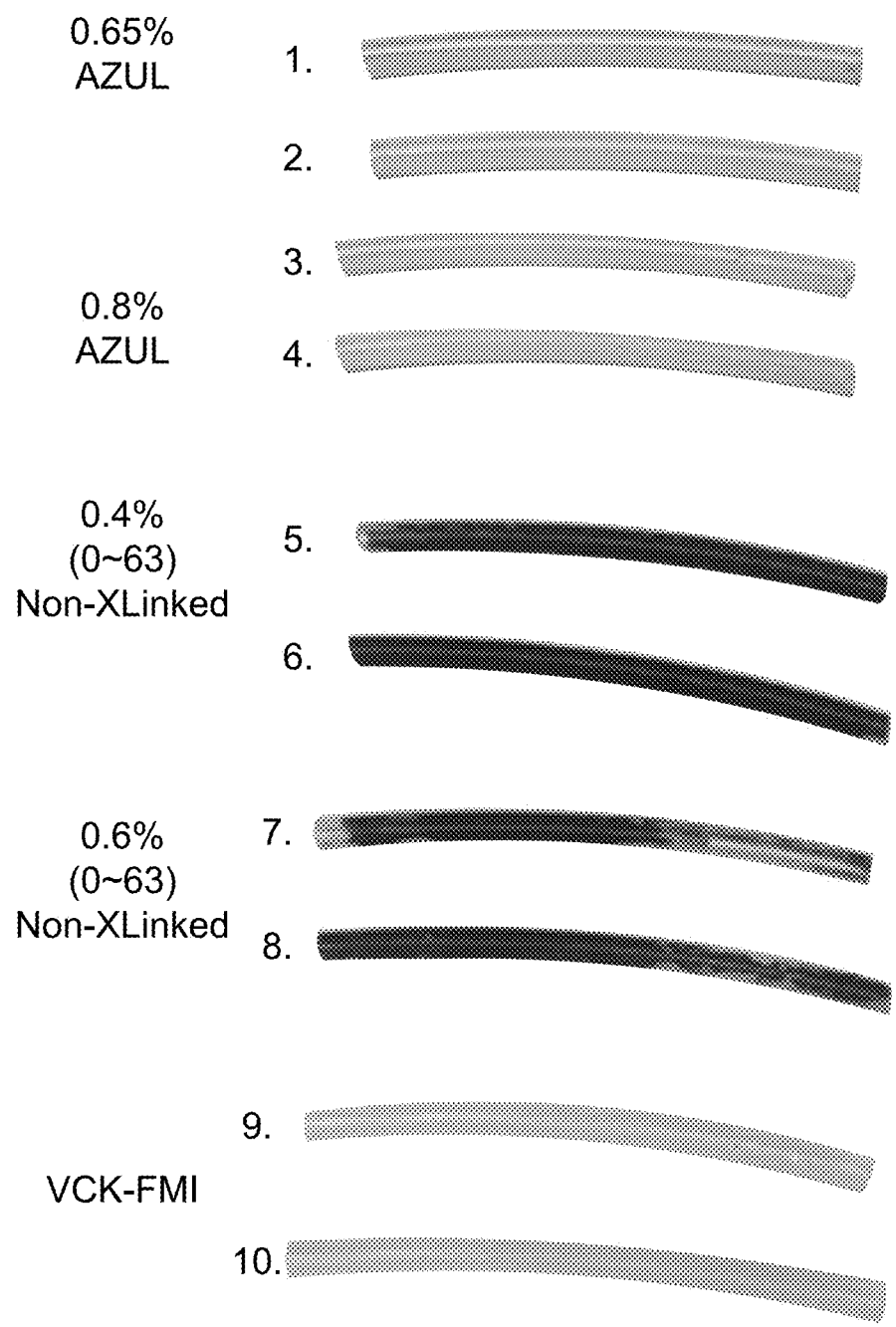
FIG. 6 is a set of tube results for removal of biofilm by the inventive compositions containing particles of SuperAbsorbent polymer that either were or were not cross-linked.

Example 2: Comparison of Two Varieties of SAP: Surface Cross-Linked and not Surface Cross-Linked Referring now to FIG. 6, experiments were conducted about removal of biofilm from the internal surface of a tube. Specifically, these experimental results compare the effectiveness of SAP-containing compositions in which the SAP particles are surface cross-linked, against the effectiveness of SAP-containing compositions in which the SAP particles are not surface cross-linked. It is believed (although it is not wished to be limited to this explanation) that surface cross-linking of SAP particles results in forming sort of a crust surrounding the interior of the SAP particle. It is believed (although it is not wished to be limited to this explanation) that surface cross-linking results in the SAP particles being better able to maintain their irregular shape during flow or

TABLE 4

|  | Toothpaste 1 | Toothpaste 2 | Toothpaste 3 | Toothpaste 4 | Toothpaste 5 |
| --- | --- | --- | --- | --- | --- |
| Sodium saccharin | 0.3 | 0.3 | 0.3 | 0.2 | 0.2 |
| Sucralose | 0.05 | 0.05 | 0.05 | 0.05 | 0.05 |
| Sodium fluoride | 0.243 | 0.243 | 0.243 | 0.243 | 0.243 |
| Sodium lauryl sulfate (SLS) | 0.5 | 0.5 | 0.15 | 0.3 | 0.3 |
| Cocamidopropyl betaine (35%) | 0 | 0 | 0.15 | 0.660 | 0.66 |
| Peppermint flavor | 0.5 | 0.5 | 0.5 | 0.3 | 0.3 |
| Microfibrilated cellulose (MFC) | 1.5 | 1.5 | 1.75 | 1.2 | 1.4 |
| Microcrystalline cellulose (MCC) | 1 | 1 | 1 | 2 | 2.0 |
| Surface cross linked Sodium polyacrylate (SAP) | 0.4 | 0 | 0.5 | 1 | 0 |
| Titanium dioxide | 0.22 | 0.22 | 0.22 | 0.22 | 0.22 |
| Hydrated silica abrasive | 10 | 10 | 10 | 10 | 10 |
| Hydrated silica thickener | 3 | 5 | 3 | 7 | 10 |
| Distilled water | 82.287 | 80.687 | 82.137 | 76.8 | 74.6 |

EXAMPLES

Embodiments of the invention are further described but are in no way limited by the following Examples.

Example 1

An experiment was performed comparing two commercial toothpastes with compositions of an embodiment of the invention. FIG. 5A shows a Comparison of BBF removal with Colgate® and Crest® toothpastes vs. composition motion past the surface being cleaned, and that the SAP particles do not merge into each other, therefore resulting in more effective at cleaning.

In these experiments, a stain of Methylene Blue is used to reveal the presence of biofilm. Clean or transparent means that biofilm has been successfully removed, and blue indicates that biofilm remains. In these photos, the tubes that show blue coloration (biofilm was not removed and remains and absorbs stain) were tubes in which the SAP ingredient of the cleaning composition was not surface-cross-linked.

The tubes that are clear (indicating successful removal of biofilm) are tubes in which the SAP ingredient of the cleaning composition was surface cross-linked. These are samples 1, 2, 3 and 4. Samples 5, 6, 7 and 8 were performed without cross-linking of the SAP, and the stained dark color indicates that biofilm remained after the attempted cleaning process.

Example 3: Deleterious Effect of the Presence of Carboxymethylcellulose

An experiment was conducted which illustrates that the presence of CMC (carboxymethylcellulose) hurts cleaning performance. This is shown in FIG. 7. With a 0.01% concentration (100 ppm) of CMC, there was a little bit of reduction in cleaning performance. With a 0.1% concentration (1000 ppm) of CMC, cleaning was poor. This example shows that common ingredients of prior art toothpaste can deteriorate the frictional properties of the composition and their use may limit to very low concentrations, if they must be used. CMC is a common thickeners of many prior art toothpastes and this may explain as to why they are limited in removing biofilm plaques from teeth.

Example 4

Figure 8A:
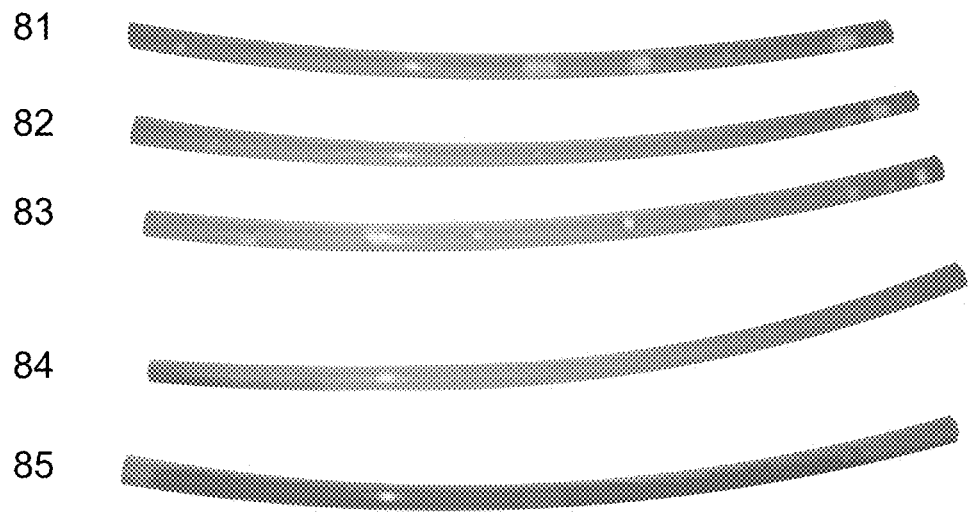
FIGS. 8A and 8B shows results of cleaning internal surfaces of transparent tubes, using a composition of an embodiment of the invention which either did or did not contain glycerin.
Figure 8B:
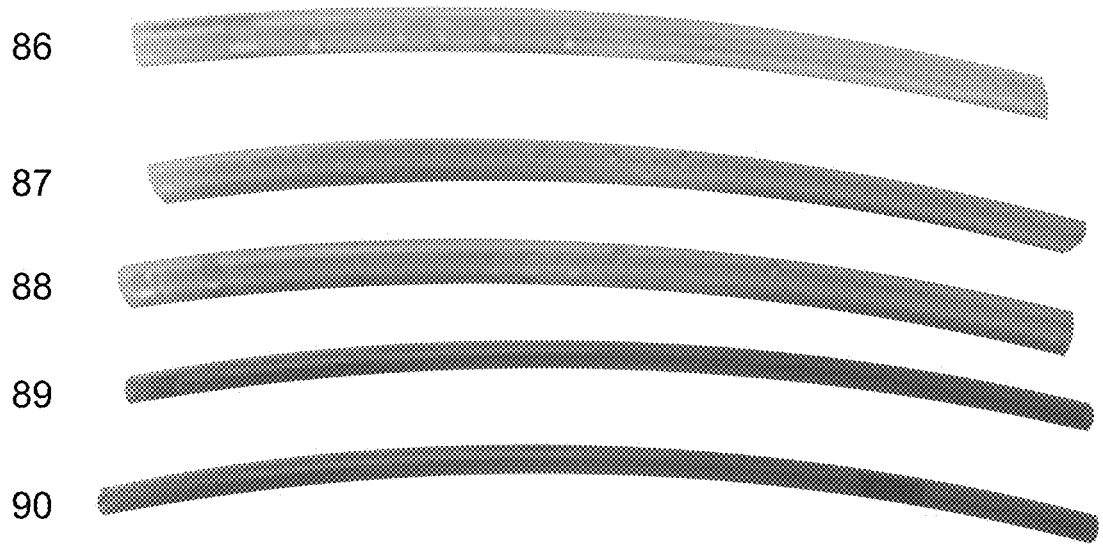

An experiment was conducted which illustrates that the presence of glycerin hurts cleaning performance. The results are shown in FIGS. 8A and 8B.

Most of these samples were cleaned for 5 minutes. The composition used for Samples 81-85 was a standard composition that did not contain any glycerin. Sample #89 contained Glycerin 1.0% (w/w) as an additive and was the only one of these samples that contained glycerin. Sample #89 shows that glycerin very adversely affected cleaning. Glycerin seemed to provide lubricity to the mixture, which was evidenced also by an increased flow rate with a constant supply pressure.

Also in connection with glycerol, we have found that the flow rate of inventive composition containing 1% glycerol increased by a factor of 2 compared to similar compositions made without glycerol. Without wishing to be bound by theory, it is thought that this may be due to the internal lubrication between the fibers and fibrils of the network imparted by glycerol, i.e., the glycerol might be thought of as an internal lubricant. The increase of flow rate in the 3.2 mm inside diameter tube in the presence of glycerol may be due to a decrease in the friction factor when the composition is made to flow under pressure (at a pressure drop per unit length of 1.9 psi/foot) inside the tube. It is also possible that at a 1% concentration of glycerol, the friction coefficient between the biofilm and the composition decreases during flow, and hence the composition slides over such biofilm without effecting its removal. In this context, glycerol may be functioning as both internal and external lubricant, and that such lubrication diminishes the effectiveness of biofilm removal. It is desirable to make biofilm-removal-effective compositions that are essentially free (containing less than 1%) of low molecular weight lubricants/humectants, such as glycerol and the like.

Example 5

The purpose of this example was to compare the removal of S. mutans biofilm from the surface of hydroxyapatite (HA) discs by either water or the inventive composition to simulate the case of actual plaque removal from tooth surface or from interproximal space. To closely mimic dental plaque, we first cover HA discs with pellicle as described below and then allow the biofilm to grow of the discs from several days. The discs were stained blue. The presence of blue indicates lack of removal of biofilm. A white color indicates successful removal of biofilm.

Cleaning in this example was performed by applying the compositions to HA discs by impingement using the commercial AirFloss device made by Philips of the Netherlands which is sold worldwide to clean interproximal spaces between teeth with water.

In each experiment, we fill the compartment of the device with either water or the inventive composition and then deliver one shot of the test fluid onto the surface of HA discs covered by biofilm. The HA discs are then rinsed with sterile water and stained with methylene blue to reveal residual biofilm after application of either water or inventive composition.

As shown in the figures, one single shot of the inventive composition blasts the biofilm away from the surface of HA discs (shown as white areas or bands in photograph) compared to water which leaves a dense uniform biofilm layer (show are uniform blue stain). The results of this example indicate that the inventive composition can be delivered as a jet can remove plaque biofilm the surface of teeth or from the InterProximal space. In an embodiment the inventive composition can delivered by impingement to clean the InterProximal spaces compared to prior art AirFloss or WaterPik. The rheological and tribological properties of the inventive composition are believed to responsible for this effective removal of biofilm from HA surface.

Method for preparing biofilm on HA discs: Biofilms were grown for 4 days in a 12-well plate on hydroxyapatite discs (1.25 cm in diameter, surface area of 2.7±0.2 $cm^2$, Clarkson, Chromatography Products, Inc., South Williamsport, Pa.) in optimized BHI media (BHI broth with hemin (5 mg/lit)+menadione (1 mg/lit)+L-cysteine (1 g/lit), yeast extract).

On the first day, HA disc was placed inside the well with 2000 ml optimized media BHI media (BHI broth with hemin (5 mg/lit)+menadione (1 mg/lit)+L-cysteine (1 g/lit), yeast extract) and inoculated with 500 μl Saliva/plaque for four days. Media were changed every day.

On day 4, 3 HA discs were washed with PBS to remove planktonic cells and were shot with the water, stained with methylene blue (MB) and imaged. Also, 3 HA discs were shot with cellulose, stained with MB and imaged. Also, 3 HA discs were used as a control without any shot.

Pellicle Formation on Discs

To increase pellicle adherence, the discs were etched in 0.12M HCl for 60 sec, soaked in saturated sodium carbonate for 30 sec, followed by 60 sec in 1% phytic acid.

For pellicle formation, the discs were suspended in saturated solution of mucin (about 1.2%) in sRO water at 40° C. for 15 min and slowly cooled to 36° C. in suspension. Subsequently, the discs were removed from the solution and dry in an oven at 37° C. for 30 min. Total 5 cycles of mucin solution at 40° C., cooling down to 36° C. and drying at 37° C. were performed.

Culture Preparation of S. mutans UA159

Single colony of S. mutans UA159 was inoculated to Brain Heart Infusion (BHI) media supplemented with 2% sucrose. The culture was incubated overnight at 37° C. Overnight culture was used to grow the biofilm.

S. mutans UA159 Biofilm Formation on Discs

Pellicle formed discs were soaked in overnight grown culture of S. mutans UA159 and incubated at 37° C. Media was refreshed on a daily basis for 7 days.

Figure 9A:
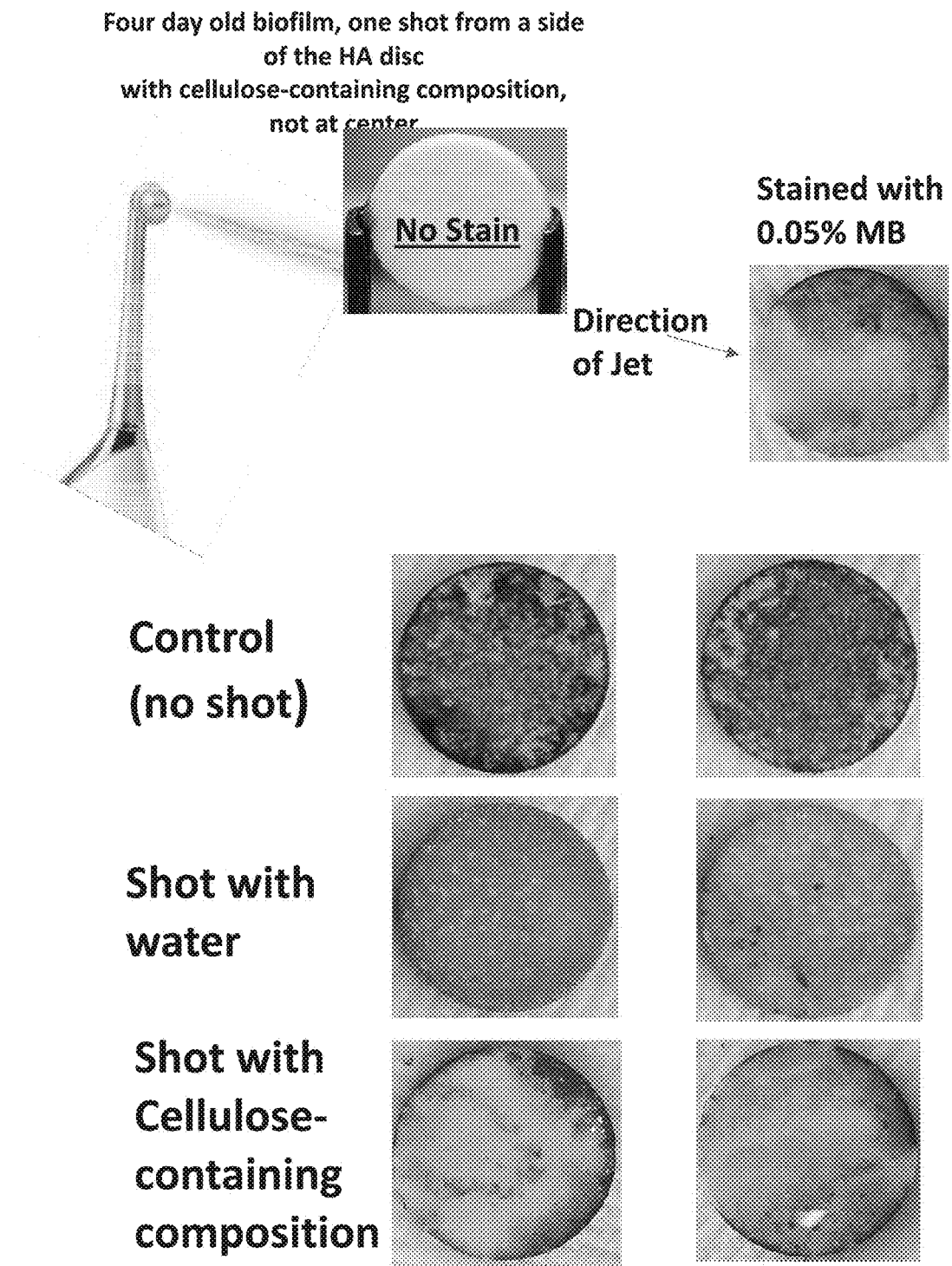
FIG. 9A shows the effect of impingement of jets against hydroxyapatite discs coated with biofilm.

The group of six images in FIG. 9A shows two replications of an impingement experiment. The control, which was not cleaned, shows a significant blue (stain) color. The water-cleaned discs show a slight reduction in the amount of blue stain. The discs cleaned with a cellulose-containing composition show the most white, or the smallest amount of blue stain, indicating the best cleaning has occurred.

Figure 9B:
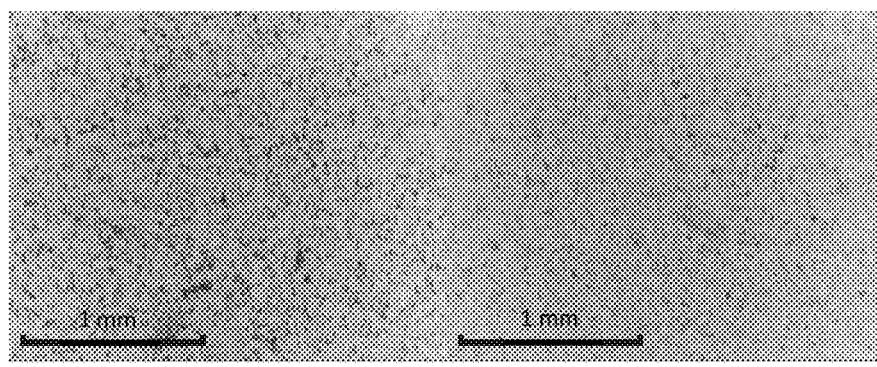
FIGS. 9B and 9C show a comparison of cleaned surfaces.
Figure 9C:
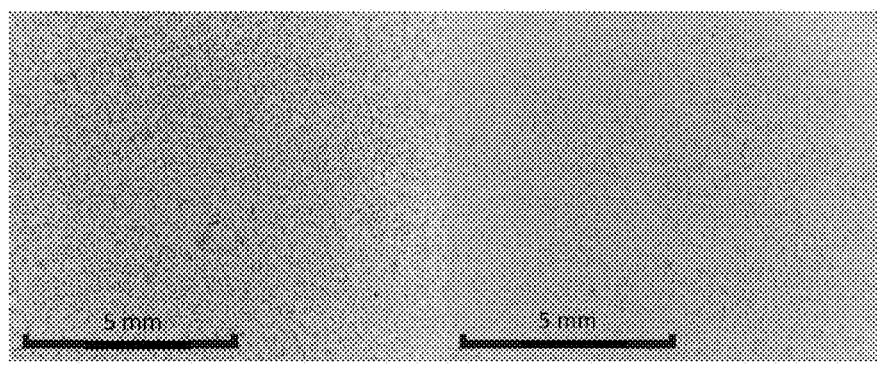

In a separate experiment conducted on hydroxyapatite discs using toothbrushes, S. mutans biofilm was cultivated on the surface of a synthetic hydroxyapatite (HA) discs for days. The biofilm was stained with methylene blue (0.3%) for 15 minutes and then rinsed with sterile water. The discs were brushed 30 times across its surface in cycles of 10 consecutive strokes increments with a manual toothbrush. Disc 1 was primarily cleaned with Colgate toothpaste at 50% dilution to simulate dilution by saliva during normal brushing. Disc 2 was cleaned with the inventive composition (EP3) also at 50% dilution as described above. Both discs were then restained with methylene blue. After cleaning, images were collected with a Firefly GT700 scientific microscope under LED light at 15× and 230× magnification with 2.0 Megapixel resolutions. Larger amounts of blue stain indicate poorer cleaning, and smaller amounts of blue indicate better cleaning. The results clearly show that the inventive composition achieves significantly better removal of S. mutans biofilm from HA surface compared to prior art toothpastes. The results of this example indicated that the inventive composition can remove the biofilm despite dilution to 50%. Based on measurements taken after each 10 strokes, it is clear that the inventive composition can provide better and faster removal of biofilm from HA, and can be effective even when persons do not brush their teeth for the recommended 120 seconds. The results are illustrated in FIGS. 9B and 9C.

In connection with jetted applications of the composition, an applicator with a slit or orifice geometry could be useful for propelling the composition into the interproximal space, and the locally high shear at the orifice/slit could cause the viscosity to drop enough for fluid to flow from the orifice into interproximal space. Flow and forces generated in interproximal space are believed to be sufficient to remove biofilm. Such a composition would be thinner than commercial toothpaste and its shear-thinning properties would help it to impinge. The shear thinning properties can be adjusted based on the concentration of ingredients as described elsewhere herein. A composition of an embodiment of the invention has been tested in a commercial AirFloss device and it works nicely. We found that Nano-Clean toothpaste cleaner can be delivered by the Phillips AirFloss and can remove biofilm from hydroxyapatite substrates as described elsewhere herein. It is helpful if the composition includes friction elements such as MicroCrystalline Cellulose, silica, calcium carbonate particles or the like. It is possible to select the particle size of the friction elements to be small enough to flow between teeth. For example, the MCC particles can be 25 microns to maximum of 100 microns overall dimension.

Example 6

Figure 10A:
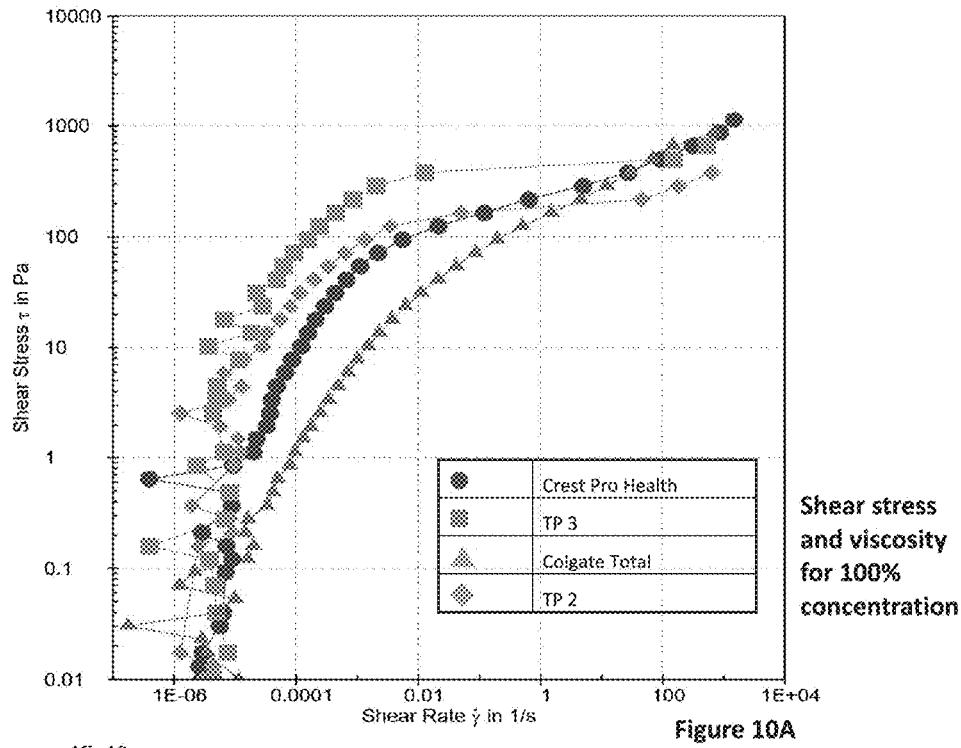
FIGS. 10A, 10B show shear stress and viscosity, respectively as a function of shear rate, at 100% concentration. These are shown for two embodiments of the invention and for two commercial toothpastes.
Figure 10B:
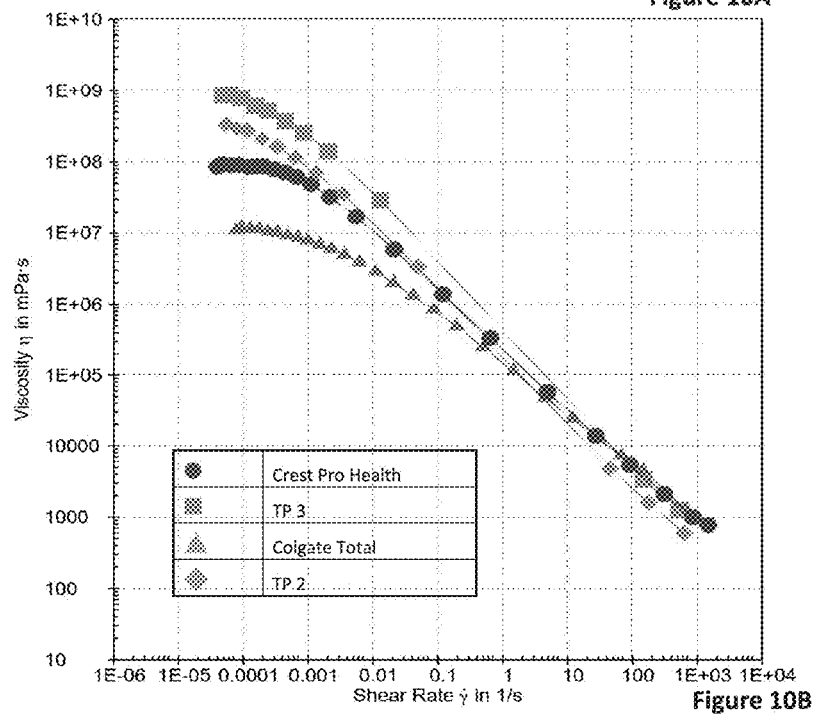
Figure 10C:
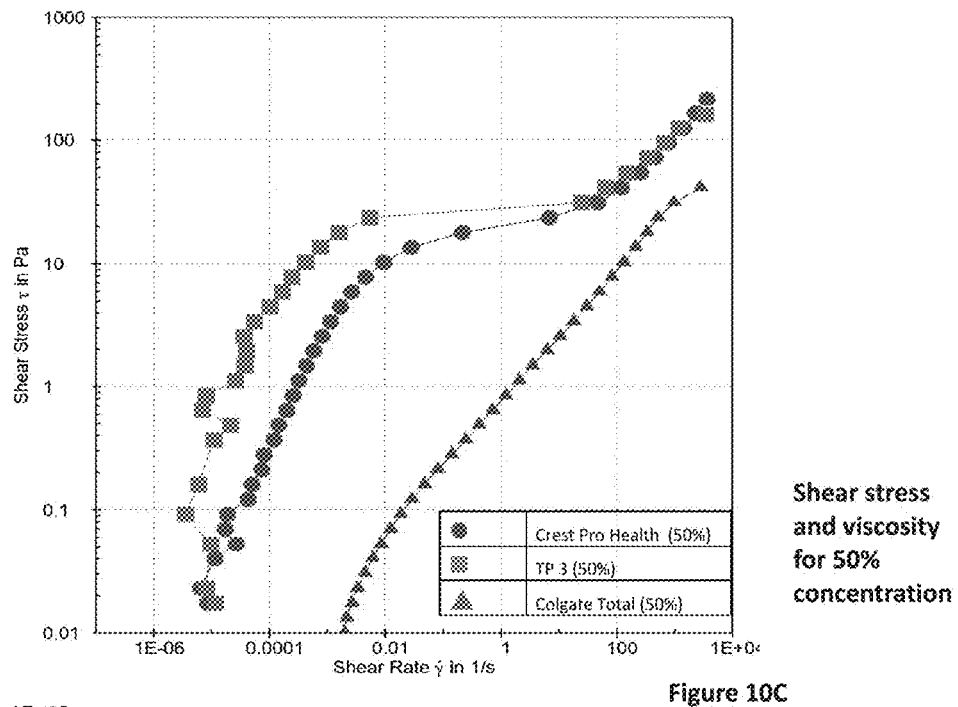
FIGS. 10C, 10D show shear stress and viscosity, respectively as a function of shear rate, at 50% concentration. These are shown for two embodiments of the invention and for two commercial toothpastes.
Figure 10D:
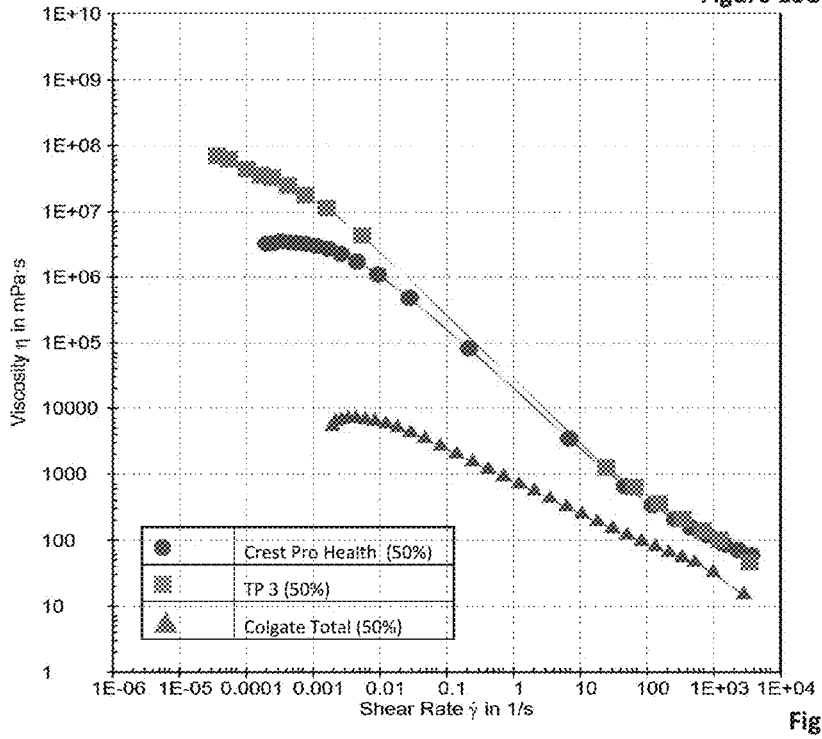
Figure 10E:
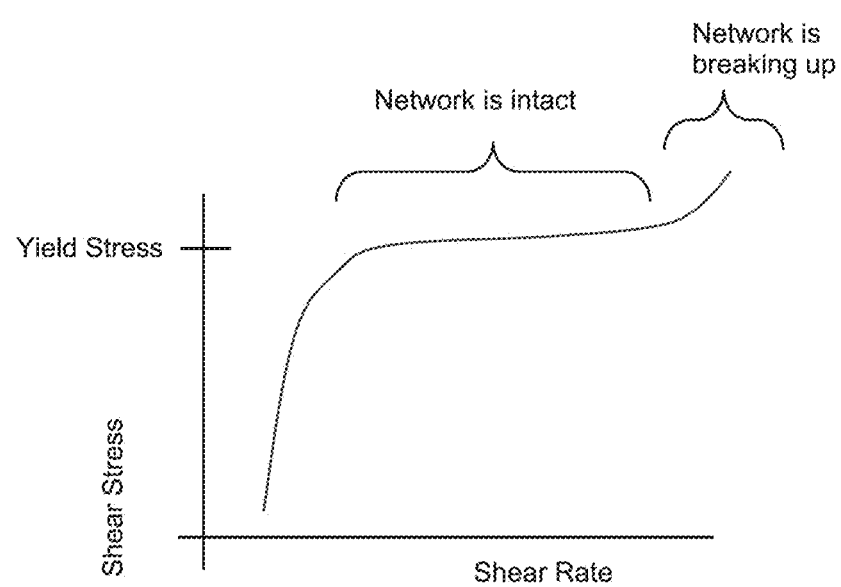
FIG. 10E is a schematic illustration of regimes of operation and flow of compositions of embodiments of the invention.

Reference is now made to FIGS. 10A and 10B (at 100% concentration), and to FIGS. 10C and 10D (at 50% concentration). FIG. 10E shows a generic representation of FIGS. 10A and 10C. In this example, we performed viscosity and shear stress measurements as a function of the shear rate at a gap size of 1.2 mm using the Anton Paar Rheometer as described in Methods. We compared two inventive compositions toothpastes with two leading commercial toothpastes, namely: Crest® Pro-Health and Colgate® Total. The results clearly demonstrated that the inventive composition toothpaste has significantly higher yield stress values compared to the leading commercial toothpastes. Here, we refer to yield stress as the minimum stress by which the shear rate starts to be significantly different than zero, e.g. $10^{-4}$ $s^{-1}$. At these conditions, the inventive composition made with SAP has an apparent yield stress of about 100 Pa and the inventive composition made without SAP has an apparent yield stress of about 30 Pa. On the other hand, Crest® Pro-Health has an apparent yield stress of about 10 Pa and Colgate® Total has an apparent yield stress of about 1 Pa. Significantly, the inventive composition holds a relative high viscosity and yield stress even when diluted 50% with water. Colgate® Total has a significant loss of viscosity upon dilution which indicates the severe breakdown of the microstructure/network of the material. Crest® Pro-Health does not seem to have a microstructural network breakdown upon dilution at 50%, but always has lower yield stress and zero shear viscosity compared to the inventive composition. In particular, the apparent yield stress for the 50% dilution of the inventive composition is 5 Pa, compared to Crest® Pro-Health at 0.4 Pa and with Colgate® Total having lost any measurable yield stress.

The loss of mechanical properties and the breakdown of the network structure upon dilution makes a toothpaste unable to deliver any shear stress onto the surface of the tooth, thereby inhibiting any possible plaque removal. On the contrary, the inventive composition still has significant mechanical properties that can allow for a robust plaque removal even upon dilution.

We should specially note that there is another characteristic fingerprint of the microfibrillated cellulose fibers used in the inventive compositions, which is the manifestation of a constant or nearly constant shear stress (between 150-400 Pa) within a shear rate range of 1 to >100 s which is a range that is normally experienced during tooth brushing. This suggests that the microstructure of the inventive composition remains intact within this shear rate range. In contrast, the shear stress of the two leading commercial toothpastes continuously change suggesting that there might be a microstructural network progressive breakdown. The latter suggests that the two leading toothpastes will not be able to remove plaque from teeth at the shear rates and velocities experienced during tooth brushing. This result has been verified by our biofilm removal experiments from tubes as detailed in Examples herein. The graphs show Shear stress as a function of the shear rate for NanoClean ToothPaste (NCTP) with SAP (grey squares), NanoClean ToothPaste (NCTP) without SAP (orange squares), Crest Pro Health (red circles), Colgate Total (green triangles). TP2 is a composition without SAP, while TP3 is a composition with SAP.

Example 7

Figure 11A:
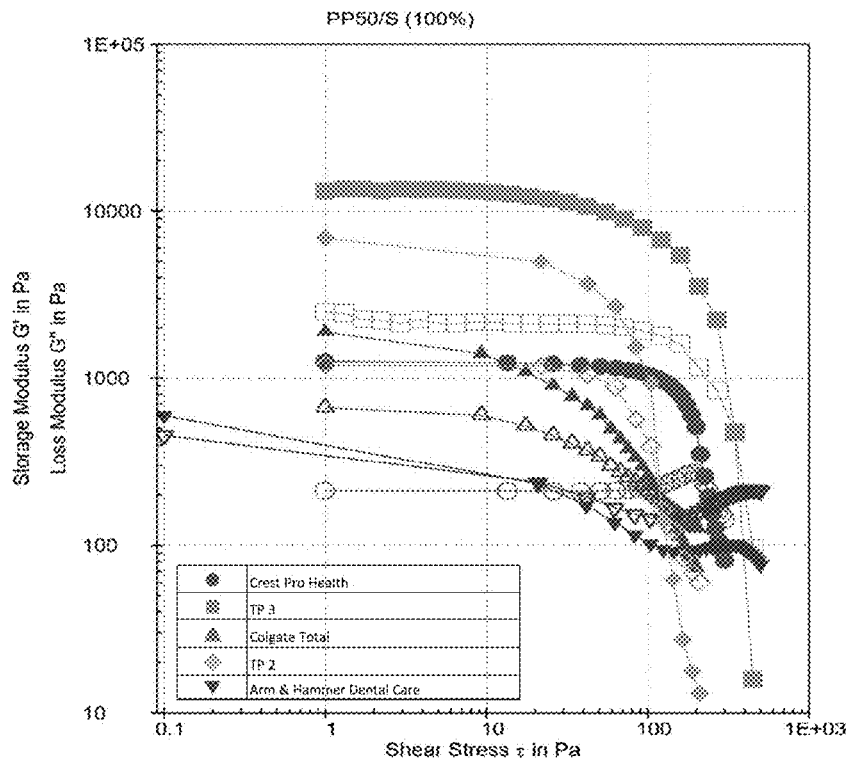
FIG. 11A shows, at 100% concentration, elastic modulus G' and loss modulus G", for three commercial toothpastes and two compositions of an embodiment of the invention.

This Example presents viscoelastic properties of the inventive composition compared to prior art toothpastes, and showing the effect of dilution. Reference is now made to FIG. 11A (which is at 100% concentration) and 11B (which is at 50% concentration). In this example, we performed oscillatory shear stress measurements of the inventive composition and prior art toothpastes at a fixed angular frequency of 10 rad/s using the Anton Paar MCR 302 Rheometer as described in Methods. The inventive composition toothpaste (made with or without SAP) has higher elastic modulus (G') than the prior art commercial toothpaste in the linear viscoelastic regime, i.e. the regime where for a given angular frequency the elastic and viscous moduli are independent from the oscillatory shear stress applied. For all undiluted toothpastes, at low oscillatory shear stresses, the G'>>G", thereby highlighting the typical response of a gel-like material and the possible presence of a network. Two significant stresses can be identified from the data generated: i) the value of oscillatory shear stress by which the elastic modulus starts to significantly decrease (which is similar to the apparent yield stress as inferred from the continuous shear flow test of shear stresses vs shear rate plot) and ii) the oscillatory shear stress by which G" starts to be larger than G' that likely represents the breakup of the microstructural network. In this case, it is clear that the inventive composition toothpaste with SAP can withstand larger stresses than the commercial toothpastes. In addition, the Arm & Hammer® Dental Care toothpaste seems to break down at very low oscillatory stress.

Figure 11B:
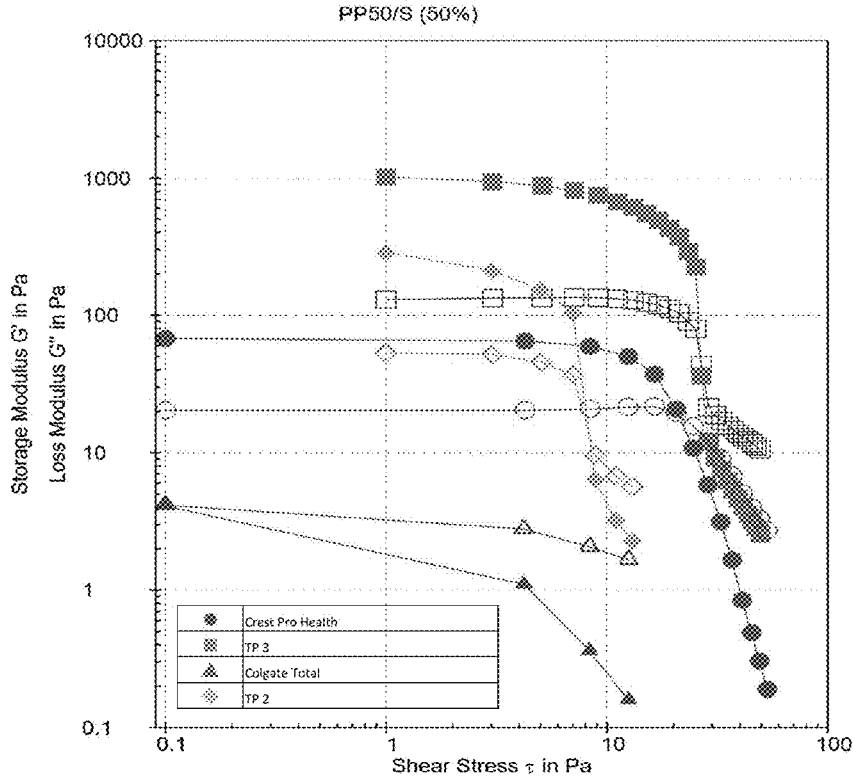
FIG. 11B shows, at 50% concentration, elastic modulus G' and loss modulus G", for three commercial toothpastes and two compositions of an embodiment of the invention.
Figure 11C:
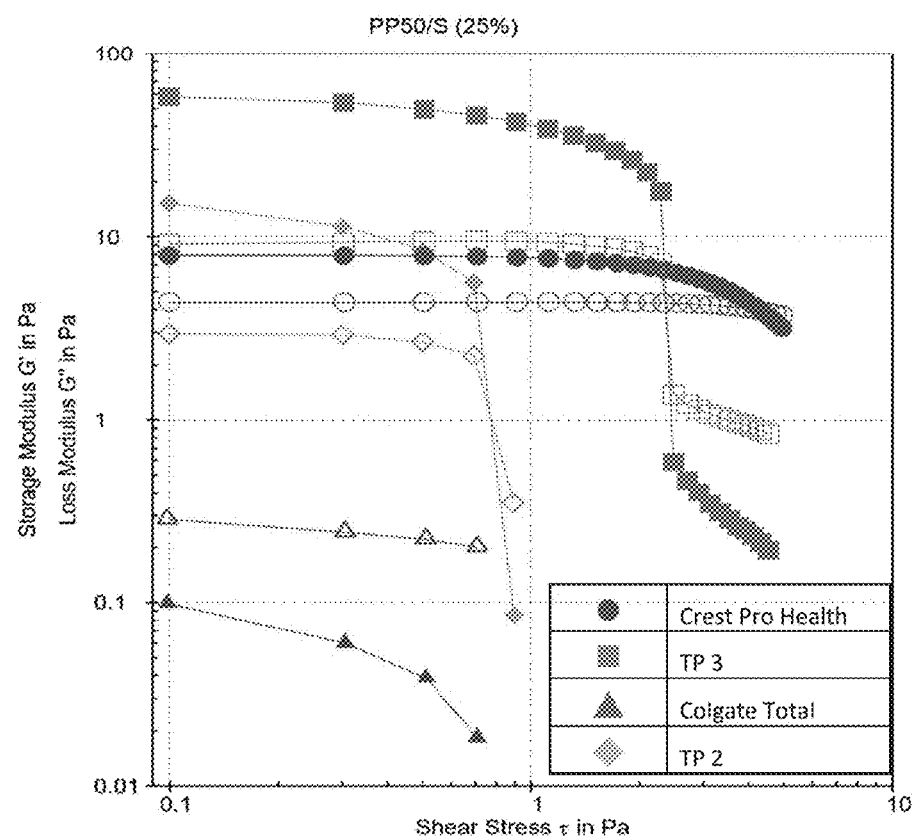
FIG. 11C shows, at 25% concentration, elastic modulus G' and loss modulus G", for three commercial toothpastes and two compositions of an embodiment of the invention.

We should specially note that one can associate the shear stress at which G" becomes higher than G' with the value of shear stress (shear stress vs. shear rate plot) corresponding to the network breakdown. This is important because plaque biofilm removal diminishes after the network breaks down which is associated with G" becoming larger than G'. It is important to indicate that in an oscillatory shear test, it is the amplitude of the strain rate $\dot{\gamma}_0$ that is equivalent to the shear rate in the continuous shear flow test (shear stress vs. shear rate plot) where the amplitude of the strain rate $\dot{\gamma}_0$ is equal to $\gamma_0 \cdot \omega$, where $\gamma_0$ is the strain and $\omega$ is the angular frequency. At 50% dilution, the inventive composition toothpaste still shows a larger G' in the linear viscoelastic regime and a cross-over point between G' and G" at larger stresses as compared to prior art toothpastes. At 25% dilution, the inventive composition still has the larger value of G' in the linear viscoelastic regime as compared to prior art toothpastes. Upon dilution, the Arm & Hammer® Dental Care toothpaste loses most of the elasticity (values not reported because they are smaller than the sensitivity of the instrument), likely suggesting the formation of a slurry and the disruption of any network of particles or polymers. For the inventive composition, having a larger G' (for a given stress) than the prior art toothpastes (for diluted and undiluted states), might help providing the toothpaste enough elasticity to remove plaque. However, just designing a toothpaste with a specific elastic modulus over a range of stresses and shear rates does not guarantee whether there is plaque removal or not, but rather the combination of G', the friction factor and other microstructural parameters (such as the morphology and the length scale of the constitutive element of the material) have to be taken into account to effectively deliver stresses onto the surface of the tooth and remove plaque. Numerical data from FIGS. 11A, 11B are presented in the Table 5.

TABLE 5

| PP50/S 100% | Cross-Over | G' Yielding |
|---|---|---|
| TP2 | 123 | 63 |
| TP3 | 346 | 121 |
| Crest PH | 224 | 100 |
| Colgate Tot | 125 | 17.5 |
| A&H CC | 20.8 | 20.8 |

TABLE 5-continued

| PP50/S 100% | Cross-Over | G' Yielding |
|---|---|---|
| 50% | | |
| TP2 | 8.82 | 7 |
| TP3 | 26.7 | 13.1 |
| Crest PH | 20.5 | 16.4 |
| Colgate Tot | 0.09 | 0.09 |
| A&H CC | na | na |
| 25% | | |
| TP2 | 1 | 0.5 |
| TP3 | 2.29 | 2.1 |
| Crest PH | 4.1 | 2.5 |
| Colgate Tot | na | na |
| A&H CC | na | na |

Example 8

We performed some experiments mimicking the flow of the toothpaste in the interproximal tooth space to infer the typical flow rates and velocities of the paste when flowing through such an orifice. We practiced a hole along the thickness direction of an ABS block having an area of 150 mm×40 mm and a 11 mm thickness. The hole diameter was about 1.6 mm. We then vertically positioned and aligned the block and on one side of it we distributed 10 ml of toothpaste and brushed it with a commercial manual toothbrush applying a force of about 5N, with a velocity ranging from 1 to 10 cm/s and brushing back and forth the paste over the hole. Specifically, this is like having a flow over a plane here there is a hole of 1.6 mm entering a tube 11 mm long. On the other side of the hole we collected the exiting paste and measured its weight over time. We used commercial toothpaste and the NCTP toothpaste, both diluted and not. This process was done in triplicate to measure the mass flow rate, from which velocity is calculated. The values of the flow rate and average velocity through the hole are reported in Table 6.

TABLE 6

| Channel diameter [mm] | 1.588 | 1.588 | 1.588 |
|---|---|---|---|
| Cleaning formula | Toothpaste 3 | ½ Toothpaste 3 | ¼ Toothpaste 3 |
| | 0.065 | 0.015 | 0.151 |
| | 0.032 | 0.051 | 0.097 |
| | 0.027 | 0.039 | 0.177 |
| avg mass flow rate [g/min] | 0.041 | 0.035 | 0.142 |
| density [g/cm^3] | 1.000 | 1.000 | 1.000 |
| area [cm^2] | 0.079 | 0.079 | 0.079 |
| v [cm/min] | 0.522 | 0.442 | 1.789 |

Example 9

Figure 12:
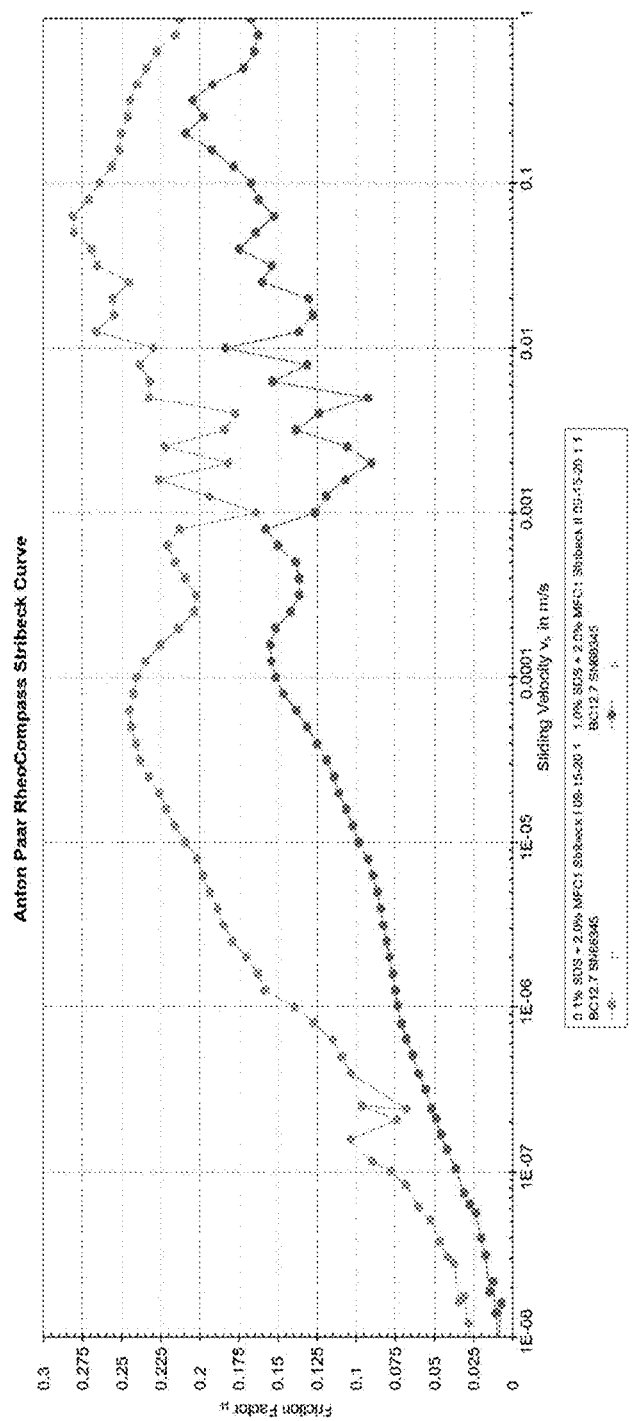
FIG. 12 is a Stribeck curve showing friction factor as a function of sliding velocity, for a low-surfactant-concentration fibrillated composition and for a high-surfactant-concentration fibrillated composition.

Reference is now made to FIG. 12, which is a Stribeck curve illustrating friction factor measurements as a function of sliding velocity. The composition tested here is neither a commercial toothpaste nor a full composition of an embodiment of the invention, but rather a simple representative composition in order to show a basic tribological result. The composition simply contains microfibrillated cellulose and water and z surfactant, with the concentration of the surfactant being variable. The pins were PDMS. One curve is presented for a relatively small concentration of surfactant, and the other curve is presented for a larger concentration of surfactant. It can be seen that the friction factor decreases as a function of surfactant concentration.

Example 10A

Figure 13A:
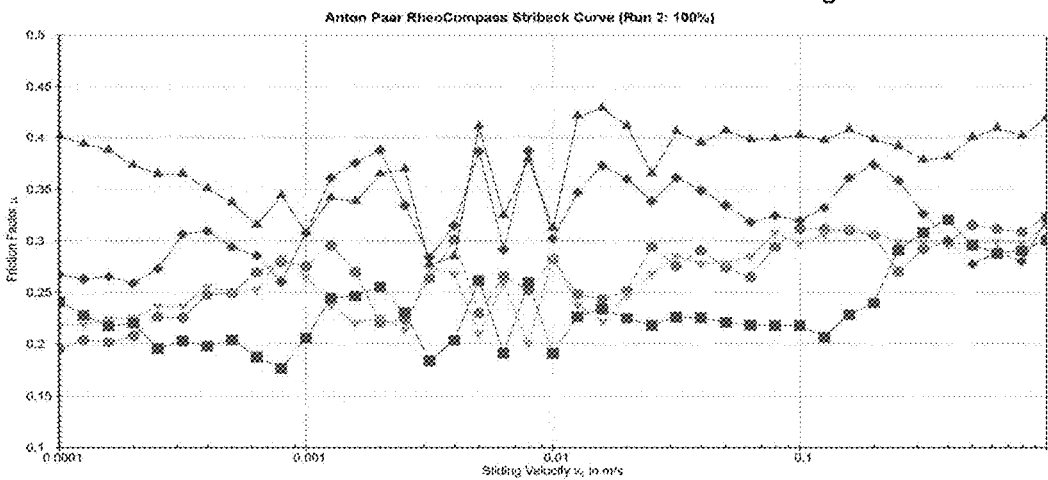
FIGS. 13A 13B and 13C are Stribeck curves showing friction factor as a function of sliding velocity, for three commercial toothpastes and two inventive compositions, for 100 concentration and 50% concentration and 25% concentration, for a glass ball against pins made of Teflon.
Figure 13B:
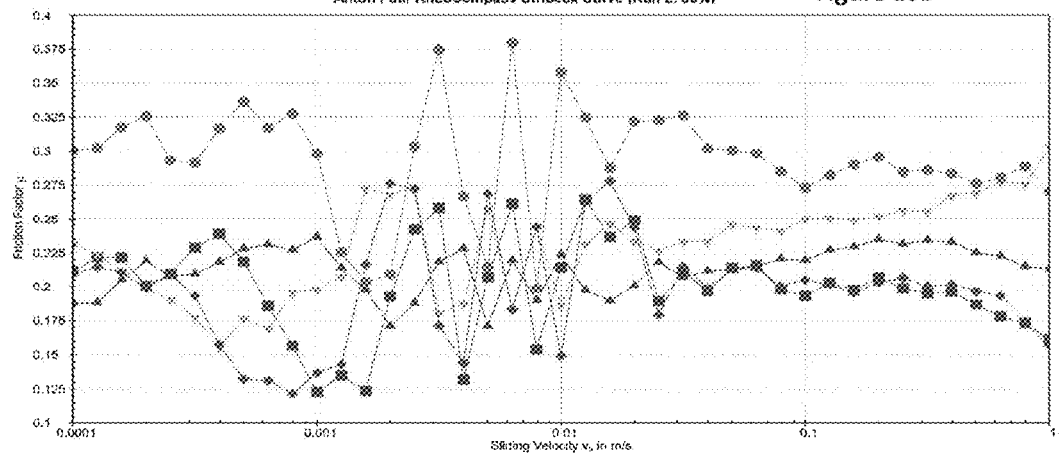
Figure 13C:
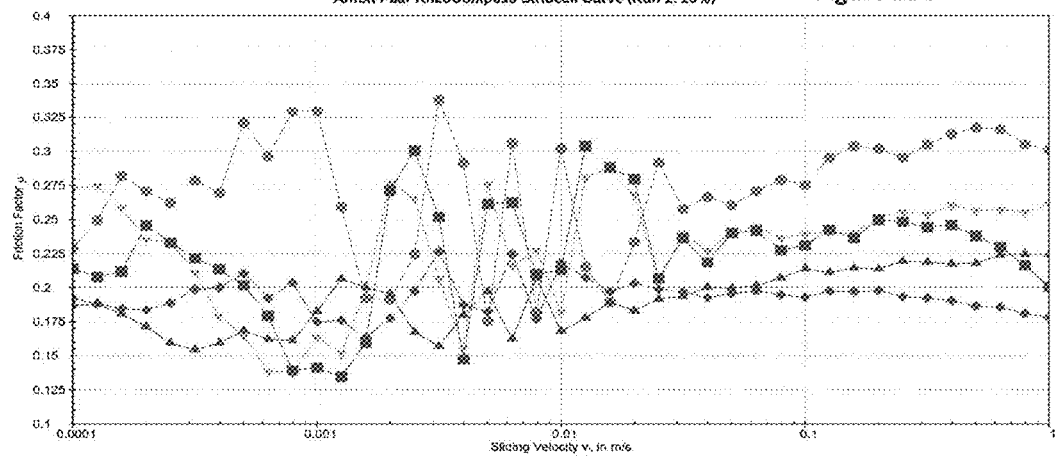
Figure 14A:
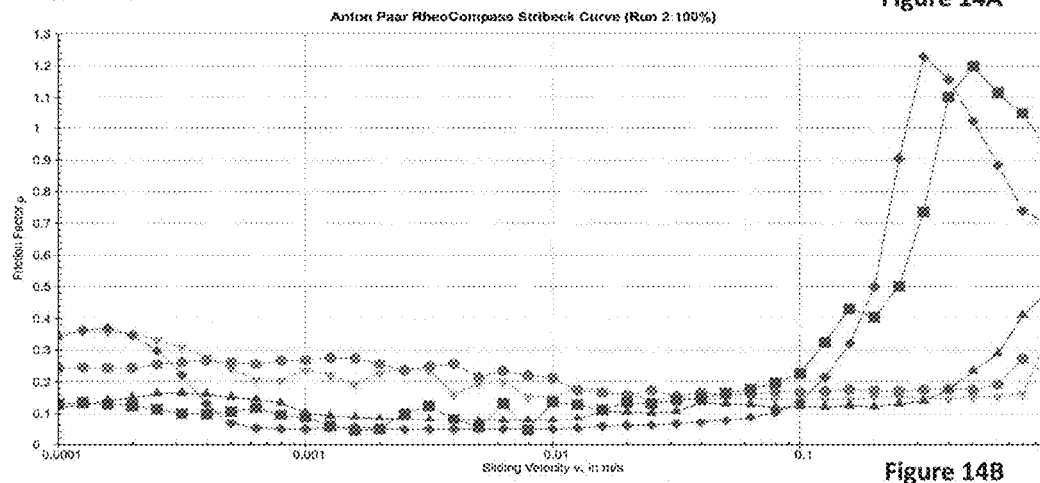
FIGS. 14A 14B and 14C are Stribeck curves showing friction factor as a function of sliding velocity, for three commercial toothpastes and two inventive compositions, for 100 concentration and 50% concentration and 25% concentration, for a glass ball against pins made of PDMS (polydimethylsiloxane).
Figure 14B:
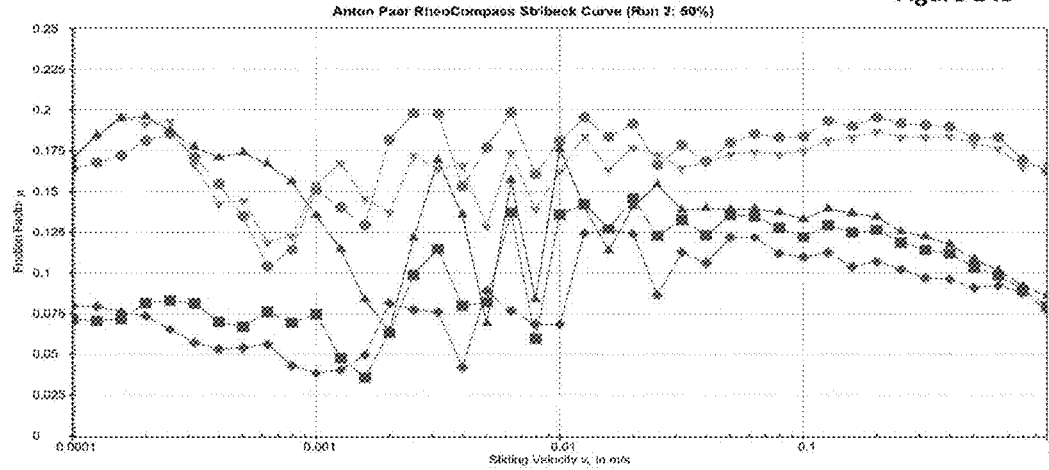
Figure 14C:
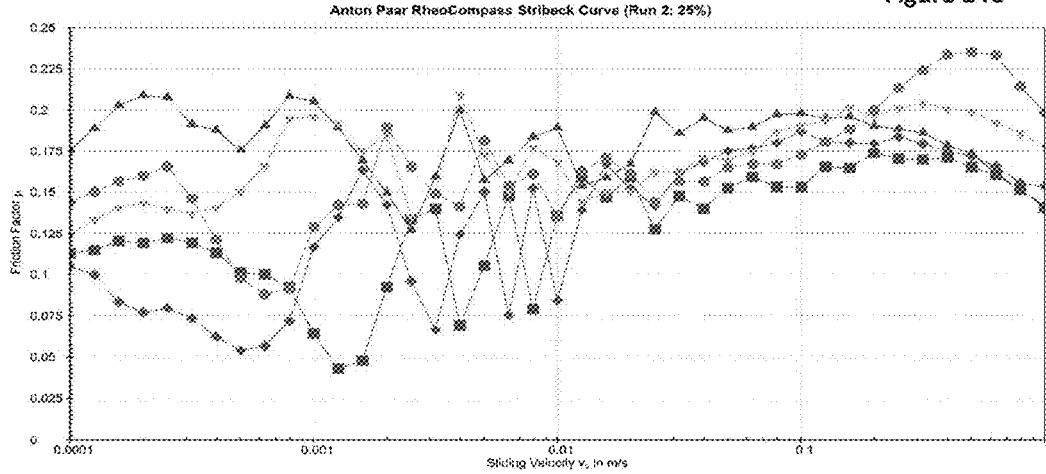

In this example, we performed friction factor measurements as a function of sliding velocity (Stribeck curves) on Teflon pins using the tribology attachment of the Anton Parr Rheometer. As in the previous Example, we consider sliding velocities larger than 1 cm/s to simulate velocities experienced during tooth brushing. In this regime, the toothpaste tested appears to be in the so-called mixed or transition regime of friction. In the undiluted state, Colgate® Total had the lowest friction factor values, whereas Arm & Hammer had the highest friction factor values followed by the inventive composition (NCTP) and then Crest® Pro-Health as shown in FIG. 13A. Strikingly, we discovered that there is a complete change in the friction properties when these toothpastes are diluted, with the NCTP (with and without SAP) holding a larger value of friction factor than the commercial toothpastes when diluted to a concentration of 50% (FIG. 13B) and even when diluted to 25% of original concentration (FIG. 13C). These results support that the inventive composition has a powerful capability of providing frictional forces over the surface and achieving effective cleaning as described elsewhere herein. We should also note that the inventive composition performs the cleaning function without scratching the surface since our material is made of a network of soft fibers.

Example 10B

This is similar to Example 10A except that instead of being made of Teflon, the pins were made of PDMS (polydimethylsiloxane). We performed friction factor measurements as a function of sliding velocity (Stribeck curves) on PDMS (polydimethylsiloxane) pins using the tribology attachment (ball on pins) of the Anton Paar MCR 302 Rheometer. PDMS is more deformable as compared to Teflon and this may better reflect the situation of toothbristle interaction during tooth brushing. It is well known in tribology that the chemistry and mechanical properties of the ball and pin surfaces affect friction measurements. In this Example, the deformable PDMS pins can better mimic toothpaste behavior between a hard surface (like the tooth enamel) and a softer material (like the bristles of the toothbrush). We specifically consider sliding velocities larger than 1 cm/s because such velocities can simulate the useful range of velocities encountered during tooth brushing.

In this velocity range, the commercial toothpastes tested (namely Arm & Hammer Dental care, Crest Pro Health, Colgate Total) appear to have low friction factor values in the so-called mixed (transition) regime of friction until reaching a velocity of 10 cm/s. At velocities larger than 10 cm/s, the commercial toothpastes transition into the hydrodynamic regime of friction (the friction factor has a sudden increase as known in the art), suggesting that they have experienced significant break-up of their microstructure and consequently they transform into slurries. As described elsewhere herein, slurries are unlikely to deliver enough shear stresses or frictional forces sufficient to remove the plaque from teeth. It is also important to note that once the toothpaste transforms into a slurry, a depletion layer will form resulting in diminished removal of biofilm plaque as described elsewhere herein. In contrast, the inventive composition remains intact with higher friction factor up to a velocity of 100 cm/s without transitioning into the hydrodynamic regime. This indicates that the inventive composition should remain effective even at higher displacement velocities of at least 100 cm/s or higher.

The inventive compositions (with and without SAP), holds a larger value of friction factor than the commercial toothpastes even when diluted with water at 25% of its initial concentration. In the cases of diluted toothpastes samples, none of the inventive composition samples have shown a sudden increase in friction factor at the higher velocity ranges, i.e. there was no evidence of manifestation of hydrodynamic regime of friction. The fact that the inventive compositions deliver higher friction factor on a surface as compared to the commercial toothpastes, even when diluted, supports the discovery that the inventive compositions have a powerful capability to remove biofilm plaque even under high velocities and dilution ratios such as those experienced during tooth brushing. We should specially note that this process happens without scratching of the surface since our material is made of a network of soft fibers. Numerical data from FIGS. 13A-13C is further presented in Table 7.

TABLE 7

| PDMS | Sliding Velocity | | | | | |
|---|---|---|---|---|---|---|
| | 0.01 cm/s | | 0.1 cm/s | | 1 cm/s | |
| | Run 1 | Run2 | Run 1 | Run2 | Run 1 | Run2 |
| 100% | | | | | | |
| TP2 | 0.582 | 0.351 | 0.345 | 0.238 | 0.241 | 0.153 |
| TP3 | 0.385 | 0.243 | 0.365 | 0.268 | 0.265 | 0.212 |
| Crest PH | 0.112 | 0.341 | 0.072 | 0.048 | 0.051 | 0.049 |
| Colgate Tot | 0.241 | 0.241 | 0.249 | 0.206 | 0.179 | 0.191 |
| A&H CC | 0.270 | 0.120 | 0.167 | 0.103 | 0.141 | 0.078 |
| 50% | | | | | | |
| TP2 | 0.466 | 0.172 | 0.288 | 0.155 | 0.165 | 0.163 |
| TP3 | 0.358 | 0.164 | 0.243 | 0.151 | 0.172 | 0.183 |
| Crest PH | 0.080 | 0.048 | 0.038 | 0.032 | 0.068 | 0.042 |
| Colgate Tot | 0.136 | 0.072 | 0.142 | 0.075 | 0.179 | 0.136 |
| A&H CC | 0.258 | 0.170 | 0.084 | 0.136 | 0.136 | 0.176 |
| 25% | | | | | | |
| TP2 | 0.438 | 0.125 | 0.391 | 0.129 | 0.226 | 0.136 |
| TP3 | 0.396 | 0.144 | 0.288 | 0.196 | 0.179 | 0.168 |
| Crest PH | 0.074 | 0.105 | 0.115 | 0.117 | 0.159 | 0.084 |
| Colgate Tot | 0.083 | 0.113 | 0.107 | 0.064 | 0.112 | 0.136 |
| A&H CC | 0.266 | 0.175 | 0.152 | 0.205 | 0.129 | 0.189 |

Further Remarks

Formulations and embodiments have been disclosed herein and in incorporated-by-reference documents, which have proven effective for removing biofilm and plaque using the stated formulation. The formulations disclosed in some of the past documents had a viscosity that was suitable to be pumped through long narrow tubes (such as channels in endoscopes) without requiring excessive pressure drop per unit length. These can be referred to as an initial formulation. These formulations have also been tested at various dilutions such as 50% dilution with respect to the initial formulation, and it has been found that when so diluted they still are effective at removing biofilm and plaque.

It is furthermore possible to make an initial formulation that is slightly more concentrated than what was disclosed. Such a formulation would have a somewhat larger initial viscosity than the already-disclosed formulation. For example, if a syrup-like formulation for use in endoscope channels has a viscosity of about 10,000 mPa-s at a certain shear rate, a more toothpaste-like formulation for toothbrushing might have a viscosity of 50,000 mPa-s at that same shear rate. For example, it would be possible to proportionally increase the concentration of Minute Fibrils, and the concentration of friction elements such as MCC, and the concentration of SAP. In particular, the concentration of Minute Fibrils could increase because the Minute Fibrils help to create the network and entanglement. The concentration of other ingredients might not need to change.

For a toothpaste application, the initial viscosity can be fairly large because there is no actual requirement for flowability through a long narrow channel; it is merely necessary for toothpaste to be dispensed through one moderate-diameter orifice onto a toothbrush. Eventually, at some dilution, the composition would start to lose cleaning effectiveness and would reach a point of ineffectiveness, but starting at an even more concentrated initial formulation would provide more space or opportunity for dilution before that point of ineffectiveness is reached.

By starting with a somewhat high initial concentration and viscosity, it is likely that an even wider range of dilution might be accommodated while still providing good cleaning performance throughout the whole range between initial formulation and diluted formulation.

Embodiments of the invention may contain an anti-sensitivity ingredient; a whitening ingredient; a tartar control ingredient; a stain removal ingredient; an anti-odor ingredient; HOCl; ClO2; NaClO2; NaClO3; chlorhexidine or chlorhexidine gluconate; CTAB (cetrimonium bromide) or equivalent; PHMB (polyhexamethylene biguanide); LAE; antibiotics; triclosan; biofilm-growth suppressing agents; xylitol; usnic acid; thrush-suppressing agents; SnF2 system; and the like. Embodiments of the invention may include propolis, which can function as an anti-inflammatory or antimicrobial or plaque inhibiting agent.

In embodiments of the invention, there may be some form of network or network flocs of dispersed ingredients and friction elements that create mechanical action at the surface of teeth to remove plaque or stains, InterProximal space, gum line, tissue, surface of tongue or anywhere in the oral cavity as desired. The network or flocs can exist both at full concentration of the composition and upon some amount of dilution. Embodiments of the invention that are relatively fluid may forms flocs, and such flocs can remove plaque and stains by mechanical force such as flow by action of swishing with mouth or by applicators which can deliver the composition as a single phase fluid or mixed with air, or as two-phase flow, or which can be continuous or intermittent either programed or automated or actuated manually.

Compositions of embodiments of the invention can be packaged or delivered as a striped composition. Each stripe can perform different functions together in the mouth. One or more compositions can be delivered to the mouth to ensure stability when stored within the tube. Examples include: a) chemical reaction such as generating fluoride; b) whitening agents such as those which include peroxide; c) delivering an agent which sanitizes mouth such as; NaOCl; ClO$_2$; O$_3$ (ozone); peroxides; peroxy acids; or other odor removing agents or neutralizers; d) anti-sensitivity agents; e) tongue cleaning or disinfection said as to treat thrush or fungal/yeast infections; h) antibiotic or antimicrobials; g) any agent or compound to promote oral or total health or prevent disease including Alzheimer's disease, dementia, heart disease, etc.

One skilled in the art may attempt to use polymers or make other forms of networks and determine the rheology, tribology and may prevent the formation of the depletion/lubrication layer, would be using the teaching of the present invention. This includes: resistance to dilution, over formulating so that this would produce the results of the invention in terms of cleaning or treating teeth; would be employing part or whole of the invention would be infringing the substance or teaching of the invention. The invention is not intended to be limited to or limited by using the fibrillated network but includes methods, rheology of soft materials and complex fluids, tribology or friction including controlling macroscopic parameters such as friction factors or friction coefficients, microscopic friction microscopic or tribology at the surface of teeth or within the InterProximal space, gum line, or on the surface of tissue. Embodiments of the invention can include any agent that satisfies dilution resistance or provides friction elements whether including fibers or fibrillated material. Embodiments of the invention can include a polymer carrier that can provide persistent effects such as antimicrobial, odor control, acid control. As an example, it can include Gantrez polymers to provide substantive action of triclosan. This can include compositions, methods, apparatus and delivery systems.

Embodiments of the invention include any composition whether based on polymers or polymer molecules or networks or combination of networks or including physical or chemical cross-links or including friction elements that can deliver the rheology, tribology and friction to remove plaque, stains, or treat the oral cavity or use the methods of preventing the effect of saliva induced including dilution or other forms of dilution. Embodiments of the invention are not intended to be limited to the materials used to make a network or networks to combine them with friction elements. Embodiments of the invention are not limited to friction elements provided in the invention since there are many substitute ingredients which can be used or selected or optimized are possible by persons skilled in the art.

For achieving cleaning using embodiments of the invention, it is helpful if integrity of the network is maintained (illustrated schematically in FIG. 10E) such that an effective level of shear stress can be generated or created during the application which falls within the useful range of application velocity such as brush velocity or effective range of the shear rate effective velocity of brush can be from 1 to 40 cm/sec or more depending on the type of the brush, and the shear rate can be from 1 to 500/sec or 1 to 1000/sec. Embodiments of the invention could be used to clean other objects in a dental office including dental unit water line vacuum line dental tools implants and the like. For the purpose of tooth whitening, peroxide compounds that act as whitening agents can be added into the composition to achieve whitening of teeth.

Delivery forms and modes of application of embodiments of the invention can include: solids; chewable forms; chewing gum; pastes; gels; semi-solids; slurries; liquids; mouth wash; mouth rinse; sprays; pressurized canisters; loadable packaging for use in toothbrushes or in automated flossing; loadable in Airfloss or in Waterpik devices; delivered manually or with a pump; delivered pneumatically with a pump or piston; spread or coating, swishable formulations in the mouth; gargle fluids; salves; delivered via a nozzle; applied as tape; loaded into mouth guards or retainers; use din ultrasonic baths for dentures or tool cleaning delivered by a needle as for cleaning root canal or in tooth preparation before filling or repair; chewable and spitable dosage form for cleaning teeth; coated in floss; coasted in brush bristles; applied to teeth via conforming mold with or without flow or motion; used with ultrasonic scaler in the dental office; used to provide deep cleaning; delivered with or without a bristle brush; combined or delivered by any form of brush whether manual or automated; or other forms by persons skilled in the art. Embodiments of the invention may have sufficiently small viscosity to be delivered as a mouth rinse, or can be delivered by Waterpik; OralB fusion toothbrush; Air Floss and applicators that can direct and clean Inter-Proximal space. Embodiments of the invention may include travel kits and apparatus for use in sports and hiking and camping; application without brush such as in travel; fluoride delivery system with manual application such as by hand. An embodiment of the invention can include a finger sleeve applicator with or without filaments.

Embodiments of the invention may include cleaning tissue, bones, cartilages, etc., such as during surgery, such as orthopedic, oral or general surgery. Cleaning surfaces other than natural teeth is also contemplated including implants, braces, filings, artificial teeth, dentures, veneers. Cleaning is not limited to be performed inside the mouth but also can be made ex-situ such as cleaning in the dental office, laboratory, clinic or other settings. Embodiments of the invention can be used for treating sores or infected lesions in the mouth including tongue. Embodiments of the invention can be used for cleaning the gums and gum line to prevent gum disease.

Specifications of the Inventive Composition Including Rheological, Tribological and Microstructural Requirements:

The shear stress during application may be maintained in the useful shear rate range of tooth brushing which may be from 1-100 sec$^{-1}$ or higher such as from 1-500 sec$^{-1}$ or even higher than 500 sec$^{-1}$. A desirable shear stress >10 Pa may be provided, preferably >20-30 Pa, and even more preferably >50 Pa during tooth cleaning to provide effective plaque removal.

For the composition to be functional in removing plaque from teeth: G' should be higher than G" and G' should be higher than a critical value of G' ($G_c'$); $G_c'$ should be >1000 Pa and more preferably >1500 Pa and even more preferably >2000 Pa. These conditions should be satisfied even with saliva induced dilution which can decrease the concentration to 50% of its original value.

The friction factor as measured by the tribometer (Anton-Paar) may desirably be >0.15 and preferably >0.25 and even more preferably >0.3 even when diluted to 50% concentration of its original value. The friction factor measured by the tribometer may be considered a composite of friction coefficient at the interface of the solid materials as influenced or controlled by the cleaning composition itself. It is believed that friction factor measured by the tribometer may provide guidance to plaque removal with the composition but by itself is not a perfect predictor for biofilm removal. According to the present invention, additional friction properties may need to be satisfied such as the condition for actual removal of biofilm at the velocities and shear rates typically experienced during tooth brushing.

An evaluation method for evaluating micro-friction to determine the effectiveness of the composition has been performed in this invention by measuring the removal of *S. mutans* biofilm from a Teflon or other polymer tube, or from a hydroxyapatite tube having diameter of 1.37 mm, length 30 cm and flow under pressure drop of 10 psi. The composition may be considered plaque removal effective when >50% of the *S. mutans* biofilm is removed from the tube as measured by culture methods, microscopy or by evaluating the area covered with residual biofilm stained with Rose Bengal or methylene blue dye.

An effective composition for removing biofilm and plaque may include friction elements having sizes from 10 to 200 μm at a concentration between 0.2 to 5% and preferably between 0.5 to 2% by weight of the composition.

For the friction element to be effective, they may preferably be entangled or embedded in the matrix of the toothpaste so that they do not move away from the surface during simulated tooth brushing for <2 minutes. Conditions to satisfy this requirement may include: G' is >1000 Pa and yield stress >10 Pa wherein the G' remains above G" during the application to remove plaque. The upward movement perpendicular to the surface of the friction element may be <10 μm or more preferably <2 μm when the composition is applied to a surface for 2 minutes under normal force of 2-4 N at a velocity of 1-10 cm/s. The above condition should also satisfy at velocities higher than 10 cm/s to simulate other forms of application including mechanical or sonic brushing which are faster.

The effective composition may comprise a 3-D network of fibrillated materials and large length-scale structure from 2 μm to 250 μm and may include mechanical entanglements that resist dilution during tooth brushing such that G' remains higher than G" and G' is more than a G' value of >1000 Pa and yield stress >10 Pa. The effective composition may include friction elements which may create friction factor as measured by the tribometer of >0.15 and preferably >0.25 and is able to remove *S. mutans* biofilm as determined by the micro-friction method in the tube geometry.

As an alternative to the fibrillated material, an effective composition according to the present invention can be made from polymeric thickeners such as carrageenan or carrageenan-xanthan gum mixture thickened with nanoparticle silica such that G' is >1000 Pa, friction factor >0.2, yield stress as measured by the cross-over point of G' and G" versus shear stress curve remains effective to provide effective shear stress >10 Pa in the shear rate range from 0.1-100 Pa or preferably from 0.1-500 Pa. An effective composition of this type may include imbedded friction elements wherein the vertical movement of the imbedded friction element particles perpendicular to the surface is <10 μm after 2 minute application under normal force from 1-5 N or preferably <2 μm in less than 2 minutes application under conditions simulating tooth brushing. Persons skilled in the art may devise other compositions to satisfy the above requirements and be able to satisfy the micro-friction test by removing *S. mutans* biofilm in the tube geometry under the condition specified above. The present compositions and methods of the invention are not intended to be limited to fibrillated material but any other matrix which can satisfy the above recited requirements would be considered an element of the invention. It is possible that instead of or in addition to the fibrillated or polysaccharide material, the composition can include chitosan.

Method and Composition for Removing Plaque Biofilm from Teeth by Employing Formulation not Based on Fibrillated Materials and which Withstands Dilution During Teeth Cleaning.

In an embodiment of the invention, an orally acceptable composition based on polymeric thickeners or a mixture of polymer thickeners and crosslinking particles or agents can be made to satisfy the rheological and tribological requirements of the present invention such as to withstand dilution by water or saliva to 50% or 25% of undiluted preparation and remove plaque from teeth by creating sufficient shear stresses and friction forces sufficient to overcome the biofilm plaque deposited on teeth or in between teeth. This can be accomplished without the use of fibrillated material.

In an embodiment, the polymer thickener may include but not limited a. Carrageenan mixtures irrespective of the form of carrageenan at sufficient concentration to form a network with or without thickening silica.

b. Mixture of carrageenan in any form and xanthan gum in optimized ratios to retard dilution up to 50% or 25% of undiluted preparation.

c. Mixture of carrageenan in any form and sufficient thickening silica to form network structures that retard dilution up to 50% or 25% of undiluted preparation when used to clean teeth with any form of brushes including manual, mechanic or ultrasonic.

d. Mixture of carrageenan in any form or carboxymethyl cellulose with or without xanthan gum or other polymers to forma network structure that retards dilution at 50% or 25% of undiluted preparation; this mixture may or may not include thickening silica at optimal concentration to provide the requisite rheological and tribological parameters as provided in the invention.

e. Mixture of carbopols and cellulosic thickeners with thickening silica.

f. Any other acceptable polymeric thickeners or their mixtures that when mixed with thickening silica, c neb optimized to provide a composition that can retard dilution at 50% or 25% of undiluted preparation and still removes biofilm when applied to clean teeth.

The concentration of polymeric mixtures can be increased up to 5 or 10% and the concentration of thickening silica (or other thickening agents) can be increased to 5 or up to 20% or higher to provide the required rheological, tribological properties and resistance to dilution to remove plaque form teeth as detailed in the present invention.

The particle size, surface chemistry, and concentration of the thickening silica are critical to produce the dilution retarding composition as in the present invention Rheology modifier may be added at optimal concentration to make the composition flow from tube and be applied to clean teeth at acceptable levels to customers as is known in the art.

The values of the rheological and tribological parameter of any composition made without fibrillated materials may fall within or outside the ranges disclosed in the present invention when prepared by persons skilled in the art. The critical parameters include: storage modulus (elastic modulus), loss or viscous modulus, ratio of the above two moduli, yield stress, shear thickening as provided by the viscosity shear rate plot, shear stress as a function of shear rate. Friction factor, friction coefficient, microfriction or micro rheology of the composition by tube flow using tubes coated with biofilm irrespective of biofilm species, values of rheological and tribological parameters at 100%, 50%, 25% concentration and any additional parameters as provided in the details of the present invention.

The required rheological and tribological values need to be adjusted to remove plaque at 100%, 50%, and 25% dilution as detailed elsewhere herein.

The above values may vary somewhat from the disclosed value in the specification and the latter values may not be exact and can vary to some extent by persons skilled in the art. Persons skilled in the art can vary or optimize the composition outside those ranges and can make successful compositions which do not include fibrillated materials to provide dilution-retarding compositions that are effective on removing plaque from teeth.

The fibrillated materials—free dilution retarding compositions may include abrasive or reinforcing particles up to 30% or 50%. Examples of such particles may include but are not limited to silica, calcium carbonate, microcrystalline cellulose or any acceptable organic or inorganic particles at concentration up to 30% or more.

The fibrillated materials—free dilution retarding compositions may include physical or chemical crosslinks which can be provided by nanoparticles such as any form of nano-silica's or particles made from other compositions. Thickening silica are available from different sources where the particle size and surface groups can be tailored to control the density of crosslinks or the strength and rheology of the composition. Crosslinking of polymer thickeners may be based on: hydrogen bonding, acid based interactions, chemical reactions involving formations of electrostatic or covalent bonds. Persons skilled in the art can vary the polymer thickener type and its concentration or use mixtures of polymers and the inorganic (or organic) thickening/crosslinking agents.

Other compositions not including fibrillated materials based on the teaching of embodiment of the invention are contemplated.

The methods and compositions of the invention are not intended to be limited to the use of fibrillated materials and can be made from polymer-based formulations, thickened or crosslinked in anyway, to provide the properties and performance of the compositions of the present invention. The invention is not intended to be limited to use of fibrillated materials but any composition that can deliver the rheological, tribological and plaque removing properties should be considered an integral part of the invention.

An example of a fibrillated-free composition that can retard dilution and can remove stain along with concentration ranges is provided in Table 8.

TABLE 8

Example of Compositions that does not contain fibrils

| Component | wt. % |
|---|---|
| Calcium Carbonate[1] | 10-40 |
| Silica Thickening | 2.6-10 |
| Carrageenan[2] | 1.2-5 |
| Sodium Monofluorophosphate | 1.1 |
| Sodium CMC | 0-3 |
| Tetrasodium Pyrophosphate | 0.6 |
| Sodium Lauryl Sulfate | 1.1 |
| Low Polarity Flavorant | 0.7 |
| Medium Polarity Flavorant | 0-1.2 |
| High Polarity Flavorant | 0-1.2 |
| Sodium Phosphate Tribasic | 0.4-1.0 |
| Sodium Saccharin | 0.25 |
| Sodium Phosphate Monobasic Monohydrate | 0.08 |
| PEG (any type) | 0-2 |
| Water | Balance |

Notes:
[1]This ingredient can be replaced or mixed with acceptable abrasive silica or acceptable particles.
[2]This ingredient can be replaced with other thickeners (e.g., CMO; Polyacrylates; SAP; Xanthan Gum or their mixtures as known in the art).

Further Miscellaneous Comments

All ranges recited herein include ranges therebetween, and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more. If there are two ranges mentioned, such as about 1 to 10 and about 2 to 5, those of skill will recognize that the implied ranges of 1 to 5 and 2 to 10 are within the invention.

Where a sentence states that its subject is found in embodiments, or in certain embodiments, or in the like, it is applicable to any embodiment in which the subject matter can be This invention described herein is of a cleaning composition and methods of forming or using the same. Although some embodiments have been discussed above, other implementations and applications are also within the scope of the following claims. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims. More specifically, those of skill will recognize that any embodiment described herein that those of skill would recognize could advantageously have a sub-feature of another embodiment, is described as having that sub-feature.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

We claim:

1. A cleaning composition for cleaning teeth, said composition comprising:
   (a) a friction component comprising a mixture of:
      fibrillated polymer comprising thicker fibrils and thinner fibrils branched from said thicker fibrils, wherein said thicker fibrils have a diameter of about 250 nm to about 20,000 nm, and
      (ii) 10% to 40% (w/w based on the composition) of abrasive particles, wherein said abrasive particles are compatible with a fluoride source, and said abrasive particles have an average diameter of 5 microns to 50 microns and a hardness of less than 3 on a Mohs Hardness Scale,
   wherein said abrasive particles are entangled in a network of said thicker fibrils and said thinner fibrils of said fibrillated polymer; and
   (b) a sufficient amount of water as a carrier, wherein said composition has viscoelastic fluid properties.

2. The composition of claim 1, wherein:
   said composition satisfies a plaque removal test, said plaque removal test comprising providing said composition at a first concentration and removing biofilm from a tube and providing said composition at a second concentration that is half the first concentration by dilution with water and removing biofilm from said tube, wherein said tube is coated internally with said biofilm and plaque removal is measured by flowing respective compositions through said tubes at a pressure drop per unit length of 1.9 psi/foot for a period of 3 minutes.

3. The composition of claim 1, wherein said composition further comprises particles of a superabsorbent polymer.

4. The composition of claim 1, wherein said composition further comprises particles of a superabsorbent polymer that is surface cross-linked or has a centrifuge retention capacity less than 32.

5. The composition of claim 1, wherein a friction factor of said composition at a first concentration, as measured on a tribometer at sliding speeds between 1 cm/sec and 10 cm/sec between surfaces of glass and polydimethylsiloxane, is greater than 0.15 and wherein a friction factor of said composition at a second concentration that is half the first concentration by dilution with water, as measured on a tribometer at sliding speeds between 1 cm/sec and 10 cm/sec between surfaces of glass and polydimethylsiloxane, is greater than 0.15.

6. The composition of claim 1, wherein the composition comprises less than 0.1% carboxymethylcellulose, if present at all.

7. The composition of claim 1, wherein the composition comprises less than 2.5% surfactants, if present at all.

8. The composition of claim 1, wherein said fibrillated polymer comprises microfibrillated cellulose.

9. The composition of claim 1, wherein said composition further comprises microcrystalline cellulose.

10. The composition of claim 1, wherein said composition has an elastic modulus G' at an oscillatory shear stress of about 3 Pa at an angular frequency of about 1 rad/sec, of 800 Pa or higher.

11. The composition of claim 1, wherein said composition has a yield shear stress of 10 Pa or more.

12. The composition of claim 1, wherein said composition has a viscosity, at a shear rate of $10^{-4}$ $sec^{-1}$, of at least $10^7$ mPa*s.

13. The cleaning composition of claim 1, wherein said composition has an elastic modulus G' that is greater than a loss modulus G" at an oscillatory stress of 3 Pa in an angular frequency range between 0.1 and 100 rad/sec.

14. The composition of claim 1, wherein solid particles in said composition have a maximum dimension that is smaller than a spacing between human teeth at a gumline.

15. The composition of claim 1, wherein the composition is in a form of a paste having a water concentration of 60%-80%.

16. The composition of claim 1, wherein the composition comprises a water concentration of 55%-85%.

17. The composition of claim 1, wherein:
   said composition satisfies a plaque removal test, said plaque removal test comprising applying said composition at a first concentration to clean at least 50% of plaque from a tooth in less than 2 minutes, and wherein said composition provided at a second concentration, when diluted by water to half of the first concentration, is also able to clean at least 50% of said plaque from said tooth, in less than 2 minutes.

18. The composition of claim 1, wherein the composition comprises 10% to 30% (w/w based on the composition) of the abrasive particles.

19. The composition of claim 1, wherein the abrasive particles comprise at least one of silica, hydrated silica, heat treated calcium pyrophosphate, heat treated dicalcium pyrophosphate, sodium metaphosphate, titanium dioxide, perlite, or sodium bicarbonate.

20. The composition of claim 1, wherein the abrasive particles comprise at least one of silica or hydrated silica.

21. The composition of claim 1, further comprising at least one of a stain remover; a whitener; a surfactant for assisting in loosening contaminants from a tooth surface; an antiplaque agent; a tartar control agent; a tooth sensitivity agent; a water activity modifier; a flavorant; a sweetener; or a colorant.

22. The composition of claim 1, wherein:
said composition satisfies a plaque removal test, said plaque removal test comprising providing said composition at a first concentration and removing biofilm from hydroxyapatite and providing said composition at a second concentration that is half the first concentration by dilution with water and removing biofilm from said hydroxyapatite, wherein said hydroxyapatite is coated internally with said biofilm and said plaque removal is measured by flowing respective compositions through said tubes at a pressure drop per unit length of 1.9 psi/foot for a period of 3 minutes.

23. The composition of claim 1, further comprising a source of fluoride ions.

24. The composition of claim 23, wherein the source of fluoride ion comprises at least one of sodium fluoride, stannous fluoride, or sodium monofluorophosphate.

25. The composition of claim 1, wherein the composition further comprises at least one humectant.

26. The composition of claim 9, wherein the microcrystalline cellulose has a size of larger than 25 microns.

27. The composition of claim 9, wherein the microcrystalline cellulose has a size of larger than 50 microns.

28. The composition of claim 9, wherein the microcrystalline cellulose has an aspect ratio larger than 3, wherein the aspect ratio being a ratio of maximum dimension to minimum dimension.

29. A method of cleaning teeth, the method comprising:
(a) applying a cleaning composition to teeth in an oral cavity, the cleaning composition comprising:
 (i) a friction component comprising a mixture of:
  (A) fibrillated polymer comprising thicker fibrils and thinner fibrils branched from said thicker fibrils, wherein said thicker fibrils have a diameter of about 250 nm to about 20,000 nm, and
  (B) 10% to 40% (w/w based on the composition) of abrasive particles, wherein said abrasive particles are compatible with a fluoride source, and said abrasive particles having an average diameter of 5 microns to 50 microns and a hardness of less than 3 on a Mohs Hardness Scale,
 wherein said abrasive particles are entangled in a network of said thicker fibrils and said thinner fibrils of said fibrillated polymer; and
 (ii) a sufficient amount of water as a carrier, wherein said composition has viscoelastic fluid properties; and
(b) causing said composition to move with respect to said teeth, sufficiently to remove plaque from said teeth.

30. The method according to claim 29, wherein:
(a) said applying a cleaning composition to teeth comprises applying using at least one of a manual toothbrush, a rotary toothbrush, a sonic toothbrush or other form of brush, dental floss, dental tape, interproximal brush, and finger brush or other applicator.

31. The method according to claim 29, wherein:
(a) said applying a cleaning composition to teeth comprises applying using a fluid delivery device that delivers said composition with air.

32. The method according to claim 29, wherein:
(a) said applying a cleaning composition to teeth comprises applying using a fluid delivery device that delivers said composition without air.

33. The method of claim 29, wherein the composition further comprises a source of fluoride ions.

34. The method according to claim 29, wherein:
said composition comprises at least one humectant.

35. A cleaning composition for cleaning teeth, said composition comprising:
(a) a friction component comprising a mixture of:
 (i) polysaccharide, and
 (ii) 10% to 40% (w/w based on the composition) of abrasive particles, wherein said abrasive particles are compatible with a fluoride source, and said abrasive particles having an average diameter of 5 microns to 50 microns and a hardness of less than 3 on a Mohs Hardness Scale, wherein said abrasive particles are entangled in a network of said polysaccharide; and
(b) a sufficient amount of water as a carrier, wherein said composition has viscoelastic fluid properties.

36. The composition of claim 35, further comprising a source of fluoride ions.

37. The composition of claim 35, wherein the composition further comprises at least one humectant.

\* \* \* \* \*